(12) United States Patent
Galley et al.

(10) Patent No.: US 6,482,829 B2
(45) Date of Patent: Nov. 19, 2002

(54) SUBSTITUTED HETEROCYCLIC SIPRODECANE COMPOUND ACTIVE AS AN ANTAGONIST OF NEUROKININ 1 RECEPTOR

(75) Inventors: Guido Galley, Rheinfelden (DE); Thierry Godel, Basel (CH); Annick Goergler, Colmar (FR); Torsten Hoffmann, Weil am Rhein (DE); Sabine Kolczewski, Loerrach (DE); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/861,795

(22) Filed: May 21, 2001

(65) Prior Publication Data

US 2002/0006932 A1 Jan. 17, 2002

(30) Foreign Application Priority Data

Jun. 8, 2000 (EP) ............................. 00112285

(51) Int. Cl.[7] .................. A61K 311/454; A61K 31/445; C07D 471/10; C07D 239/00; C07D 221/00
(52) U.S. Cl. ................. 514/278; 514/252.6; 514/235.5; 514/235.8; 514/236.8; 514/249; 514/253.09; 514/245; 514/273; 544/129; 544/211; 544/219; 544/298; 544/332; 544/336; 544/360; 546/16; 546/20
(58) Field of Search ................ 546/16, 20; 514/278, 514/253.09, 235.8, 273, 249, 252.6, 245, 235.5, 236.8; 544/211, 219, 332, 336, 298, 129, 360

(56) References Cited

U.S. PATENT DOCUMENTS 5,776,954 A 7/1998 De Laszlo et al.
5,972,938 A 10/1999 Rupniak

FOREIGN PATENT DOCUMENTS

| EP | 623 589 | 11/1994 |
|---|---|---|
| WO | WO 95/16679 | 6/1995 |
| WO | WO 95/18124 | 7/1995 |
| WO | WO 95/23798 | 9/1995 |
| WO | WO 97/11940 | 4/1997 |
| WO | WO 97/14686 | 4/1997 |
| WO | WO 00/25768 | 5/2000 |

OTHER PUBLICATIONS

*Journal of Autonomic Pharmacol.*, 13 (1993) pp. 23–93.
*Neuropeptides*, 32(1) (1998) pp. 1–49.
*Eur. J. Pharmacol.*, 383(3) (1999) pp. 297–303.
Desai et al., Tetrahedron Letters, vol. 34, No. 48, pp. 7685–7688 (1993).

*Primary Examiner*—Evelyn Mei Huang
(74) *Attorney, Agent, or Firm*—George W. Johnston; Patricia S. Rocha-Tramaloni; Arthur D. Dawson

(57) ABSTRACT

The invention relates to compounds of the formula

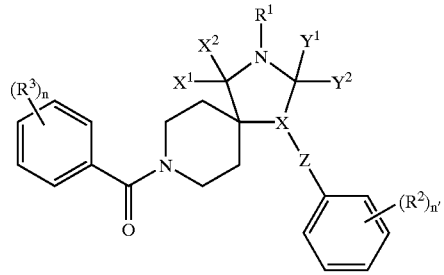

as described herein and pharmaceutically acceptable acid addition salts thereof. The described compounds have a good affinity to the NK1 receptor.

211 Claims, No Drawings

SUBSTITUTED HETEROCYCLIC SIPRODECANE COMPOUND ACTIVE AS AN ANTAGONIST OF NEUROKININ 1 RECEPTOR

FIELD OF INVENTION

The present invention is generally a heterocyclic spirodecane and more particularly a substituted heterocyclic spiro[4.5]decane with activity at the NK-1, substance P receptor.

BACKGROUND

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmacol., 13, 23–93, 1993.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

NK1 receptor antagonists have been reported to have also a beneficial effect in the therapy of traumatic brain injury (oral disclosure by Prof. Nimmo at the International Tachykinin Conference 2000 in La Grande Motte, France, Oct. 17–20, 2000 with the title "Neurokinin 1 (NK-1) Receptor Antagonists Improve the Neurological Outcome Following Traumatic Brain Injury" (Authors: A. J. Nimmo, C. J. Bennett, X. Hu, I. Cernak, R. Vink)."

SUMMARY

A compound of the present invention has the formula

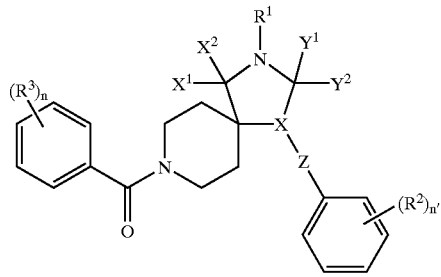

wherein
$R^1$ is hydrogen, lower alkyl, lower alkenyl, phenyl or the following groups
—$(CH_2)_m$-non aromatic heterocyclyl, which is unsubstituted or substituted by lower alkyl, or is
—$(CH_2)_m$-heteroaryl, which is unsubstituted or substituted by one or two substituents selected from the group consisting of lower alkyl, lower alkoxy, halogen, $CF_3$, benzyl or cyano, or is
—$(CH_2)_m$—C(O)—NRR',
—$(CH_2)_m$—C(O)-lower alkyl,
—$(CH_2)_m$—C(O)—O-lower alkyl,
—$(CH_2)_m$—O-lower alkyl,
—$(CH_2)_m$—CH[C(O)—O-lower alkyl]$_2$,
—$(CH_2)_m$CH(OH)—CH$_2$—O-phenyl,
—$(CH_2)_m$—CH(CF$_3$)OH,
—$(CH_2)_m$—OH,
—$(CH_2)_m$—CN,
—$(CH_2)_m$—NRR',
—$(CH_2)_m$-cycloalkyl or
—$(CH_2)_m$—CHF$_2$;
$R^2$ is hydrogen, lower alkyl, halogen or lower alkoxy;
$R^3$ is lower alkyl, lower alkoxy, halogen or $CF_3$;
R,R' are the same or different and are hydrogen or lower alkyl;
X is >N—, or >CH—;
$X^1/X^2$ are independently from each other hydrogen, hydroxy or lower alkoxy or may be together an oxo group;
$Y^1/Y^2$ are independently from each other hydrogen, lower alkyl, —$(CH_2)_m$-phenyl or may be together an oxo group;
Z is a —$(CH_2)_q$— or —C(O)—;
m is 0, 1, 2, 3 or 4;
n is 2 or 3;
n' 0, 1 or 2;
q is 0 or 1;
or pharmaceutically acceptable acid addition salts thereof.
A compound of formula I or its salts are characterized by valuable therapeutic properties. It has been surprisingly found that the compound of the present invention is an antagonist of the Neurokinin 1 (NK-1, substance P) receptor.

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

Preferred compounds of the present invention include, but are not limited to:

The compound having the formula

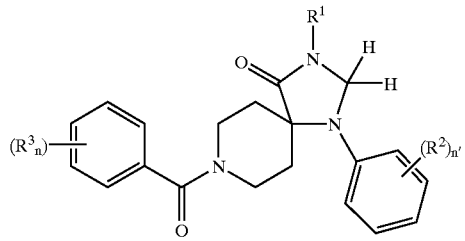

I-b wherein $R^1$, $R^2$ and $R^3$ are as defined above and wherein n=2 and one of $R^3$ is F and the other of $R^3$ is $CF_3$.

Another preferred compound based on formula I-a has the formula I-c with $R^1$ being hydrogen, lower alkyl, —$(CH_2)_m$-cycloalkyl, —$(CH_2)_m$—NRR' or —$(CH_2)_m$-unsubstituted non-aromatic; and m=0, 1, 2, 3, 4.

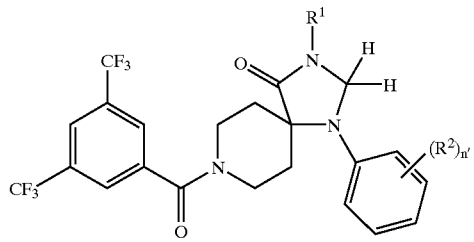

I-c wherein $R^1$ and $R^2$ are as defined above; or further including $R^1$ being hydrogen and $R^2$ being hydrogen; and wherein $R^1$ is phenyl or —$(CH_2)_m$-unsubstituted heteroaromatic alkyl. A further preferred embodiment based on structure I-c includes $R^1$ being —$(CH_2)_m$-substituted heteroaryl and $R^2$ being hydrogen; $R^1$ being substituted or unsubstituted-$(CH_2)_m$-non aromatic heterocyclic or, —$(CH_2)_m$—NRR' and $R^2$ being hydrogen; $R^1$ being a —$(CH_2)_m$—O—O-lower alkyl, —$(CH_2)_m$—O-lower alkyl or —$(CH_2)_m$—CH(OH)—$CH_2$—O-phenyl and $R^2$ being hydrogen; $R^1$ being —$(CH_2)_m$—$CF_3$, —$(CH_2)_m$ CN or —$(CH_2)_m$ OH; $R^1$ being unsubstituted or substituted-$(CH_2)_m$-heteroaryl, m is 0, 1, 2, 3 or 4; and $R^2$ is halogen and n' is 1 or 2; $R^1$ is —$(CH_2)$m—OH, unsubstituted or substituted-$(CH_2)$m-heteroaryl, m is 0, 1, 2, 3 or 4; and $R^2$ is lower alkyl or lower alkoxy; $R^1$ is hydrogen, $R^2$ is lower alkyl, lower alkoxy or halogen and wherein n' is 1 or 2; or $R^1$ being —$(CH_2)_m$—C(O)—NRR', —$(CH_2)_m$—CH—$(CF3)$OH or unsubstituted or substituted-$(CH_2)_m$-non-aromatic heterocyclic wherein m is 1, 2, 3 or 4 and $R^2$ is hydrogen or halogen.

Another preferred embodiment has the formula

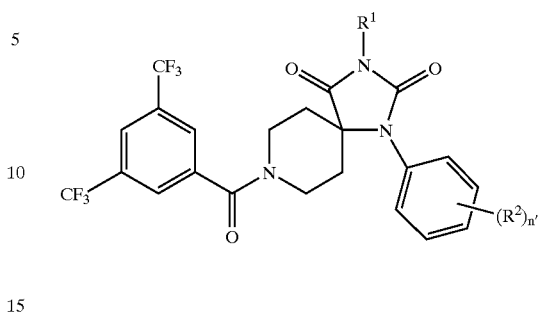

I-d wherein $R^1$ and $R^2$ are as defined above. Yet another preferred embodiment based on formula I-d includes $R^1$ being hydrogen, lower alkyl, phenyl or —$(CH_2)_m$-unsubstituted or substituted heterocyclic non-aromatic heterocyclic; and $R^2$ being hydrogen or lower alkyl, m is 1, 2, 3, 4; or further includes $R^1$ being lower alkyl, —$(CH_2)_m$-unsubstituted and substituted heteroaromatic, m=0, 1, 2, 3, 4; or $R^1$ being —$(CH2)_m$-unsubstituted or substituted heteroaromatic and $R^2$ being halogen.

A further preferred embodiment includes the structure

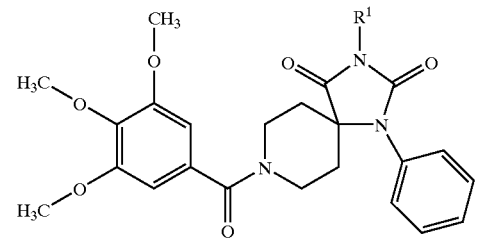

I-e wherein $R^1$ is hydrogen.

Yet another preferred embodiment has the structure

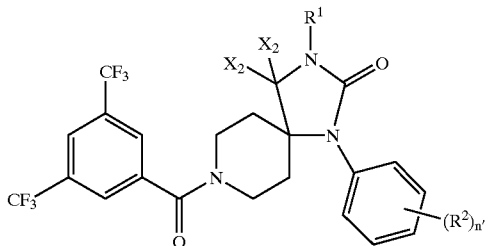

I-f wherein $R^1$, $R^2$, $X^1$ and $X^2$ are as defined above. A further preferred embodiment based on the structure I-f includes $X^1$ or $X^2$ being hydrogen, hydroxy or lower alkoxy, $R^1$ being hydrogen, phenyl or —$(CH_2)_m$-unsubstituted or substituted non-aromatic heterocyclic; and $R^2$ being hydrogen or lower alkyl.

A further preferred embodiment has the structure I-g

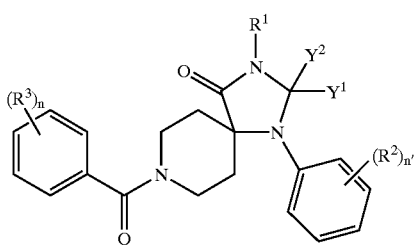

wherein $Y^1$ or $Y^2$, $R^1$, $R^2$ and $R^3$ are as above or $R^1$ being —(CH$_2$)$_m$-substituted or unsubstituted heteroaryl. Another preferred embodiment based on the structure I-g includes $R^1$ being hydrogen, $R^2$ being lower alkyl and $R^3$ being halogen, OCF$_3$ or CF$_3$.

A further embodiment having the formula

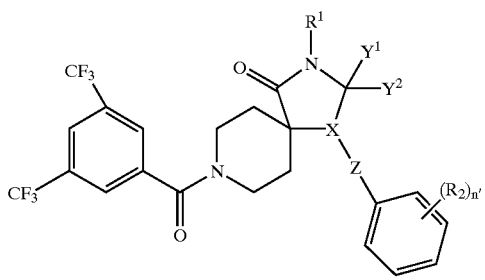

wherein $R^1$ is hydrogen, —(CH$_2$)$_m$-nonaromatic heterocyclic or lower alkyl; $R^2$is hydrogen or halogen; $Y^1$, $Y^2$ and Z are as above: or wherein, $Y^1$ and $Y^2$ being hydrogen and Z being —(CH$_2$)$_0$— or —C(O)—; or one of $Y^1$ and $Y^2$ being hydrogen, and the other of $Y^1$ and $Y^2$ being lower alkyl; Z being —(CH$_2$)$_o$—; and $R^1$ being hydrogen, lower alkyl, —(CH$_2$)$_m$—NRR', —(CH$_2$)$_m$-cyclo alkyl or —(CH$_2$)$_m$-unsubstituted non aromatic heterocyclic; or of $Y^1$ and $Y^2$ being hydrogen, and the other of $Y^1$ and $Y^2$ being lower alkyl; Z being —(CH$_2$)$_0$—; $R^1$ being phenyl, —(CH$_2$)$_m$—O-lower alkyl, —(CH$_2$)$_m$—CHF$_2$ or lower alkenyl; and $R^2$ being lower alkyl; or further comprising one of $Y^1$ and $Y^2$ being hydrogen, and the other of $Y^1$ and $Y^2$ being lower alkyl; Z being —(CH$_2$)$_0$—; $R^1$ being unsubstituted-(CH$_2$)$_m$-aromatic heterocyclic or substituted-(CH2)$_m$-aromatic heterocyclic; and R$_2$ being hydrogen or lower alkyl; or further comprising one of $Y^1$ and $Y^2$ being hydrogen, and the other of $Y^1$ and $Y^2$ being —(CH$_2$)$_m$-phenyl; Z being —(CH$_2$)$_0$—; $R^1$ being hydrogen or lower alkyl; and $R^2$ being hydrogen or lower alkyl.

A further preferred embodiment has the structure

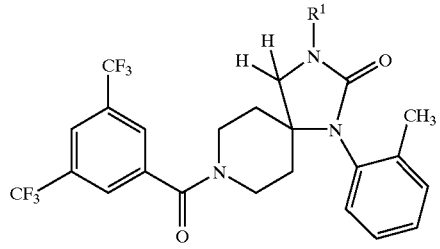

wherein $R^1$ is —(CH$_2$)$_m$-cycloalkyl, —(CH$_2$)$_m$-unsubstituted heterocyclic, —(CH$_2$)$_m$—O-lower alkyl, —(CH$_2$)$_m$—NRR' or —(CH$_2$)$_m$—C(O)-lower alkyl; and m=0, 1, 2, 3,4.

Yet another preferred embodiment has the structure

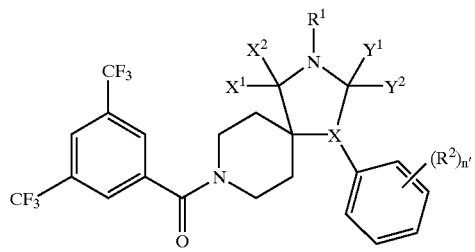

wherein $R^1$ is lower alkyl, $X^1$ and $X^2$ are as above, $Y^1$ and $Y^2$ are as above, $R^2$ is hydrogen and X is >CH—; or wherein $X^1$ and $X^2$ being taken together to form an oxo group, $Y^1$ and $Y^2$ being hydrogen, $R^2$ being hydrogen or lower alkyl and $R^1$ being hydrogen, lower alkyl, —(CH$_2$)$_m$-cycloalkyl, —(CH$_2$)$_m$-unsubstituted non-aromatic heterocyclic, —(CH$_2$)$_m$—O-lower alkyl, —(CH$_2$)$_m$—NRR', —(CH$_2$)$_m$—C(O)-lower alkyl or —(CH$_2$)$_m$ unsubstituted heteroaryl; or wherein $X^1$ and $X^2$ being taken together form an oxo group; $Y^1$ and $Y^2$ being taken together form an oxo group; and $R^1$ being hydrogen, lower alkyl, —(CH$_2$)$_m$-unsubstituted non-aromatic heterocyclic or —(CH$_2$)$_m$—NRR'; and $R^2$ being hydrogen.

A compound of the invention has the structure

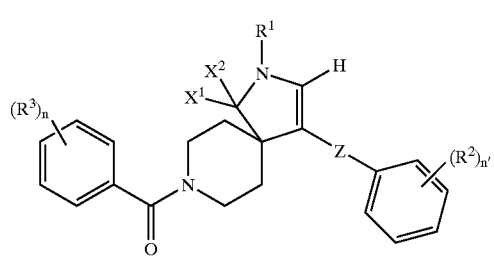

wherein
$R^1$ is hydrogen, lower alkyl, lower alkenyl, phenyl or the following groups
—(CH$_2$)$_m$-non aromatic heterocyclic, which is unsubstituted or substituted by lower alkyl, or is —(CH$_2$)$_m$-heteroaryl, which is unsubstituted or substituted by one or two substituents selected from the group consisting of lower alkyl, lower alkoxy, halogen, CF$_3$, benzyl or cyano, or is
—(CH$_2$)$_m$—C(O)—NRR',
—(CH$_2$)$_m$—C(O)-lower alkyl,
—(CH$_2$)$_m$—C(O)—O-lower alkyl,
—(CH$_2$)$_m$—O-lower alkyl,
—(CH$_2$)$_m$—CH[C(O)—O-lower alkyl]$_2$,
—(CH$_2$)$_m$CH(OH)—CH$_2$—O-phenyl,
—(CH$_2$)$_m$—CH(CF$_3$)OH,
—(CH$_2$)$_m$—OH,
—(CH$_2$)$_m$—CN,
—(CH$_2$)$_m$—NRR',
—(CH$_2$)$_m$-cycloalkyl or
—(CH$_2$)$_m$—CHF$_2$ R$^2$ is hydrogen, lower alkyl, halogen or lower alkoxy;
R$^3$ is lower alkyl, lower alkoxy, halogen or CF$_3$;
R,R' are the same or different and are hydrogen or lower alkyl;
X$^1$/X$^2$ are hydrogen, hydroxy or lower alkoxy or taken together to form an oxo group;
Z —(CH$_2$)$_q$— or —C(O)—;
m is 0, 1, 2, 3 or 4;
n is 2 or 3;
n' 0, 1 or 2;
q is 0 or 1;
or pharmaceutically acceptable acid addition salts thereof.

A preferred embodiment of the compound with structure I-k has the structure

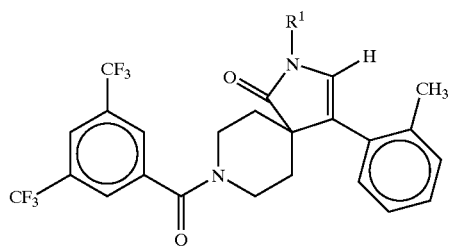

I-1 wherein is R$^1$ as above or wherein R$^1$ being hydrogen, lower alkyl, —(CH$_2$)$_m$-cycloalkyl, —(CH$_2$)$_m$—NRR' or —(CH$_2$)$_m$-unsubstituted non-aromatic; and m=0, 1, 2, 3, 4.

Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

The compounds of formula I can also be used in form of their prodrugs. Examples are esters, N-oxides, phosphate esters, glycoamide esters, glyceride conjugates and the like. The prodrugs may add to the value of the present compounds advantages in absorption, pharmocokinetics in distribution and transport to the brain.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION

The following definitions of the general terms used in the present description apply irrespective of whether the terms in question appear alone or in combination.

As used herein, the term "lower alkyl" denotes a saturated straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

As used herein, the term "lower alkenyl" denotes a unsaturated straight- or branched-chain alkyl group containing from 2–7 carbon atoms, for example, ethenyl, propenyl, isopropenyl, n-butenyl, i-butenyl, t-butenyl and the like.

Preferred lower alkyl groups are groups with 2–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3–6 carbon atoms.

The term "non aromatic heterocyclyl" denotes, for example, pyrrolidinyl, 5-oxo-pyrrolidinyl, 2-oxa-oxazolidinyl, piperidyl, piperazinyl, morpholinyl, imidazolidinyl or pyrazolidinyl. Preferred groups are pyrrolidinyl, 5-oxo-pyrrolidinyl, 2-oxa-oxazolidinyl, piperidyl, piperazinyl or morpholinyl.

The term "heteroaryl" denotes, for example pyridinyl, 1,3,5-triazinyl, pyrimidinyl, quinoxalinyl, pyrazinyl, isoxazolyl, benzoimidazolyl, 1,2,4-oxadiazolyl, triazolyl, tetrazolyl, thiazolyl, thienyl, furyl, pyranyl, pyrrolyl, imidazolyl, pyrazolyl, isothiazolyl, piperazinyl or piperidyl. Preferred groups are pyridinyl, 1,3,5-triazinyl, pyrimidinyl, quinoxalinyl, pyrazinyl, imidazolyl, thiazolyl, isoxazolyl, benzoimidazolyl, 1,2,4-oxadiazolyl, furyl and thienyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Preferred are all compounds, wherein R$^3$ is trifluoromethyl and n is 2.

Exemplary preferred are compounds, in which X is >N—, X$^1$/X$^2$ are together an oxo group and Y$^1$/Y$^2$ are both hydrogen, for example the following compounds:ps
8-(3,5-Bis-trifluoromethyl-benzoyl)-3-(4,6-dimethoxy-[1,3,5]triazin-2-yl)-1-phenyl-1,3,8-triaza-spiro[4.5]decan-4-one,
8-(3,5-bis-trifluoromethyl-benzoyl)-1-(2-chloro-phenyl)-3-(4,6-dimethoxy-[1,3,5]triazin-2-yl)-1,3,8-triaza-spiro[4.5]decan-4-one,
8-(3,5-,bis-trifluoromethyl-benzoyl)-3-pyridin-3-yl-methyl-1-o-tolyl-1,3,8-triaza-spiro[4.5]decan-4-one,
8-(3,5-bis-trifluoromethyl-benzoyl)-3-(2-isopropylamino-ethyl)-1-o-tolyl-1,3,8-triaza-spiro[4.5]decan-4-one,
8-(3,5-bis-trifluoromethyl-benzoyl)-3-(2-pyrrolidin-1-yl-ethyl)-1-o-tolyl-1,3,8-triaza-spiro[4.5]decan-4-one,
8-(3,5-bis-trifluoromethyl-benzoyl)-1-phenyl-3-pyridin-4-yl-1,3,8-triaza-spiro[4.5]decan-4-one, 8-(3,5-bis-trifluoromethyl-benzoyl)-1-(2-chloro-phenyl)-3-methyl-1,3,8-triaza-spiro[4.5]decan-4-one,
8-(3,5-bis-trifluoromethyl-benzoyl)-1-(2-chloro-phenyl)-3-(3-dimethylamino-propyl)-1,3,8-triaza-spiro[4.5]decan-4-one,
8-(3,5-bis-trifluoromethyl-benzoyl)-1-(2-chloro-phenyl)-3-pyridin-4-yl-1,3,8-triaza-spiro[4.5]decan-4-one and
8-(3,5-bis-trifluoromethyl-benzoyl)-3-methyl-1-o-tolyl-1,3,8-triaza-spiro[4.5]decan-4-one.

Further preferred are compounds, in which X is >N—, $X^1/X^2$ are together an oxo group and one of $Y^1/Y^2$ is hydrogen and the other is different from hydrogen.
Examples of such compounds are:

(rac)-8-(3,5-bis-trifluoromethyl-benzoyl)-2-methyl-1-phenyl-1,3,8-triaza-spiro[4.5]decan-4-one,
(rac)-8-(3,5-bis-trifluoromethyl-benzoyl)-2-methyl-1-o-tolyl-1,3,8-triaza-spiro[4.5]decan-4-one,
(rac)-2-benzyl-8-(3,5-bis-trifluoromethyl-benzoyl)-1-o-tolyl-1,3,8-triaza-spiro[4.5]decan-4-one,
(rac)-8-(3,5-bis-trifluoromethyl-benzoyl)-2-phenyl-1-o-tolyl-1,3,8-triaza-spiro[4.5]decan-4-one,
(rac)-8-(3,5-bis-trifluoromethyl-benzoyl)-2-methyl-1-phenyl-3-pyridin-3-yl-methyl-1,3,8-triaza-spiro[4.5]decan-4-one,
(rac)-8-(3,5-bis-trifluoromethyl-benzoyl)-2,3-dimethyl-1-phenyl-1,3,8-triaza-spiro[4.5]decan-4-one,
(rac)-8-(3,5-bis-trifluoromethyl-benzoyl)-2methyl-1-phenyl-3-(2-pyrrolidin-1-yl-ethyl)-1,3,8-triaza-spiro[4.5]decan-4-one,
(rac)-8-(3,5-bis-trifluoromethyl-benzoyl)-3-(3-dimethylamino-propyl)-2-methyl-1-phenyl-1,3,8-triaza-spiro[4.5]decan-4-one,
(rac)-8-(3,5-bis-trifluoromethyl-benzoyl)-2,3-dimethyl-1-o-tolyl-1,3,8-triaza-spiro[4.5]decan-4-one,
(rac)-8-(3,5-bis-trifluoromethyl-benzoyl)-2-methyl-3-(2-piperazin-1-yl-ethyl)-1-o-tolyl-1,3,8-triaza-spiro[4.5]decan-4-one,
(rac)-8-(3,5-bis-trifluoromethyl-benzoyl)-2-methyl-3-(2-pyrrolidin-1-yl-ethyl)-1-o-tolyl-1,3,8-triaza-spiro[4.5]decan-4-one,
(rac)-8-(3,5-bis-trifluoromethyl-benzoyl)-2-methyl-3-(2-piperidin-1-yl-ethyl)-1-o-tolyl-1,3,8-triaza-spiro[4.5]decan-4-one,
(rac)-8-(3,5-bis-trifluoromethyl-benzoyl)-3-(2-methoxy-ethyl)-2-methyl-1-o-tolyl-1,3,8-triaza-spiro[4.5]decan-4-one,
(rac)-8-(3,5-bis-trifluoromethyl-benzoyl)-2-methyl-3-(2-morpholin-4-yl-ethyl)-1-o-tolyl-1,3,8-triaza-spiro[4.5]decan-4-one and
(rac)-8-(3,5-dichloro-benzoyl)-2-methyl-1-o-tolyl-1,3,8-triaza-spiro[4.5]decan-4-one.

Preferred are further compounds, wherein X is >N—, $X^1/X^2$ and $Y^1/Y^2$ are oxo groups, for example the following compounds:

8-(3,5-bis-trifluoromethyl-benzoyl)-1-o-tolyl-1,3,8-triaza-spiro[4.5]decane-2,4-dione,
8-(3,5-bis-trifluoromethyl-benzoyl))-3-pyridin-3-yl-methyl-1-o-tolyl-1,3,8-triaza-spiro[4.5]decane-2,4-dione,
3-(1H-benzoimidazol-2-yl-methyl)-8-(3,5-bis-trifluoromethyl-benzoyl)-1-o-tolyl-1,3,8-triaza-spiro[4.5]decane-2,4-dione,
8-(3,5-bis-trifluoromethyl-benzoyl)-3-(2-methyl-thiazol-4-yl-methyl)-1-o-tolyl-1,3,8-triaza-spiro[4.5]decane-2,4-dione,
8-(3,5-bis-trifluoromethyl-benzoyl)-3-furan-2-yl-methyl-1-phenyl-1,3,8-triaza-spiro[4.5]decane-2,4-dione,
8-(3,5-bis-trifluoromethyl-benzoyl)-3-furan-2-yl-methyl-1-o-tolyl-1,3,8-triaza-spiro[4.5]decane-2,4-dione and
8-(3,5-bis-trifluoromethyl-benzoyl)-3-thiophen-2-yl-methyl-1-o-tolyl-1,3,8-triaza-spiro[4.5]decane-2,4-dione.

Preferred are further compounds, wherein X is >C=, for example the following compounds:

8-(3,5-bis-trifluoromethyl-benzoyl)-2-(2-pyrrolidin-1-yl-ethyl)-4-o-tolyl-2,8-diaza-spiro[4.5]dec-3-en-1-one and
8-(3,5-bis-trifluoromethyl-benzoyl)-2-(3-dimethylamino-propyl)-4-o-tolyl-2,8-diaza-spiro[4.5]dec-3-en-1-one.

Further preferred are compounds, wherein X is >CH—, for example the following compound:

(rac)-8-(3,5-bis-trifluoromethyl-benzoyl)-4-o-tolyl-2,8-diaza-spiro[4.5]decan-1-one.

The present compounds of formula I and their pharmaceutically acceptable salts can be prepared by methods known in the art, for example, by processes described below, which process comprises
reacting a compound of formula

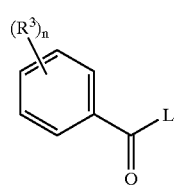

II with a compound of formula

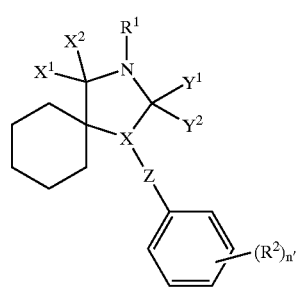

III to a compound of formula

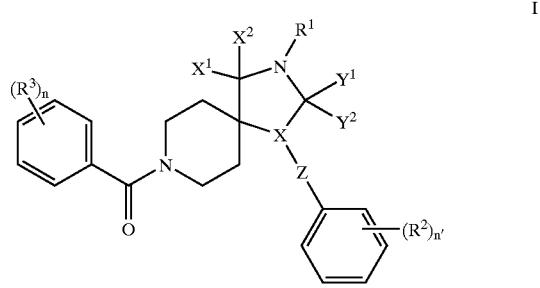

I wherein L is a leaving group, for example halogen, such as chlorine, and the other substituents have the significances given above, or reacting a compound of formula

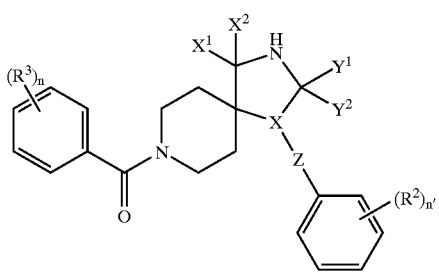

I-1 with a compound of formula in the presence of sodium hydride or in the presence of potassium carbonate and CuCl, wherein in formula IV L is a leaving group, for example chlorine, to give a compound of formula

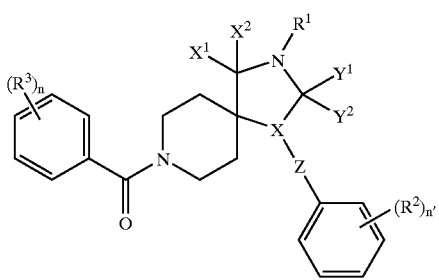

I wherein the other substituents have the significances given above with the proviso that $R^1$ is not $-(CH_2)_m-OH$ and $X^1/X^2$ are not hydroxy, or reacting a compound of formula

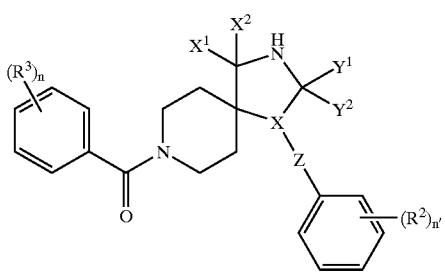

I-1 with a compound of formula

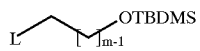

to a compound of formula

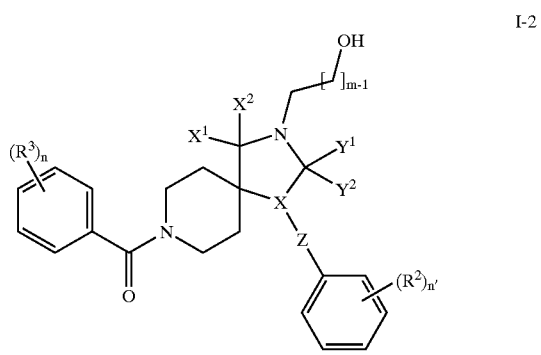

I-2 wherein TBDMS is a tert-butyldimethylsilyl group and the further definitions of substituents is given above, or reacting a compound of formula

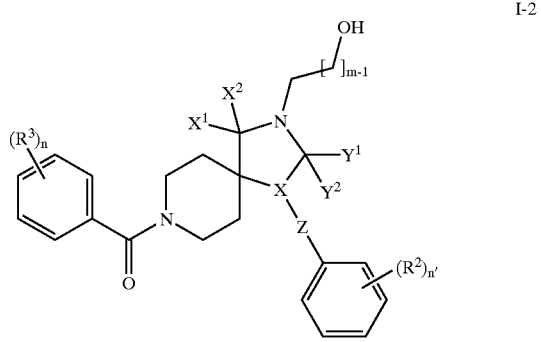

I-2 after activation as mesylate with a corresponding amine of formula

RR'NH to give a compound of formula

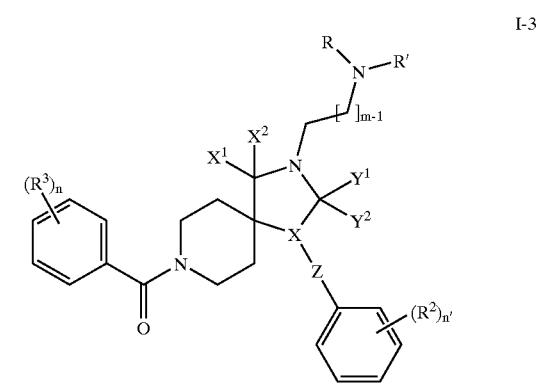

I-3 wherein the definitions of substituents are given above, or reacting a compound of formula

I-1 with a compound of formula

VI to a compound of formula

I-4 wherein R⁴ is lower alkyl and the definitions of the other substituents are given above, or reacting a compound of formula

I-1 with a compound of formula

VII to a compound of formula

I wherein $R^1$ is phenyl or heteroaryl, optionally substituted as described above and the definition of the remaining substituents is given above, or cyclizing a compound of formula

VIII to a compound of formula

I-5 wherein the substituents are described above, or reacting a compound of formula

I-6 with

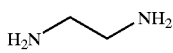

to give a compound of formula

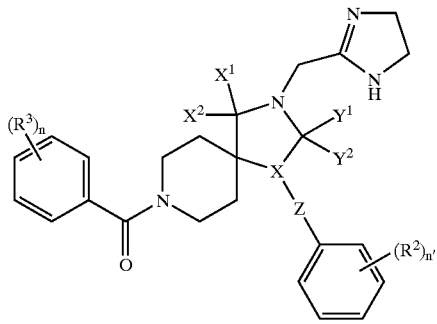

I-7 wherein the substituents are described above, or treating a compound of formula

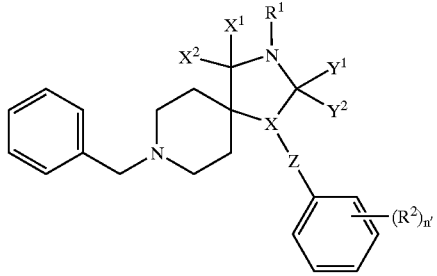

with hydrogen on Pd/C and then with $(CF_3)_2C_6H_3COCl$ to obtain a compound of formula

I-12

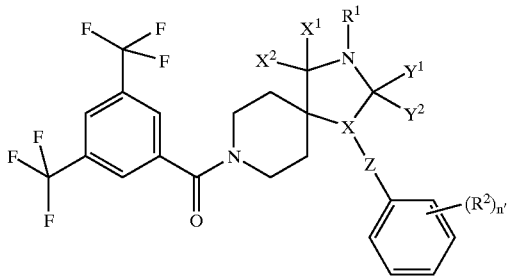

wherein the substituents are given above, or modifying one or more substituents $R^1$–$R^3$ within the definitions given above, and if desired, converting the compound obtained into a pharmaceutically acceptable acid addition salt.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–17 describe the processes for preparation of compounds of formula I in more detail. The starting materials are known compounds and may be prepared according to methods known in the art.

In the schemes the following abbreviations have been used:

| | |
|---|---|
| NMP | 1-methyl-2-pyrrolidinone |
| DME | ethylene glycol dimethyl ether |
| TBDMS | tert.-butyldimethylsilan |
| DMF | dimethylformamide |
| THF | tetrahydrofuran |
| TMSCN | trimethylsilyl cyanide |
| DIBAH | diisobutylaluminium hydride |

Scheme 1

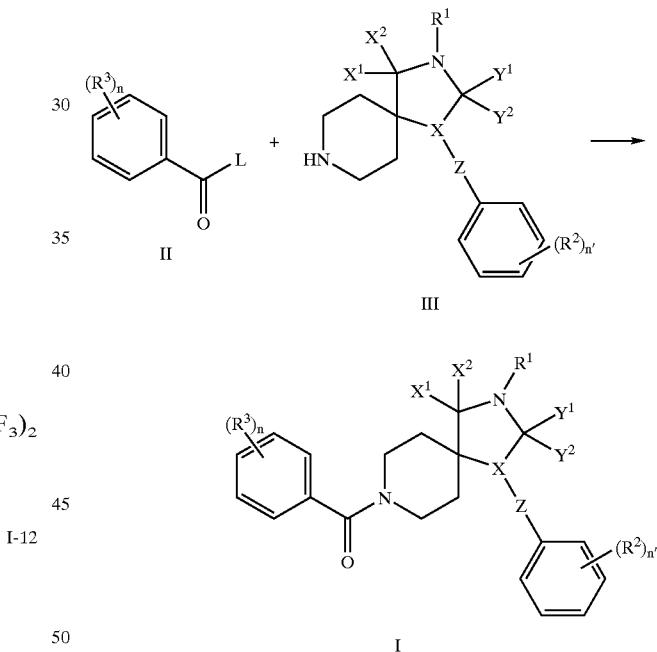

wherein in scheme 1 L is a leaving group, for example halogen, such as chlorine, and the other substituents have the significances given above.

A solution of a compound of formula II, for example 3,5-bis(trifluoromethyl)benzoyl chloride in dichloromethane, is added to a mixture of a compound of formula III, which is for example 1-phenyl-1,3,8-triaza-spiro[4.5]decan-4-one and triethylamine in dichloromethane. The reaction is carried out at room temperature.

Compounds of examples 1 to 3 have been prepared according to scheme 1.

Scheme 2

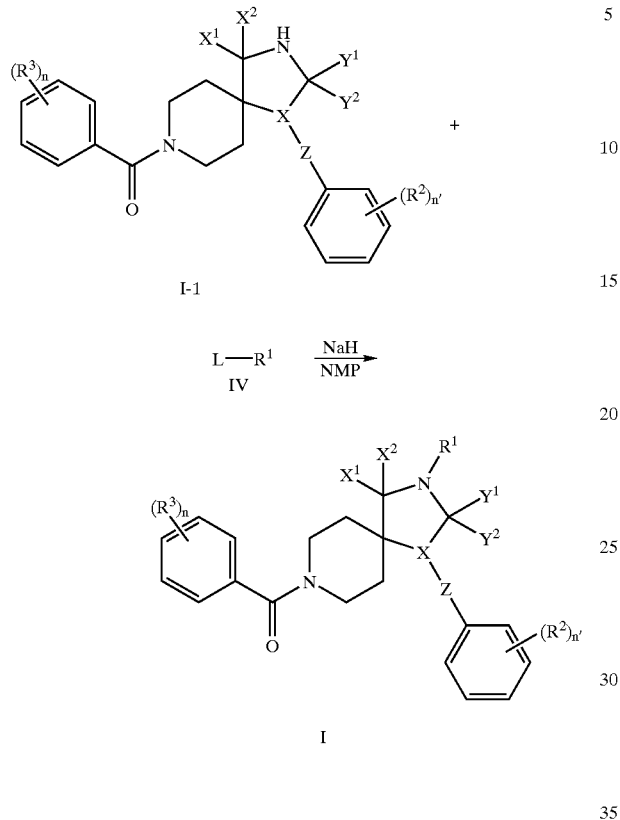

The definition of substituents is described above.

This reaction is carried out in the presence of sodium hydride and/or NMP (N-methyl-2-pyrrolidone)/1,2-dimethoxyethane. To this suspension is added a compound of formula I-1 and then a compound of formula IV is added, which is, for example, 4-(2-chloroethyl)morpholine, 3-(chloromethyl)pyridine, 2-chloro-4,6-dimethoxy-1,3,5-triazine, 1-(2-chloroethyl)piperidine, 1-(2-chloroethyl) pyrrolidine, 2-bromoacetamide, 2-chloro-N,N-dimethylacetamide, methyl bromoacetate, bromomethyl methylether, dimethyl bromomalonate, phenylglycidylether, 2,4,6-trichloropyrimidine, 2-chloro-5-(trifluoromethyl) pyridine, 3-bromo-1,1,1-trifluoro-2-propanole, 2-picolylchloride, 4-chloromethylpyridine, 2,4-dichloropyrimidine, methyliodide, 1-benzyl-(2-chloromethyl)-imidazole, 5-chloromethyl-2-oxazolidinone, 1-chloro-2-dimethylaminoethane, 1-(2-chloroethyl) pyrrolidine, 4-chloromethyl-2-methylthiazole, 4,6-dichloropyridine, 2,3,5-trichloropyridine, 2-chloro-4-(trifluoromethyl)-pyrimidine, 2-chloro-pyridine, 2-chloro-N,N-dimethylacetamide, 3-dimethylaminopropylchloride, 4-(chloromethyl)3,5-dimethylisoxazole or 2,4-dichloro-6-methylpyrimidine.

Examples 4 to 21, 25 to 47, 70 to 82 and 86, 87 and 134 have been described in accordance with scheme 2 in more detail.

Scheme 3

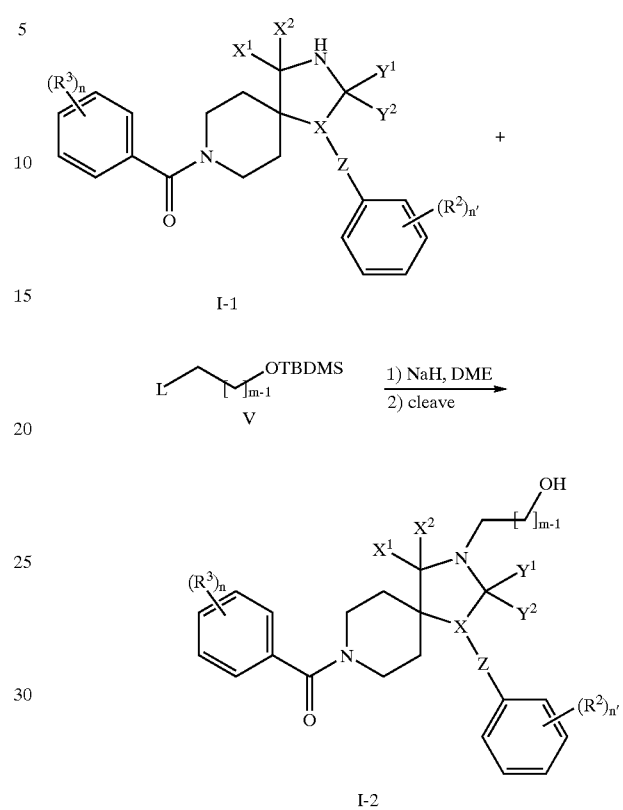

The definition of substituents is described above.

This reaction is carried out under conditions described in scheme 2, with a compound of formula I-1 and of formula V, which compound is, for example (3-bromopropoxy)-tert.-butyldimethylsilane. In a solution of HCl and ethanol the intermediate TBDMS-ether is cleaved.

Examples 22 to 24 have been described in accordance with scheme 3.

Scheme 4

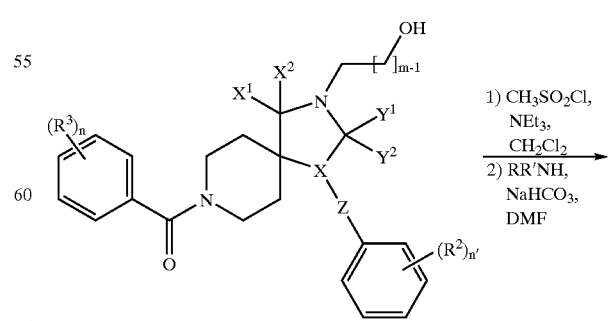

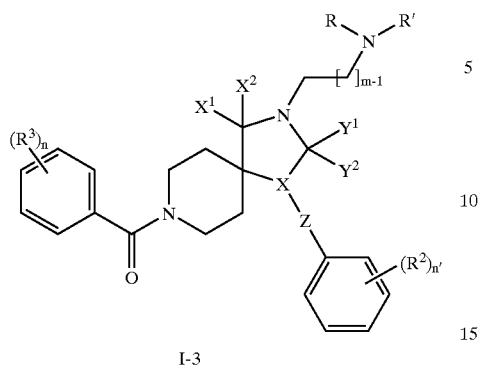

I-3

The definition of substituents is given above.

A solution of a compound of formula I-2 and triethylamine in dichloromethane is added to a cooled solution of methanesulfonyl chloride in dichloromethane or DMF and then sodium bicarbonate and an amine of the formula RR'NH is added to obtain a compound of formula I-3.

Examples 48 to 58 have been described in accordance with scheme 4.

Scheme 5

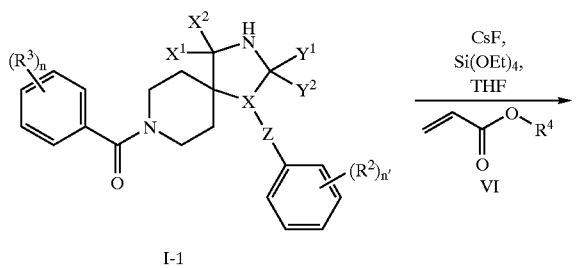

I-1

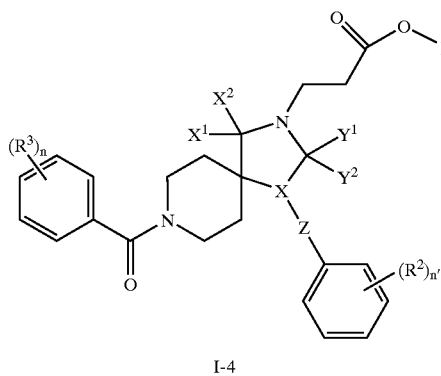

I-4

In scheme 5 $R^4$ is lower alkyl and the definition of the other substituents is given above.

In accordance with this scheme to a mixture of a compound of formula I-1, cesium fluoride and tetraethoxysilane, a compound of formula VI, for example ethyl acrylate, is added. The reaction is carried out at room temperature.

Examples 59 and 60 have been prepared as described in scheme 5.

Scheme 6

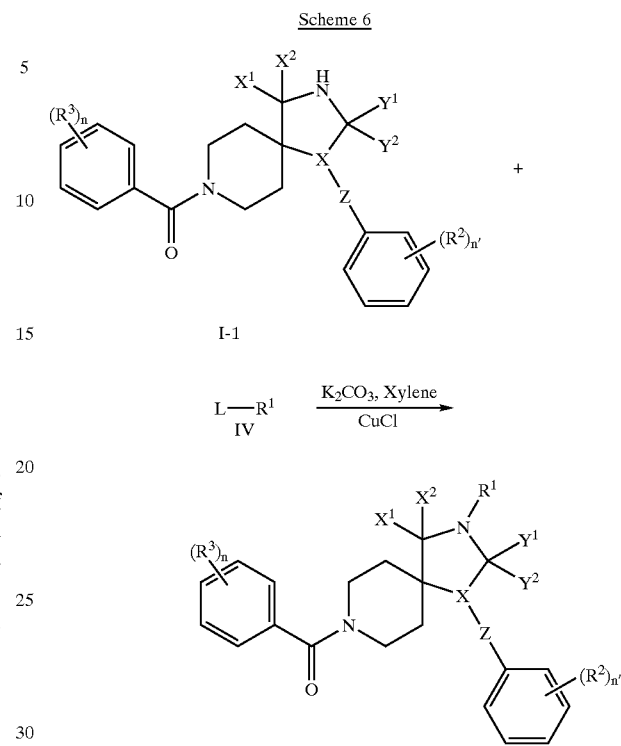

I

The definition of substituents is described above.

This reaction is carried out with a mixture of a compound of formula I-1 in the presence of potassium carbonate, CuCl and tris[2-(2-methoxyethoxy)-ethyl]-amine, and with a solution of a compound of formula IV, which is, for example, 4,6-dichloropyrimidine in xylene.

Example 61 has been described in accordance with scheme 6.

Scheme 7

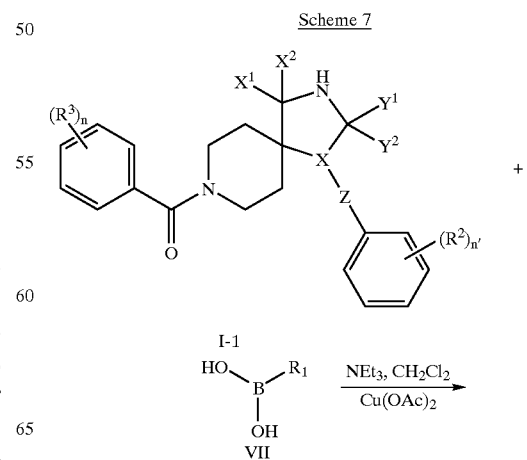

-continued

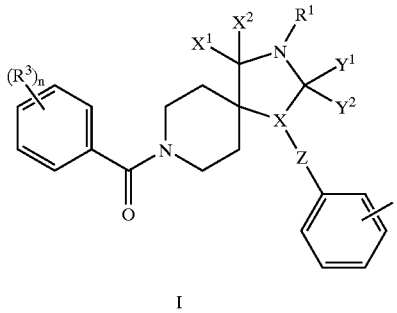

I

The definition of substituents is given above.

A mixture of a compound of formula I-1, a boronic acid of formula VII, cupric acetate and triethylamine in dichloromethane is stirred at room temperature. Chromatography on silica gel yielded the desired compound of formula I.

Examples 62, 83 and 84 describe the process of scheme 7 in more detail.

Scheme 8

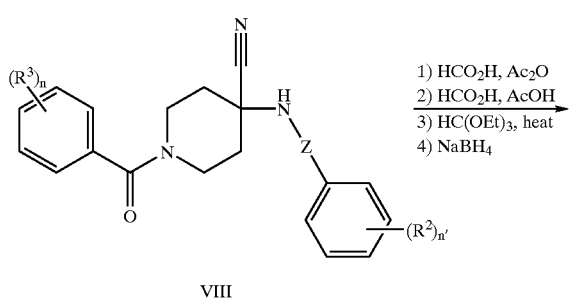

VIII

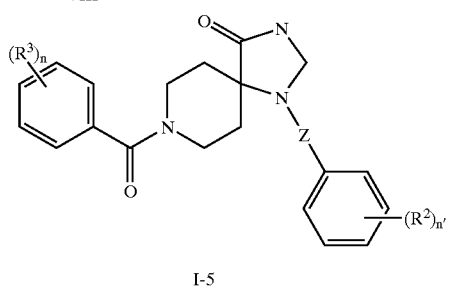

I-5

The definition of substituents is described above.

A mixture of a compound of formula VIII, formic acid and acetic anhydride is stirred at room temperature to give the intermediate N-formyl derivative, which is treated with formic acid and acetic acid to give the intermediate amide. The amide is dissolved in triethyl orthoformate and boiled. After evaporation the solid is dissolved in methanol and sodium borohydride at room temperature is added. The desired product is obtained by chromatography on silica gel.

Examples 63 to 68 and 85 describe the processes in accordance with scheme 8 in more detail.

Scheme 9

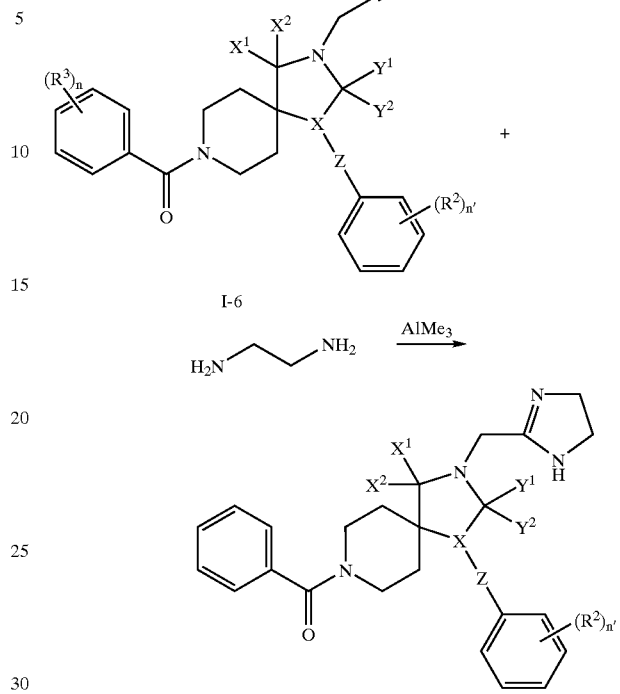

I-7

The definition of substituents is described above.

An ethylenediamine-trimethylaluminium complex is added to a solution of a compound of formula I-6 in toluene. The reaction is carried out at about 120°.

Examples 69 has been described in accordance with scheme 9.

Scheme 10 (intermediates)

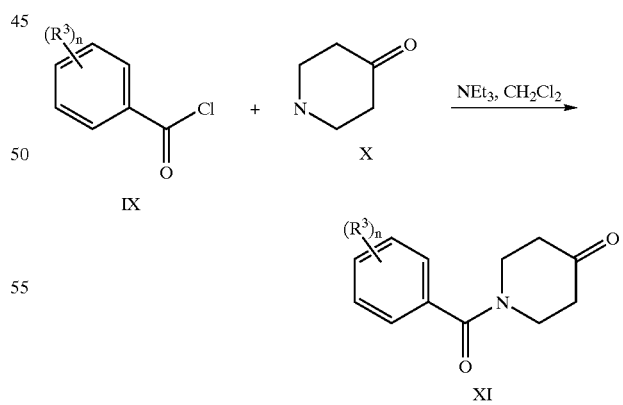

XI

The definition of substituents is described above.

A solution of a compound of formula IX in dichloromethane is added with cooling to a solution of 4-piperidone trifluoroacetate and triethylamine. The reaction is carried out at room temperature.

Example A describes this process in more detail.

Scheme 11 (intermeditates)

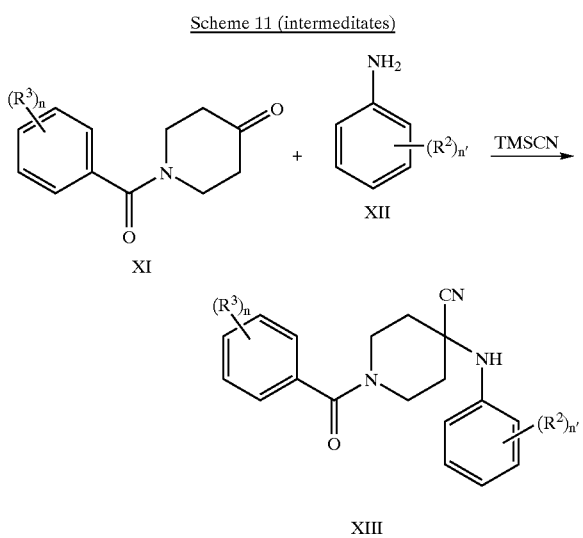

The definition of substituents is described above.

To a solution of a compound of formula XI in acetic acid is added with cooling a compound of formula XII, for example 3-chloroaniline, and TMSCN.

Examples B, C, D, E, F, G and H are prepared in accordance with scheme 11.

Scheme 12

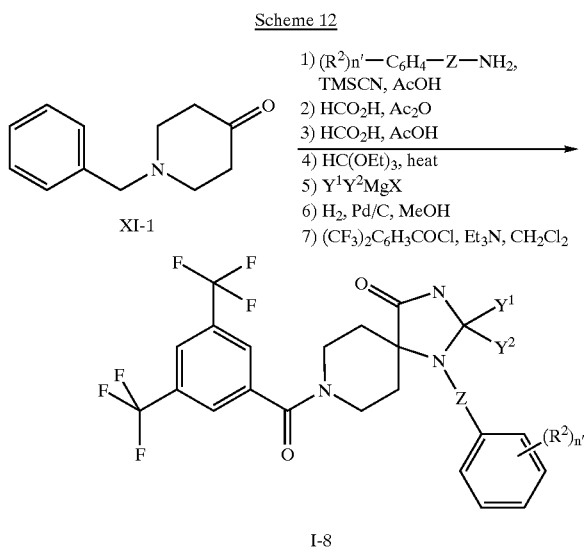

The definition of substituents is described above.

In accordance with scheme 12 to a solution of 1-benzyl-piperidin-4-one (XI-1) in acetic acid is added a compound of the formula $(R^2)_{n'}$—$C_6H_4$—Z—$NH_2$, for example aniline, and TMSCN. To a solution of the intermediate amino nitrile in formic acid is added with cooling acetic anhydride and the obtained foam is dissolved in formic acid and acetic acid. The intermediate is cyclized by boiling in triethylorthoformate and subsequently treated with a Grignard reagent, for example with methylmagnesium bromide. The intermediate is treated with hydrogen and palladium on charcoal in methanol. The last step is the treatment of the obtained solution with 3,5-bis-trifluoromethyl benzoylchloride to obtain a compound of formula I-8.

Examples 91 to 109, 112, 114 to 120 and 132 describe the processes in accordance with scheme 12 in more detail.

Scheme 13

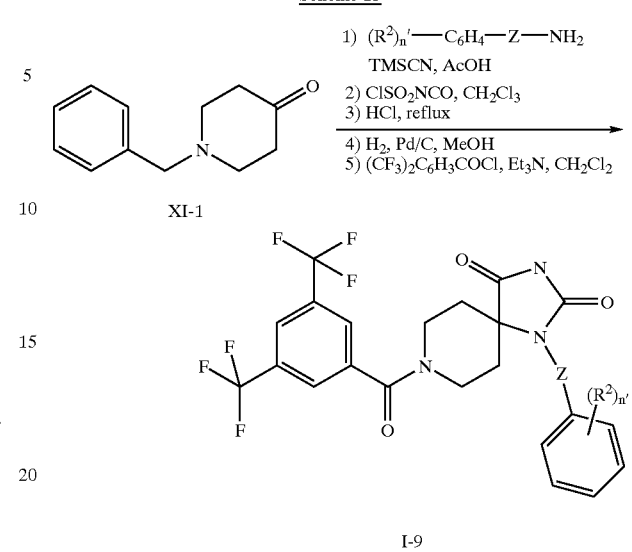

The definition of substituents is described above.

To a solution of the compound of formula XI-1 in acetic acid a compound of formula $(R^2)_{n'}$—$C_6H_4$—Z—$NH_2$, for example aniline, and TMSCN are added. Then, to a solution of the intermediate amino nitrile, chlorosulfonyl isocyanate is added. The solid is suspended in hydrochloric acid and refluxed. The intermediate is treated with hydrogen and palladium on charcoal. The last step is the treatment with $(CF_3)_2C_6H_3COCl$ to give a compound of formula I-9.

Examples 110, 111 and 113 are described in more detail in accordance with scheme 13.

Scheme 14

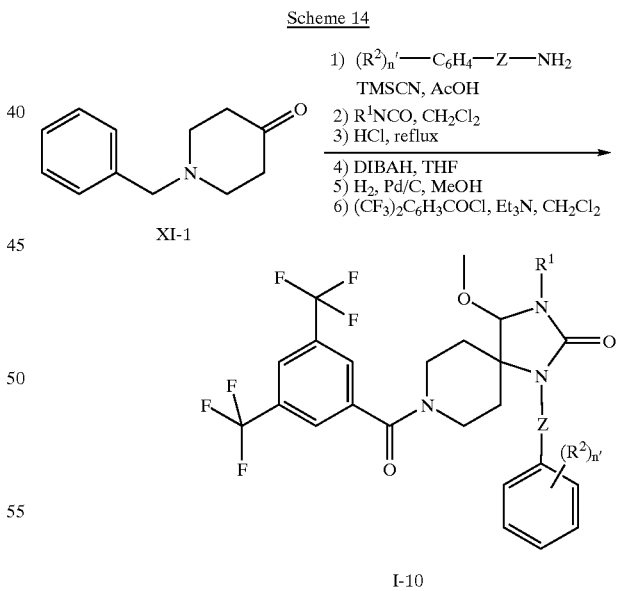

The definition of substituents is described above.

To a solution of 1-benzyl-piperidin-4-one (XI-1) in acetic acid is added a compound of formula $(R^2)_{n'}$—$C_6H_4$—Z—$NH_2$, for example aniline, and TMSCN. To a solution of the obtained intermediate amino nitrile in dichloromethane is added chlorosulfonyl isocyanate. The obtained white solid is suspended in HCl and refluxed. The reduction is then performed with diisobutyl aluminium hydride. The intermediate n-benzyl protected spiropiperidine is treated with hydrogen and palladium on charcoal. After stirring in a hydrogen atmosphere at room temperature $(CF_3)_2C_6H_3COCl$ is added to give a compound of formula I-10.

Examples 129 and 130 are described in accordance with scheme 14.

Scheme 15

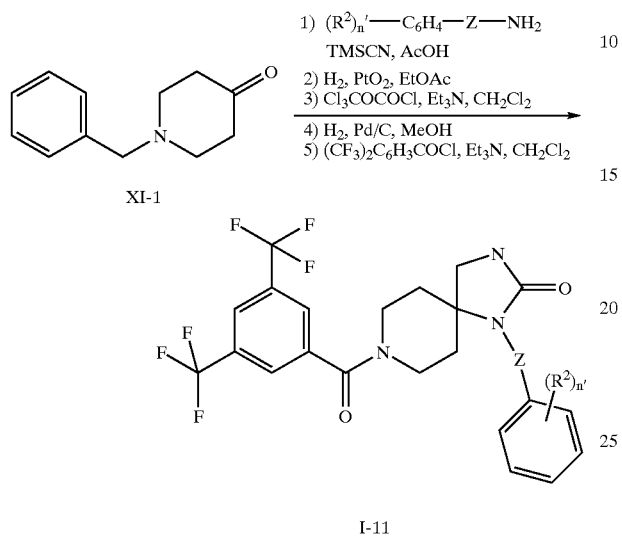

I-11

The definition of substituents is described above.

To a solution of 1-benzyl-piperidin-4-one (XI-1) in acetic acid is added a compound of formula $(R^2)_{n'}$—$C_6H_4$—Z—$NH_2$, for example o-toluidine, and TMSCN. The solution of the obtained intermediate amino nitrile is dissolved in acetic acid $PtO_2$, and the reaction mixture is hydrogenated at room temperature. To the solution of the obtained intermediate in dichloromethane and triethylamine is added trichloromethyl chloroformat at about −20° C. The obtained intermediate N-benzyl protected spiropiperidine is treated with hydrogen and palladium on charcoal. After stirring in a hydrogen atmosphere at room temperature $(CF_3)_2C_6H_3COCl$ is added to give a compound of formula I-11.

Example 131 is prepared in accordance with scheme 15.

Scheme 16

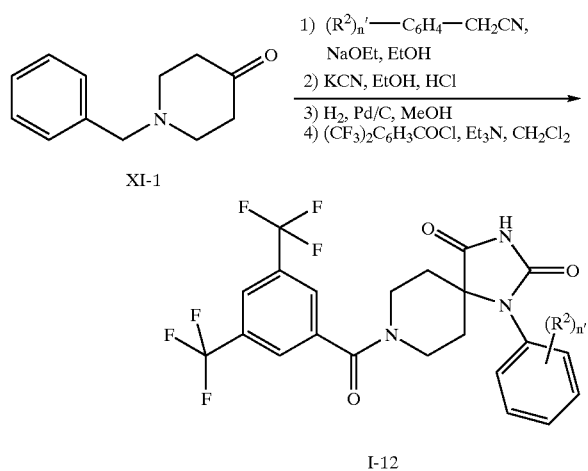

I-12

To a solution sodium ethoxide is added benzyl cyanide and N-benzyl-4-piperidone (XI-1) and the reaction is run at 85° C. for 3 h. Workup with concentrated hydrochloric gives the intermediate (1-benzyl-piperidin-4-ylidene)-phenyl-acetonitrile which is treated with potassium cyanide. The obtained intermediate N-benzyl protected spiropiperidine is treated with hydrogen and palladium on charcoal. After stirring in a hydrogen atmosphere at room temperature $(CF_3)_2C_6H_3COCl$ is added to give a compound of formula I-12.

Example 156 is prepared in accordance with scheme 16.

Scheme 17

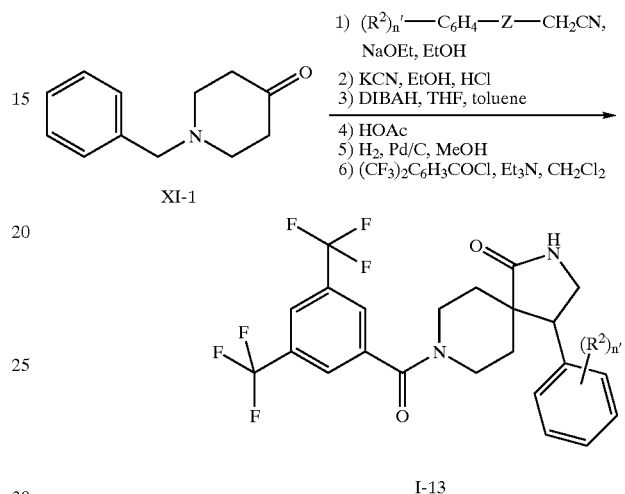

I-13

The definition of substituents is described above.

To a solution sodium ethoxide is added benzyl cyanide and N-benzyl-4-piperidone (XI-1) and the reaction is run at 85° C. for 3 h. Workup with concentrated hydrochloric gives the intermediate (1-benzyl-piperidin-4-yl-idene)-phenyl-acetonitrile which is treated with potassium cyanide. Reduction of one carbonyl group is performed with an excess of diisobutylaluminium hydride and elimination is performed with acetic acid. The obtained intermediate N-benzyl protected spiropiperidine is treated with hydrogen and palladium on charcoal. After stirring in a hydrogen atmosphere at room temperature $(CF_3)_2C_6H_3COCl$ is added to give a compound of formula I-13.

Example 161 is prepared in accordance with scheme 17.

As mentioned earlier, the compounds of formula I and their pharmaceutically usable addition salts possess valuable pharmacological properties. It has been found that all of the compounds of formula I of the present invention are antagonists of the Neurokinin 1 (NK-1, substance P) receptor.

The compounds were investigated in accordance with the tests given hereinafter.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 µg/ml), $MnCl_2$ (3 mM) and phosphoramidon (2 µM). Binding assays consisted of 250 µl of membrane suspension ($1.25 \times 10^5$ cells/assay tube), 0.125 µl of buffer of displacing agent and 125 µl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%)

with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the range of 6.5–8.8 for all of the exemplified compounds of the present invention. Particular examples of such compounds are

| Example No. | pKi |
|---|---|
| 6 | 8.66 |
| 26 | 7.47 |
| 39 | 7.03 |
| 45 | 8.29 |
| 58 | 8.08 |
| 70 | 8.37 |
| 91 | 8.12 |
| 137 | 8.34 |
| 170 | 7.96 |
| 176 | 8.12 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. All temperatures are given in degrees Celsius.

EXAMPLE 1

8-(3,5-Bis-trifluoromethyl-benzoyl)-1-phenyl-1,3,8-triaza-spiro[4.5]decan-4-one

A solution of 3,5-bis(trifluoromethyl)benzoyl chloride (2.3 mL, 13 mmol) in dichloromethane (50 mL) was added with stirring to a mixture of 1-phenyl-1,3,8-triaza-spiro[4.5]decan-4-one (2.9 g, 13 mmol) and triethylamine (3.5 mL, 25 mmol) in dichloromethane (250 mL) at room temperature. Stirring was continued for 2 h. Water (150 mL) was added, the phases were separated and the water phase was extracted twice with dichloromethane (100 mL). Organic phases were pooled, washed with brine (200 mL), dried with $Na_2SO_4$ and the solvent was evaporated. Chromatography on silica gel (ethylacetate/n-hexane 1:1) yielded the desired product (5.3 g, 89%) m.p. 251° C. and MS: m/e=472.1 (M+H$^+$).

EXAMPLE 2

1-Phenyl-8-(3,4,5-trimethoxy-benzoyl)-1,3,8-triaza-spiro[4.5]decan-4-one

The title compound, MS: m/e=426.4 (M+H$^+$), was prepared in accordance with the general method of example 1 from 3,4,5-trimethoxybenzoyl chloride and 1-phenyl-1,3,8-triaza-spiro[4.5]decan-4-one.

EXAMPLE 3

8-(3-Fluoro-5-trifluoromethyl-benzoyl)-1-phenyl-1,3,8-triaza-spiro[4.5]decan-4-one The title compound, MS: m/e=422.3 (M+H$^+$), was prepared in accordance with the general method of example 1 from 3-fluoro-5-(trifluoromethyl)benzoyl chloride and 1-phenyl-1,3,8-triaza-spiro[4.5]decan-4-one.

EXAMPLE 4

8-(3,5-Bis-trifluoromethyl-benzoyl)-3-(2-morpholin-4-yl-ethyl)-1-phenyl-1,3,8-triaza-spiro[4.5]decan-4-one Sodium hydride (34 mg, 60%) was suspended in N-methyl-2-pyrrolidone (2 mL) and 8-(3,5-bis-trifluoromethyl-benzoyl)-1-phenyl-1,3,8-triaza-spiro[4.5]decan-4-one (200 mg) was added with stirring. After 5 minutes stirring at room temperature 4-(2-chloroethyl) morpholine hydrochloride (79 mg) was added. The mixture was heated to 100° C. with stirring and kept for 1 h at that temperature. After cooling, saturated sodium bicarbonate solution was added and the mixture was extracted with ethylacetate. Organic phases were pooled, dried with $Na_2SO_4$ and the solvent was evaporated. Chromatography on silica gel (ethylacetate) yielded the desired product (180 mg, 73%), MS: m/e=585.1 (M+H$^+$).

EXAMPLE 5

8-(3,5-Bis-trifluoromethyl-benzoyl)-1-phenyl-3-pyridin-3-yl-methyl-1,3,8-triaza-spiro[4.5]decan-4-one The title compound, MS: m/e=563.3 (M+H$^+$), was prepared in accordance with the general method of example 4 from 8-(3,5-bis-trifluoromethyl-benzoyl)-1-phenyl-1,3,8-triaza-spiro[4.5]decan-4-one and 3-(chloromethyl)pyridine hydrochloride in 1,2-dimethoxyethane as solvent.

EXAMPLE 6

8-(3,5-Bis-trifluoromethyl-benzoyl)-3-(4,6-dimethoxy-[1,3,5]triazin-2-yl)-1-phenyl-1,3,8-triaza-spiro[4.5]decan-4-one The title compound, MS: m/e=611.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloro-4,6-dimethoxy-1,3,5-triazine in 1,2-dimethoxyethane as solvent.

EXAMPLE 7

8-(3,5-Bis-trifluoromethyl-benzoyl)-1-phenyl-3-(2-piperidin-1-yl-ethyl)-1,3,8-triaza-spiro[4.5]decan-4-one The title compound, MS: m/e=583.2 (M+H$^+$), was prepared in accordance with the general method of example 4 from 8-(3,5-bis-trifluoromethyl-benzoyl)-1-phenyl-1,3,8-triaza-spiro[4.5]decan-4-one and 1-(2-chloroethyl)piperidine hydrochloride.

EXAMPLE 8

8-(3,5-Bis-trifluoromethyl-benzoyl)-1-phenyl-3-(2-pyrrolidin-1-yl-ethyl)-1,3,8-triaza-spiro[4.5]decan-4-one The title compound, MS: m/e=569.2 (M+H$^+$), was prepared in accordance with the general method of example 4 from 8-(3,5-bis-trifluoromethyl-benzoyl)-1-phenyl-1,3,8-triaza-spiro[4.5]decan-4-one and 1-(2-chloroethyl)pyrrolidine hydrochloride.

EXAMPLE 9

2-[8-(3,5-Bis-trifluoromethyl-benzoyl)-4-oxo-1-phenyl-1,3,8-triaza-spiro[4.5]dec-3-yl]-acetamide The title compound, MS: m/e=529.2 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-bromoacetamide in 1,2-dimethoxyethane as solvent.

EXAMPLE 10

2-[8-(3,5-Bis-trifluoromethyl-benzoyl)-4-oxo-1-phenyl-1,3,8-triaza-spiro[4.5]dec-3-yl]-N,N-dimethyl-acetamide The title compound, MS: m/e=557.2 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chlor-N,N-dimethyacetamide in 1,2-dimethoxyethane as solvent.

EXAMPLE 11

8-(3,5-Bis-trifluoromethyl-benzoyl)-4-oxo-1-phenyl-1,3,8-triaza-spiro[4.5]dec-3-yl]-acetic acid methyl ester The title compound, MS: m/e=544.2 (M+H$^+$), was prepared in accordance with the general method of example 4 from 8-(3,5-bis-trifluoromethyl-benzoyl)-1-phenyl-1,3,8-triaza-spiro[4.5]decan-4-one and methyl bromoacetate in 1,2-dimethoxyethane as solvent.

EXAMPLE 12

8-(3,5-Bis-trifluoromethyl-benzoyl)-3-methoxymethyl-1-phenyl-1,3,8-triaza-spiro[4.5]decan-4-one The title compound, MS: m/e=516.2 (M+H$^+$), was prepared in accordance with the general method of example 4 from 8-(3,5-bis-trifluoromethyl-benzoyl)-1-phenyl-1,3,8-triaza-spiro[4.5]decan-4-one and bromomethyl methylether in 1,2-dimethoxyethane as solvent.

EXAMPLE 13

2-[8-(3,5-Bis-trifluoromethyl-benzoyl)-4-oxo-1-phenyl-1,3,8-triaza-spiro[4.5]dec-3-yl]-malonic acid dimethyl ester The title compound, MS: m/e=602.0 (M+H$^+$), was prepared in accordance with the general method of example 4 from 8-(3,5-bis-trifluoromethyl-benzoyl)-1-phenyl-1,3,8-triaza-spiro[4.5]decan-4-one and dimethyl bromomalonate in 1,2-dimethoxyethane as solvent.

EXAMPLE 14

(R,S)-8-(3,5-Bis-trifluoromethyl-benzoyl)-3-(2-hydroxy-3-phenoxy-propyl)-1-phenyl-1,3,8-triaza-spiro[4.5]decan-4-one The title compound, MS: m/e=622.1 (M+H$^+$), was prepared in accordance with the general method of example 4 from 8-(3,5-bis-trifluoromethyl-benzoyl)-1-phenyl-1,3,8-triaza-spiro[4.5]decan-4-one and phenylglycidylether in 1,2-dimethoxyethane as solvent.

EXAMPLE 15

8-(3,5-Bis-trifluoromethyl-benzoyl)-3-(4,6-dichloro-pyrimidin-2-yl)-1-phenyl-1,3,8-triaza-spiro[4.5]decan-4-one The title compound, MS: m/e=618.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,4,6-trichlorpyrimidine in 1,2-dimethoxyethane as solvent.

EXAMPLE 16

8-(3,5-Bis-trifluoromethyl-benzoyl)-1-phenyl-3-(5-trifluoromethyl-pyridin-2-yl)-1,3,8-triaza-spiro[4.5]decan-4-one The title compound, MS: m/e=617.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloro-5-(trifluoromethyl)pyridine in 1,2-dimethoxyethane as solvent.

EXAMPLE 17

(R,S)-8-(3,5-Bis-trifluoromethyl-benzoyl)-1-phenyl-3-(3,3,3-trifluoro-2-hydroxy-propyl)-1,3,8-triaza-spiro[4.5]decan-4-one The title compound, MS: m/e=584.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 3-bromo-1,1,1-trifluoro-2-propanole.

EXAMPLE 18

8-(3,5-Bis-trifluoromethyl-benzoyl)-1-phenyl-3-pyridin-2-yl-methyl-1,3,8-triaza-spiro[4.5]decan-4-one The title compound, MS: m/e=563.3 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-picolylchloride hydrochloride in 1,2-dimethoxyethane as solvent.

EXAMPLE 19

8-(3,5-Bis-trifluoromethyl-benzoyl)-1-phenyl-3-pyridin-4-yl-methyl-1,3,8-triaza-spiro[4.5]decan-4-one The title compound, MS: m/e=563.3 (M+H$^+$), was prepared in accordance with the general method of example 4 from 8-(3,5-bis-trifluoromethyl-benzoyl)-1-phenyl-1,3,8-triaza-spiro[4.5]decan-4-one and 4-chloromethylpyridine hydrochloride in 1,2-dimethoxyethane as solvent.

EXAMPLE 20

8-(3,5-Bis-trifluoromethyl-benzoyl)-3-(4-chloro-pyrimidin-2-yl)-1-phenyl-1,3,8-triaza-spiro[4.5]decan-4-one The title compound, MS: m/e=584.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,4-dichloropyrimidine in 1,2-dimethoxyethane as solvent.

EXAMPLE 21

8-(3,5-Bis-trifluoromethyl-benzoyl)-3-(4-chloro-6-methyl-pyrimidin-2-yl)-1-phenyl-1,3,8-triaza-spiro[4.5]decan-4-one The title compound, MS: m/e=598.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,4-dichloro-6-methylpyrimidine in 1,2-dimethoxyethane as solvent.

EXAMPLE 22

8-(3,5-Bis-trifluoromethyl-benzoyl)-3-(3-hydroxy-propyl)-1-phenyl-1,3,8-triaza-spiro[4.5]decan-4-one The title compound, MS: m/e=530.2 (M+H$^+$), was prepared in accordance with the general method of example 4 from 8-(3,5-bis-trifluoromethyl-benzoyl)-1-phenyl-1,3,8-triaza-spiro[4.5]decan-4-one and (3-bromopropoxy)-tert.-butyldimethylsilane in 1,2-dimethoxyethane as solvent. HCl in ethanol (3% conc.) cleaved the intermediate TBDMS-ether.

EXAMPLE 23

8-(3,5-Bis-trifluoromethyl-benzoyl)-3-(2-hydroxy-ethyl)-1-o-tolyl-1,3,8-triaza-spiro[4.5]decan-4-one The title compound, MS: m/e=530.2 (M+H$^+$), was prepared in accordance with the general method of example 4 from 8-(3,5-bis-trifluoromethyl-benzoyl)-1-o-tolyl-1,3,8-triaza-spiro[4.5]decan-4-one and (3-bromoethoxy)-tert.-butyldimethylsilane. HCl in ethanol (3% conc.) cleaved the intermediate TBDMS-ether.

EXAMPLE 24

8-(3,5-Bis-trifluoromethyl-benzoyl)-3-(2-hydroxy-ethyl)-1-phenyl-1,3,8-triaza-spiro[4.5]decan-4-one The title compound, MS: m/e=516.2 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloroethoxytrimethylsilane in 1,2-dimethoxyethane as solvent. Silicagel chromatography cleaved the intermediate TMS-ether.

EXAMPLE 25

8-(3,5-Bis-trifluoromethyl-benzoyl)-1-phenyl-3-pyrimidin-2-yl-1,3,8-triaza-spiro[4.5]decan-4-one The title compound, MS: m/e=550.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloropyrimidine.

EXAMPLE 26

8-(3,5-Bis-trifluoromethyl-benzoyl)-3-(3,5-dichloro-pyridin-2-yl)-1-phenyl-1,3,8-triaza-spiro[4.5]decan-4-one The title compound, MS: m/e=617.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,3,5-trichloropyridine in 1,2-dimethoxyethane as solvent.

EXAMPLE 27

2-[8-(3,5-Bis-trifluoromethyl-benzoyl)-4-oxo-1-phenyl-1,3,8-triaza-spiro[4.5]dec-3-yl]-6-methyl-nicotinonitrile The title compound, MS: m/e=588.2 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloro-3-cyanopyridine in 1,2-dimethoxyethane as solvent.

EXAMPLE 28

8-(3,5-Bis-trifluoromethyl-benzoyl)-3-(3-chloro-5-trifluoromethyl-pyridin-2-yl)-1-phenyl-1,3,8-triaza-spiro[4.5]decan-4-one The title compound, MS: m/e=651.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,3-dichloro-5-(trifluoromethyl)pyridine in 1,2-dimethoxyethane as solvent.

EXAMPLE 29

8-(3,5-Bis-trifluoromethyl-benzoyl)-3-(5-ethyl-pyrimidin-2-yl)-1-phenyl-1,3,8-triaza-spiro[4.5]decan-4-one The title compound, MS: m/e=578.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloro-5-ethylpyrimidine in 1,2-dimethoxyethane as solvent.

EXAMPLE 30

8-(3,5-Bis-trifluoromethyl-benzoyl)-1-phenyl-3-(4-trifluoromethyl-pyrimidin-2-yl)-1,3,8-triaza-spiro[4.5]decan-4-one The title compound, MS: m/e=618.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloro-4-(trifluoromethyl)pyrimidine in 1,2-dimethoxyethane as solvent.

EXAMPLE 31

8-(3,5-Bis-trifluoromethyl-benzoyl)-3-(3-chloro-pyrazin-2-yl)-1-phenyl-1,3,8-triaza-spiro[4.5]decan-4-one The title compound, MS: m/e=584.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,3-dichloropyrazine in 1,2-dimethoxyethane as solvent.

EXAMPLE 32

8-(3,5-Bis-trifluoromethyl-benzoyl)-4-oxo-1-phenyl-1,3,8-triaza-spiro[4.5]dec-3-yl]-acetic acid ethyl ester The title compound, MS: m/e=558.2 (M+H$^+$), was prepared in accordance with the general method of example 4 from 8-(3,5-bis-trifluoromethyl-benzoyl)-1-phenyl-1,3,8-triaza-spiro[4.5]decan-4-one and ethyl bromoacetate in 1,2-dimethoxyethane as solvent.

EXAMPLE 33

8-(3,5-Bis-trifluoromethyl-benzoyl)-3-(3-chloro-quinoxalin-2-yl)-1-phenyl-1,3,8-triaza-spiro[4.5]decan-4-one The title compound, MS: m/e=634.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,3-dichloroquinoxaline in 1,2-dimethoxyethane as solvent.

EXAMPLE 34

8-(3,5-Bis-trifluoromethyl-benzoyl)-3-(6-chloro-pyrazin-2-yl)-1-phenyl-1,3,8-triaza-spiro[4.5]decan-4-one The title compound, MS: m/e=584.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2,6-dichloropyrazine in 1,2-dimethoxyethane as solvent.

EXAMPLE 35

8-(3,5-Bis-trifluoromethyl-benzoyl)-1-phenyl-3-pyrazin-2-yl-1,3,8-triaza-spiro[4.5]decan-4-one The title compound, MS: m/e=550.1 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloropyrazine in 1,2-dimethoxyethane as solvent.

EXAMPLE 36

8-(3,5-Bis-trifluoromethyl-benzoyl)-4-oxo-1-phenyl-1,3,8-triaza-spiro[4.5]dec-3-yl]-acetonitrile The title compound, MS: m/e=510.1 (M$^+$), was prepared in accordance with the general method of example 4 from 8-(3,5-bis-trifluoromethyl-benzoyl)-1-phenyl-1,3,8-triaza-spiro[4.5]decan-4-one and bromoacetonitrile in 1,2-dimethoxyethane as solvent.

EXAMPLE 37

8-(3,5-Bis-trifluoromethyl-benzoyl)-3-(4,6-dimethoxy-pyrimidin-2-yl)-1-phenyl-1,3,8-triaza-spiro[4.5]decan-4-one The title compound, MS: m/e=610.0 (M+H$^+$), was prepared in accordance with the general method of example 4 from 8-(3,5-bis-trifluoromethyl-benzoyl)-1-phenyl-1,3,8-triaza-spiro[4.5]decan-4-one and 2-chloro-4,6-dimethoxypyrimidine.

EXAMPLE 38

(S)-8-(3,5-Bis-trifluoromethyl-benzoyl)-1-phenyl-3-(4,4,4-trifluoro-3-hydroxy-butyl)-1,3,8-triaza-spiro[4.5]decan-4-one The title compound, MS: m/e=598.0 (M+H$^+$), was prepared in accordance with the general method of example 4 from 8-(3,5-bis-trifluoromethyl-benzoyl)-1-phenyl-1,3,8-triaza-spiro[4.5]decan-4-one and toluene-4-sulfonic acid (S)-4,4,4-trifluoro-3-hydroxy-butyl ester in 1,2-dimethoxyethane as solvent.

EXAMPLE 39

8-(3,5-Bis-trifluoromethyl-benzoyl)-1-(3,4-dichloro-phenyl)-3-(4,6-dimethoxy-[1,3,5]triazin-2-yl)-1,3,8-triaza-spiro[4.5]decan-4-one The title compound, MS: m/e=679.0 (M+H$^+$), was prepared in accordance with the general method of example 4 from 8-(3,5-bis-trifluoromethyl-benzoyl)-1-(3,4-dichloro-phenyl)-1,3,8-triaza-spiro[4.5]decan-4-one and 2-chloro-4,6-dimethoxy-1,3,5-triazine in 1,2-dimethoxyethane as solvent.

EXAMPLE 40

8-(3,5-Bis-trifluoromethyl-benzoyl)-1-(3-chloro-phenyl)-3-(4,6-dimethoxy-[1,3,5]triazin-2-yl)-1,3,8-triaza-spiro[4.5]decan-4-one The title compound, MS: m/e=645.1 (M+H$^+$), was prepared in accordance with the general method of example 4 from 8-(3,5-bis-trifluoromethyl-benzoyl)-1-(3-chloro-phenyl)-1,3,8-triaza-spiro[4.5]decan-4-one and 2-chloro-4,6-dimethoxy-1,3,5-triazine in 1,2-dimethoxyethane as solvent.

EXAMPLE 41

8-(3,5-Bis-trifluoromethyl-benzoyl)-3-(4,6-dimethoxy-[1,3,5]triazin-2-yl)-1-o-tolyl-1,3,8-triaza-spiro[4.5]decan-4-one The title compound, MS: m/e=625.1 (M+H$^+$), was prepared in accordance with the general method of example 4 from 8-(3,5-bis-trifluoromethyl-benzoyl)-1-o-tolyl-1,3,8-triaza-spiro[4.5]decan-4-one and 2-chloro-4,6-dimethoxy-1,3,5-triazine in 1,2-dimethoxyethane as solvent.

EXAMPLE 42

8-(3,5-Bis-trifluoromethyl-benzoyl)-1-(2-chloro-phenyl)-3-(4,6-dimethoxy-[1,3,5]triazin-2-yl)-1,3,8-triaza-spiro[4.5]decan-4-one The title compound, MS: m/e=645.0 (M+H$^+$), was prepared in accordance with the general method of example 4 from 8-(3,5-bis-trifluoromethyl-benzoyl)-1-(2-chloro-phenyl)-1,3,8-triaza-spiro[4.5]decan-4-one and 2-chloro-4,6-dimethoxy-1,3,5-triazine in 1,2-dimethoxyethane as solvent.

EXAMPLE 43

8-(3,5-Bis-trifluoromethyl-benzoyl)-1-(4-chloro-phenyl)-3-(4,6-dimethoxy-[1,3,5]triazin-2-yl)-1,3,8-triaza-spiro[4.5]decan-4-one The title compound, MS: m/e=645.1 (M+H$^+$), was prepared in accordance with the general method of example 4 from 8-(3,5-bis-trifluoromethyl-benzoyl)-1-(4-chloro-phenyl)-1,3,8-triaza-spiro[4.5]decan-4-one and 2-chloro-4,6-dimethoxy-1,3,5-triazine in 1,2-dimethoxyethane as solvent.

EXAMPLE 44

8-(3,5-Bis-trifluoromethyl-benzoyl)-1-(2-chloro-phenyl)-3-pyridin-3-yl-methyl-1,3,8-triaza-spiro[4.5]decan-4-one The title compound, MS: m/e=597.0 (M+H$^+$), was prepared in accordance with the general method of example 4 from 8-(3,5-bis-trifluoromethyl-benzoyl)-1-(2-chloro-phenyl)-1,3,8-triaza-spiro[4.5]decan-4-one and 3-(chloromethyl)pyridine hydrochloride in 1,2-dimethoxyethane as solvent.

EXAMPLE 45

8-(3,5-Bis-trifluoromethyl-benzoyl)-3-pyridin-3-yl-methyl-1-o-tolyl-1,3,8-triaza-spiro[4.5]decan-4-one The title compound, MS: m/e=577.0 (M+H$^+$), was prepared in accordance with the general method of example 4 from 8-(3,5-bis-trifluoromethyl-benzoyl)-1-o-tolyl-1,3,8-triaza-spiro[4.5]decan-4-one and 3-(chloromethyl)pyridine hydrochloride in 1,2-dimethoxyethane as solvent.

EXAMPLE 46

8-(3,5-Bis-trifluoromethyl-benzoyl)-1-(2-methoxy-phenyl)-3-pyridin-3-yl-methyl-1,3,8-triaza-spiro[4.5]decan-4-one The title compound, MS: m/e=592.1 (M$^+$), was prepared in accordance with the general method of example 4 from 8-(3,5-bis-trifluoromethyl-benzoyl)-1-(2-methoxy-phenyl)-1,3,8-triaza-spiro[4.5]decan-4-one and 3-(chloromethyl)pyridine hydrochloride in 1,2-dimethoxyethane as solvent.

EXAMPLE 47

8-(3,5-Bis-trifluoromethyl-benzoyl)-3-(4,6-dimethoxy-[1,3,5]triazin-2-yl)-1-(2-methoxy-phenyl)-1,3,8-triaza-spiro[4.5]decan-4-one The title compound, MS: m/e=640.2 (M$^+$), was prepared in accordance with the general method of example 4 from 8-(3,5-bis-trifluoromethyl-benzoyl)-1-(2-methoxy-phenyl)-1,3,8-triaza-spiro[4.5]decan-4-one and 2-chloro-4,6-dimethoxy-1,3,5-triazine in 1,2-dimethoxyethane as solvent.

EXAMPLE 48

8-(3,5-Bis-trifluoromethyl-benzoyl)-3-(3-imidazol-1-yl-propyl)-1-phenyl-1,3,8-triaza-spiro[4.5]decan-4-one A solution of 8-(3,5-bis-trifluoromethyl-benzoyl)-3-(3-hydroxy-propyl)-1-phenyl-1,3,8-triaza-spiro[4.5]decan-4-one (128 mg, 0.25 mmol) and triethylamine (35 µL, 0.27 mmol) in dichloromethane (2 mL) was cooled to 0° C. A solution of methanesulfonyl chloride (19 µL, 0.25 mmol) in dichloromethane (0.5 mL) was added and the mixture was stirred for 4 h at 0° C. Sodium bicarbonate (saturated solution, 2.5 mL) was added, the phases were separated, the organic phase was dried with Na$_2$SO$_4$ and the solvent was evaporated. Chromatography on silica gel (ethylacetate/n-hexane 1:1) yielded the intermediate mesylate. The mesylate was dissolved in dimethylformamide (6 mL), sodium bicarbonate (70 mg, 0.74 mmol) and imidazole (26 mg, 0.37 mmol) was added and the mixture stirred for 2 d at 80° C. Filtration and evaporation of the solvent yielded a residue which was purified by chromatography on silica gel (CH$_2$Cl$_2$/MeOH 9:1) to yield the desired product (23 mg, 16%), MS: m/e=580.1 (M+H$^+$).

EXAMPLE 49

8-(3,5-Bis-trifluoromethyl-benzoyl)-3-(3-isopropylamino-propyl)-1-phenyl-1,3,8-triaza-spiro[4.5]decan-4-one The title compound, MS: m/e=571.1 (M+H$^+$), was prepared in accordance with the general method of example 48 from 8-(3,5-bis-trifluoromethyl-benzoyl)-3-(3-hydroxy-propyl)-1-phenyl-1,3,8-triaza-spiro[4.5]decan-4-one and isopropylamine.

EXAMPLE 50

8-(3,5-Bis-trifluoromethyl-benzoyl)-3-[3-(4-methyl-piperazin-1-yl)-propyl]-1-phenyl-1,3,8-triaza-spiro[4.5]decan-4-one The title compound, MS: m/e=612.2 (M+H$^+$), was prepared in accordance with the general method of example 48 from 8-(3,5-bis-trifluoromethyl-benzoyl)-3-(3-hydroxy-propyl)-1-phenyl-1,3,8-triaza-spiro[4.5]decan-4-one and 1-methylpiperazine.

EXAMPLE 51

8-(3,5-Bis-trifluoromethyl-benzoyl)-3-(3-dimethylamino-propyl)-1-phenyl-1,3,8-triaza-spiro[4.5]decan-4-one The title compound, MS: m/e=557.2 (M+H$^+$), was prepared in accordance with the general method of example 48 from 8-(3,5-bis-trifluoromethyl-benzoyl)-3-(3-hydroxy-propyl)-1-phenyl-1,3,8-triaza-spiro[4.5]decan-4-one and dimethylamine.

EXAMPLE 52

8-(3,5-Bis-trifluoromethyl-benzoyl)-3-(2-imidazol-1-yl-ethyl)-1-phenyl-1,3,8-triaza-spiro[4.5]decan-4-one The title compound, MS: m/e=566.2 (M+H$^+$), was prepared in accordance with the general method of example 49 from 8-(3,5-bis-trifluoromethyl-benzoyl)-3-(2-hydroxy-ethyl)-1-phenyl-1,3,8-triaza-spiro[4.5]decan-4-one and imidazole.

EXAMPLE 53

8-(3,5-Bis-trifluoromethyl-benzoyl)-3-(2-isopropylamino-ethyl)-1-phenyl-1,3,8-triaza-spiro[4.5]decan-4-one The title compound, MS: m/e=557.2 (M+H$^+$), was prepared in accordance with the general method of example 48 from 8-(3,5-bis-trifluoromethyl-benzoyl)-3-(2-hydroxy-ethyl)-1-phenyl-1,3,8-triaza-spiro[4.5]decan-4-one and isopropylamine.

EXAMPLE 54

8-(3,5-Bis-trifluoromethyl-benzoyl)-3-[2-(4-methyl-piperazin-1-yl)-ethyl]-1-phenyl-1,3,8-triaza-spiro[4.5]decan-4-one The title compound, MS: m/e=598.1 (M+H$^+$), was prepared in accordance with the general method of example 48 from 8-(3,5-bis-trifluoromethyl-benzoyl)-3-(2-hydroxy-ethyl)-1-phenyl-1,3,8-triaza-spiro[4.5]decan-4-one and 1-methylpiperazine.

EXAMPLE 55

8-(3,5-Bis-trifluoromethyl-benzoyl)-3-(2-dimethylamino-ethyl)-1-phenyl-1,3,8-triaza-spiro[4.5]decan-4-one The title compound, MS: m/e=543.2 (M+H$^+$), was prepared in accordance with the general method of example 48 from 8-(3,5-bis-trifluoromethyl-benzoyl)-3-(2-hydroxy-ethyl)-1-phenyl-1,3,8-triaza-spiro[4.5]decan-4-one and dimethylamine.

EXAMPLE 56

8-(3,5-Bis-trifluoromethyl-benzoyl)-3-(2-dimethylamino-ethyl)-1-o-tolyl-1,3,8-triaza-spiro[4.5]decan-4-one The title compound, MS: m/e=557.2 (M+H$^+$), was prepared in accordance with the general method of example 48 from 8-(3,5-bis-trifluoromethyl-benzoyl)-3-(2-hydroxy-ethyl)-1-o-tolyl-1,3,8-triaza-spiro[4.5]decan-4-one and dimethylamine.

EXAMPLE 57

8-(3,5-Bis-trifluoromethyl-benzoyl)-3-(2-isopropylamino-ethyl)-1-o-tolyl-1,3,8-triaza-spiro[4.5]decan-4-one The title compound, MS: m/e=571.1 (M+H$^+$), was prepared in accordance with the general method of example 48 from 8-(3,5-bis-trifluoromethyl-benzoyl)-3-(2-hydroxy-ethyl)-1-o-tolyl-1,3,8-triaza-spiro[4.5]decan-4-one and isopropylamine.

EXAMPLE 58

8-(3,5-Bis-trifluoromethyl-benzoyl)-3-(2-pyrrolidin-1-yl-ethyl)-1-o-tolyl-1,3,8-triaza-spiro[4.5]decan-4-one The title compound, MS: m/e=583.2 (M+H$^+$), was prepared in accordance with the general method of example 48 from 8-(3,5-bis-trifluoromethyl-benzoyl)-3-(2-hydroxy-ethyl)-1-o-tolyl-1,3,8-triaza-spiro[4.5]decan-4-one and pyrrolidine.

EXAMPLE 59

3-[8-(3,5-Bis-trifluoromethyl-benzoyl)-4-oxo-1-phenyl-1,3,8-triaza-spiro[4.5]dec-3-yl]-propionic acid ethyl ester To a mixture of 8-(3,5-bis-trifluoromethyl-benzoyl)-1-phenyl-1,3,8-triaza-spiro[4.5]decan-4-one (1.0 g, 2.1 mmol), cesium fluoride (32 mg, 0.21 mmol) and tetraethoxysilane (475 μL, 2.1 mmol) in THF (10 mL) was added ethyl acrylate (254 μL, 2.3 mmol). The mixture was stirred for 1 d at room temperature. Evaporation of the solvent yielded a residue which was purified by chromatography on silica gel (ethyl acetate/n-hexane 1:2) to yield the desired product (0.9 g, 75%), MS: m/e=572.1 (M+H$^+$).

EXAMPLE 60

3-[8-(3,5-Bis-trifluoromethyl-benzoyl)-4-oxo-1-phenyl-1,3,8-triaza-spiro[4.5]dec-3-yl]-propionic acid methyl ester The title compound, MS: m/e=558.2 (M+H$^+$), was prepared in accordance with the general method of example 59 from 8-(3,5-bis-trifluoromethyl-benzoyl)-1-phenyl-1,3,8-triaza-spiro[4.5]decan-4-one and methyl acrylate.

EXAMPLE 61

8-(3,5-Bis-trifluoromethyl-benzoyl)-3-(6-chloro-pyrimidin-4-yl)-1-phenyl-1,3,8-triaza-spiro[4.5]decan-4-one A mixture of 8-(3,5-bis-trifluoromethyl-benzoyl)-1-phenyl-1,3,8-triaza-spiro[4.5]decan-4-one (0.1 g, 0.21 mmol), potassium carbonate (59 mg, 0.42 mmol), CuCl (2 mg, 0.021 mmol), tris[2-(2-methoxyethoxy)-ethyl]-amine (1.5 μL) and 4,6-dichloropyrimidine (32 mg, 0.21 mmol) in xylene (5 mL) was stirred and boiled for 18 h. The mixture was cooled, washed with water, ammonia in water (10%) and water again. Evaporation of the solvent yielded a residue which was purified by chromatography on silica gel (ethyl acetate/n-hexane 1:2) to yield the desired product (29 mg, 24%), m.p. 212–214° C. and MS: m/e=584.1 (M+H$^+$).

EXAMPLE 62

8-(3,5-Bis-trifluoromethyl-benzoyl)-1-phenyl-3-pyridin-4-yl-1,3,8-triaza-spiro[4.5]decan-4-one A mixture of 8-(3,5-bis-trifluoromethyl-benzoyl)-1-phenyl-1,3,8-triaza-spiro[4.5]decan-4-one (0.1 g, 0.21 mmol), 4-pyridylboronic acid (52 mg, 0.42 mmol), cupric acetate (58 mg, 0.32 mmol) and triethylamine (60 μL, 0.42 mmol) in dichloromethane (2 mL) was stirred for 2 d at room temperature. Chromatography on silica gel (ethyl acetate) yielded the desired product (26 mg, 21%), MS: m/e=549.1 (M+H$^+$).

EXAMPLE 63

8-(3,5-Bis-trifluoromethyl-benzoyl)-1-(3-chloro-phenyl)-1,3,8-triaza-spiro[4.5]decan-4-one To a solution of 1-(3,5-bis-trifluoromethyl-benzoyl)-4-(3-chloro-phenylamino)-piperidine-4-carbonitrile (6.2 g, 13 mmol) in formic acid (80 mL) was added with cooling acetic anhydride (80 mL). Stirring continued for 2 h at room temperature. Evaporation of the solvent yielded 7.2 g white foam, which was used without further purification in the next step.

The solid was dissolved in formic acid (74 mL) and acetic acid was added (7.4 mL). The solution was stirred at room temperature over night. The solvents were evaporated, saturated sodium bicarbonate solution (150 mL) was added and the mixture was extracted with ethylacetate. The organic phases were pooled, dried with Na$_2$SO$_4$ and the solvent was evaporated. The residue was a white foam (7.5 g), which was used without further purification in the next step.

The solid was dissolved in triethyl orthoformate (320 mL) and boiled for a week. After cooling the solvent was evaporated to yield 8.5 g brownish foam which was used without further purification in the next step.

The solid was dissolved in methanol (300 mL), sodium borohydride (1.03 g, 27 mmol) was added to the solution and the mixture was stirred for 1 h at room temperature and for 1 h at 60° C. After cooling the solvent was evaporated, the residue was dissolved in dichloromethane (250 mL) and washed with ice cold ammonia (12%). The phases were separated, the water phase was extracted with dichloromethane, and organic phases were pooled and dried with $MgSO_4$. Evaporation yielded 8.1 g light brown residue. Chromatography on silica gel (dichloromethane/methanol 50:1) yielded the desired product (2.7 g, 41%), m.p. 235–236° C. and MS: m/e=506.2 ($M+H^+$).

EXAMPLE 64

8-(3,5-Bis-trifluoromethyl-benzoyl)-1-(4-chloro-phenyl)-1,3,8-triaza-spiro[4.5]decan-4-one The title compound, m.p. 233–235° C. and MS: m/e=506.2 ($M+H^+$), was prepared in accordance with the general method of example 63 from 1-(3,5-bis-trifluoromethyl-benzoyl)-4-(4-chloro-phenylamino)-piperidine-4-carbonitrile.

EXAMPLE 65

8-(3,5-Bis-trifluoromethyl-benzoyl)-1-(3,4-dichloro-phenyl)-1,3,8-triaza-spiro[4.5]decan-4-one The title compound, m.p. 220–222° C. and MS: m/e=540.1 ($M+H^+$), was prepared in accordance with the general method of example 63 from 1-(3,5-bis-trifluoromethyl-benzoyl)-4-(3,4-dichloro-phenylamino)-piperidine-4-carbonitrile.

EXAMPLE 66

8-(3,5-Bis-trifluoromethyl-benzoyl)-1-o-tolyl-1,3,8-triaza-spiro[4.5]decan-4-one The title compound, m.p. 164–168° C. and MS: m/e=486.3 ($M+H^+$), was prepared in accordance with the general method of example 63 from 1-(3,5-bis-trifluoromethyl-benzoyl)-4-o-tolylamino-piperidine-4-carbonitrile.

EXAMPLE 67

8-(3,5-Bis-trifluoromethyl-benzoyl)-1-(2-chloro-phenyl)-1,3,8-triaza-spiro[4.5]decan-4-one The title compound, m.p. 157–159° C. and MS: m/e=506.2 ($M+H^+$), was prepared in accordance with the general method of example 63 from 1-(3,5-bis-trifluoromethyl-benzoyl)-4-(2-chloro-phenylamino)-piperidine-4-carbonitrile.

EXAMPLE 68

8-(3,5-Bis-trifluoromethyl-benzoyl)-1-(2-methoxy-phenyl)-1,3,8-triaza-spiro[4.5]decan-4-one The title compound, MS: m/e=502.2 ($M+H^+$), was prepared in accordance with the general method of example 63 from 1-(3,5-bis-trifluoromethyl-benzoyl)-4-(2-methoxy-phenylamino)-piperidine-4-carbonitrile.

EXAMPLE 69

8-(3,5-Bis-trifluoromethyl-benzoyl)-3-(4,5-dihydro-1H-imidazol-2-yl-methyl)-1-phenyl-1,3,8-triaza-spiro[4.5]decan-4-one Ethylenediamine-trimethylaluminium complex (0.8 mmol) was added to a solution of [8-(3,5-bis-trifluoromethyl-benzoyl)-4-oxo-1-phenyl-1,3,8-triaza-spiro[4.5]dec-3-yl]-acetonitrile (0.2 g, 0.4 mmol) in toluene (1.5 mL) and heated to 120° C. for 18 h. Chromatography on silica gel (dichloromethane/methanol 9:1) yielded the desired product (14 mg, 6%), MS: m/e=554.2 ($M+H^+$).

EXAMPLE 70

8-(3,5-Bis-trifluoromethyl-benzoyl)-1-(2-chloro-phenyl)-3-methyl-1,3,8-triaza-spiro[4.5]decan-4-one 8-(3,5-Bis-trifluoromethyl-benzoyl)-1-(2-chloro-phenyl)-1,3,8-triaza-spiro[4.5]decan-4-one (253 mg) was suspended in 1,2-dimethoxyethane (3 mL) and sodium hydride (24 mg, 60%) was added with stirring at room temperature. After 15 minutes methyliodide (78 mg) was added and stirring was continued overnight at room temperature. Water was added and the mixture was extracted with ethylacetate. Organic phases were pooled, dried with $Na_2SO_4$ and the solvent was evaporated. Chromatography on silica gel (hexane/ethylacetate=1:1) yielded the desired product (152 mg, 59%), MS: m/e=520.1 ($M+H^+$).

EXAMPLE 71

3-(1-Benzyl-1H-imidazol-2-ylmethyl)-8-(3,5-bis-trifluoromethyl-benzoyl)-1-(2-chloro-phenyl)-1,3,8-triaza-spiro[4.5]decan-4-one 8-(3,5-Bis-trifluoromethyl-benzoyl)-1-(2-chloro-phenyl)-1,3,8-triaza-spiro[4.5]decan-4-one (253 mg) was suspended in 1,2-dimethoxyethane (3 mL) and sodium hydride (24 mg, 60%) was added with stirring at room temperature. After 15 minutes 1-benzyl-(2-chloromethyl)-imidazole (121 mg) was added and stirring was continued overnight at 80° C. After cooling down to room temperature water was added and the mixture was extracted with ethylacetate. Organic phases were pooled, dried with $Na_2SO_4$ and the solvent was evaporated. Chromatography on silica gel (hexane/ethylacetate=1:1) yielded the desired product (215 mg, 64%), MS: m/e=676.0 ($M+H^+$).

EXAMPLE 72

8-(3,5-Bis-trifluoromethyl-benzoyl)-1-(2-chloro-phenyl)-3-(2-oxo-oxazolidin-5-ylmethyl)-1,3,8-triaza-spiro[4.5]decan-4-one The title compound, MS: m/e=604.9 ($M+H^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 5-chloromethyl-2-oxazolidinone.

EXAMPLE 73

8-(3,5-Bis-trifluoromethyl-benzoyl)-1-(2-chloro-phenyl)-3-(2-dimethylamino-ethyl)-1,3,8-triaza-spiro[4.5]decan-4-one The title compound, MS: m/e=577.0 ($M+H^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 1-chloro-2-dimethylaminoethane hydrochloride.

EXAMPLE 74

8-(3,5-Bis-trifluoromethyl-benzoyl)-1-(2-chloro-phenyl)-3-(2-pyrrolidin-1-yl-ethyl)-1,3,8-triaza-spiro[4.5]decan-4-one The title compound, MS: m/e=603.0 ($M+H^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 1-(2-chloroethyl)-pyrrolidine hydrochloride.

EXAMPLE 75

8-(3,5-Bis-trifluoromethyl-benzoyl)-1-(2-chloro-phenyl)-3-(2-methyl-thiazol-4-ylmethyl)-1,3,8-triaza-spiro[4.5]decan-4-one The title compound, MS: m/e=617.0 (M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 4-chloromethyl-2-methylthiazole hydrochloride.

EXAMPLE 76

8-(3,5-Bis-trifluoromethyl-benzoyl)-1-(2-chloro-phenyl)-3-(6-chloro-pyrimidin-4-yl)-1,3,8-triaza-spiro[4.5]decan-4-one The title compound, MS: m/e=618.0 (100, M+H$^+$), 620.0 (80, M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 4,6-dichloropyrimidine.

EXAMPLE 77

8-(3,5-Bis-trifluoromethyl-benzoyl)-1-(2-chloro-phenyl)-3-(3,5-dichloro-pyridin-2-yl -1,3,8-triaza-spiro[4.5]decan-4-one The title compound, MS: m/e=652.9 (100, M+H$^+$), 654.9 (100, M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 2,3,5-trichloropyridine.

EXAMPLE 78

8-(3,5-Bis-trifluoromethyl-benzoyl)-1-(2-chloro-phenyl)-3-(4-trifluoromethyl-pyrimidin-2-yl)-1,3,8-triaza-spiro[4.5]decan-4-one The title compound, MS: m/e=651.9 (M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 2-chloro-4-(trifluoromethyl)-pyrimidine.

EXAMPLE 79

8-(3,5-Bis-trifluoromethyl-benzoyl)-1-(2-chloro-phenyl)-3-pyrimidin-2-yl-1,3,8-triaza-spiro[4.5]decan-4-one The title compound, MS: m/e=584.0 (M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 2-chloro-pyrimidine.

EXAMPLE 80

2-[8-(3,5-Bis-trifluoromethyl-benzoyl)-1-(2-chloro-phenyl)-4-oxo-1,3,8-triaza-spiro[4.5]dec-3-yl]-N,N-dimethyl-acetamide The title compound, MS: m/e=591.0 (M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 2-chloro-N,N-dimethylacetamide.

EXAMPLE 81

8-(3,5-Bis-trifluoromethyl-benzoyl)-1-(2-chloro-phenyl)-3-(3-dimethylamino-propyl)-1,3,8-triaza-spiro[4.5]decan-4-one The title compound, MS: m/e=591.1 (M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 3-dimethylaminopropylchloride hydrochloride.

EXAMPLE 82

8-(3,5-Bis-trifluoromethyl-benzoyl)-1-(2-chloro-phenyl)-3-(3,5-dimethyl-isoxazol-4-yl-methyl)-1,3,8-triaza-spiro[4.5]decan-4-one The title compound, MS: m/e=615.1 (M+H$^+$), was prepared in accordance with the general method of example 71 from 8-(3,5-bis-trifluoromethyl-benzoyl)-1-(2-chloro-phenyl)-1,3,8-triaza-spiro[4.5]decan-4-one and 4-(chloromethyl)-3,5-dimethylisoxazole.

EXAMPLE 83

8-(3,5-Bis-trifluoromethyl-benzoyl)-1-(2-chloro-phenyl)-3-pyridin-3-yl-1,3,8-triaza-spiro[4.5]decan-4-one 8-(3,5-Bis-trifluoromethyl-benzoyl)-1-(2-chloro-phenyl)-1,3,8-triaza-spiro[4.5]decan-4-one (253 mg) was dissolved in dichloromethane (5 mL), 3-pyridineboronic acid (246 mg), triethylamine (101 mg) and copper(II)-acetate (136 mg) were added. The mixture was stirred at room temperature overnight. The solvent was evaporated and the residue was purified by chromatography on silica gel (hexane/ethylacetate=2:1) to yield the desired product (120 mg, 41%), MS: m/e=583.0 (M+H$^+$).

EXAMPLE 84

8-(3,5-Bis-trifluoromethyl-benzoyl)-1-(2-chloro-phenyl)-3-pyridin-4-yl-1,3,8-triaza-spiro[4.5]decan-4-one The title compound, MS: m/e=583.0 (M+H$^+$), was prepared in accordance with the general method of example 83 from 8-(3,5-bis-trifluoromethyl-benzoyl)-1-(2-chloro-phenyl)-1,3,8-triaza-spiro[4.5]decan-4-one and 4-pyridineboronic acid.

EXAMPLE 85

1-Benzyl-8-(3,5-bis-trifluoromethyl-benzoyl)-1,3,8-triaza-spiro[4.5]decan-4-one

The title compound, MS: m/e=486.3 (M+H$^+$) was prepared in accordance with the general method of example 63 from 4-benzylamino-1-(3,5-bis-trifluoromethyl-benzoyl)-piperidine-4-carbonitrile.

EXAMPLE 86

1-Benzyl-8-(3,5-bis-trifluoromethyl-benzoyl)-3-methyl-1,3,8-triaza-spiro[4.5]decan-4-one The title compound, MS: m/e=500.3 (M+H$^+$), was prepared in accordance with the general method of example 71 from 1-benzyl-8-(3,5-bis-trifluoromethyl-benzoyl)-1,3,8-triaza-spiro[4.5]decan-4-one and methyliodide.

EXAMPLE 87

1-Benzyl-8-(3,5-bis-trifluoromethyl-benzoyl)-3-(2-pyrrolidin-1-yl-ethyl)-1,3,8-triaza-spiro[4.5]decan-4-one hydrochloride The title compound, MS: m/e=583.2 (M+H$^+$), was prepared in accordance with the general method of example 71 from 1-benzyl-8-(3,5-bis-trifluoromethyl-benzoyl)-1,3,8-triaza-spiro[4.5]decan-4-one and 1-(2-chloroethyl)-pyrrolidine.

EXAMPLE 88

8-(3,5-Bis-trifluoromethyl-benzoyl)-1-(2-chloro-benzyl)-1,3,8-triaza-spiro[4.5]decan-4-one 1-Benzyl-8-(3,5-bis-trifluoromethyl-benzoyl)-1,3,8-triaza-spiro[4.5]decan-4-one (292 mg) was dissolved in methanol (5 mL) and palladium on charcoal (10%, 78 mg) was added. After stirring in a hydrogen atmosphere (1 bar) at room temperature for 30 min the mixture was filtered over celite and the solvent was evaporated.

The residue was dissolved in 1,2-dichloroethane (5 ml), 2-chlorobenzaldehyde (71 mg), acetic acid (300 mg) and sodium triacetoxyborohydride (148 mg) were added. The reaction mixture was stirred overnight at room temperature. Water was added, the organic layer was separated and dried. The solvent was evaporated and the residue was purified by chromatography on silica gel (ethylacetate) to yield the desired product (160 mg, 62%), MS: m/e=520.1 (M+H$^+$).

EXAMPLE 89

8-(3,5-Bis-trifluoromethyl-benzoyl)-1-(3-chloro-benzyl)-3-methyl-1,3,8-triaza-spiro[4.5]decan-4-one The title compound, MS: m/e=534.2 (M+H$^+$), was prepared in accordance with the general method of example 88 from 1-benzyl-8-(3,5-bis-trifluoromethyl-benzoyl)-3-methyl-1,3,8-triaza-spiro[4.5]decan-4-one and 3-chlorobenzaldehyde.

EXAMPLE 90

1-Benzoyl-8-(3,5-bis-trifluoromethyl-benzoyl)-1,3,8-triaza-spiro[4.5]decan-4-one 1-Benzyl-8-(3,5-bis-trifluoromethyl-benzoyl)-1,3,8-triaza-spiro[4.5]decan-4-one (50 mg) was dissolved in methanol (2 mL) and palladium on charcoal (10%, 13 mg) was added. After stirring in a hydrogen atmosphere (1 bar) at room temperature for 30 min the mixture was filtered over celite and the solvent was evaporated.

The residue was dissolved in dichloromethane (2 ml), triethylamine (22 mg) was added and the mixture was cooled to 0° C. Benzoylchloride (14 mg) was added and the mixture was stirred for 1 h at this temperature. Water was added, the organic layer was separated and dried. The solvent was evaporated and the residue was purified by chromatography on silica gel (ethylacetate) to yield the desired product (30 mg, 60%), MS: m/e=500.2 (M+H$^+$).

EXAMPLE 91

(rac)-8-(3,5-Bis-trifluoromethyl-benzoyl)-2-methyl-1-phenyl-1,3,8-triaza-spiro[4.5]decan-4-one To a solution of 1-benzyl-piperidin-4-one (18.9 g, 100 mmol) in acetic acid (150 mL) were added at 0° C. aniline (10.2 g, 110 mmol) and trimethylsilylcyanide (12.5 mL, 100 mmol). The suspension was stirred for 22 h at room temperature. The reaction mixture was than added to ice-water (350 mL) and ammonia was added until pH 9. After that the mixture was extracted with dichloromethane, the organic phases were pooled, washed with brine and dried with MgSO$_4$. The solvent was evaporated and the residue crystallized from diethylether to yield the intermediate amino nitrile (19.2 g, 66%).

To a solution of the intermediate amino nitrile (16.0 g, 55 mmol) in formic acid (210 mL) was added with cooling acetic anhydride (210 mL). Stirring continued for 2.5 h at room temperature. Evaporation of the solvent yielded a white foam, which was used without further purification in the next step.

The foam was dissolved in formic acid (210 mL) and acetic acid was added (21 mL). The solution was stirred at room temperature over night. The solvents were evaporated, saturated sodium bicarbonate solution (300 mL) was added and the mixture was extracted with dichloromethane. The organic phases were pooled, dried with Na$_2$SO$_4$ and the solvent was evaporated. The residue was a white foam (18.2 g), which was used without further purification in the next step.

The solid was dissolved in triethyl orthoformate (500 mL) and boiled for a week. After cooling the solvent was evaporated to yield 18.5 g brownish foam which was used without further purification in the next step.

The brown foam (7.68 g, 24 mmol) was dissolved in THF (80 mL) and was slowly added at room temperature to methylmagnesium bromide (24 mL 3M in diethylether, 72 mmol) and stirred at room temperature overnight. The reaction mixture was quenched with saturated ammonium chloride (100 mL) and extracted with ethyl acetate. Organic phases were pooled and dried with MgSO$_4$. Evaporation yielded 7.64 g light brown residue. Chromatography on silica gel (hexane, ethyl acetate, triethyl amine 40:20:1) yielded the intermediate n-benzyl protected piperidine(3.7 g, 46%).

The intermediate (3.7 g, 11 mmol) was dissolved in methanol (125 mL) and palladium on charcoal (10%, 1.25 g) was added. After stirring in a hydrogen atmosphere (1 bar) at room temperature overnight the mixture was filtered and the solvent was evaporated.

The residue was dissolved in dichloromethane (200 ml), triethyl amine (2.1 mL, 15 mmol) and 3,5-bistrifluoromethyl benzoylchloride (1.8 mL, 10 mmol) were added and the mixture was stirred at room temperature overnight. Water was added, the organic layer was separated and dried. The solvent was evaporated and the residue was purified by chromatography on silica gel (hexane, ethyl acetate, triethyl amine 20:10:1) to yield the desired product (4.17 g, 86%), MS: m/e=486.3 (M+H$^+$).

EXAMPLE 92

(rac)-8-(3,5-Bis-trifluoromethyl-benzoyl)-2-phenethyl-1-phenyl-1,3,8-triaza-spiro[4.5]decan-4-one The title compound, MS: m/e=576.0 (M+H$^+$), was prepared in accordance with the general method of example 91 from 1-benzyl-piperidin-4-one, aniline and phenethyl magnesium chloride.

EXAMPLE 93

(rac)-8-(3,5-Bis-trifluoromethyl-benzoyl)-2-isopropyl-1-phenyl-1,3,8-triaza-spiro[4.5]decan-4-one The title compound, MS: m/e=514.3 (M+H$^+$), was prepared in accordance with the general method of example 91 from 1-benzyl-piperidin-4-one, aniline and isopropyl magnesium chloride.

EXAMPLE 94

(rac)-2-Benzyl-8-(3,5-bis-trifluoromethyl-benzoyl)-1-phenyl-1,3,8-triaza-spiro[4.5]decan-4-one The title compound, MS: m/e=562.2 (M+H$^+$), was prepared in accordance with the general method of example 91 from 1-benzyl-piperidin-4-one, aniline and benzyl magnesium chloride.

EXAMPLE 95

(rac)-8-(3,5-Bis-trifluoromethyl-benzoyl)-1,2-diphenyl-1,3,8-triaza-spiro[4.5]decan-4-one The title compound, MS: m/e=548.1 (M+H$^+$), was prepared in accordance with the general method of example 91 from 1-benzyl-piperidin-4-one, aniline and phenyl magnesium chloride.

EXAMPLE 96

(rac)-8-(3,5-Bis-trifluoromethyl-benzoyl)-2-methyl-1-o-tolyl-1,3,8-triaza-spiro[4.5]decan-4-one The title compound, MS: m/e=500.2 (M+H$^+$), was prepared in accordance with the general method of example 91 from 1-benzyl-piperidin-4-one, 1-methyl aniline and methyl magnesium bromide.

EXAMPLE 97

(rac)-2-Benzyl-8-(3,5-bis-trifluoromethyl-benzoyl)-1-o-tolyl-1,3,8-triaza-spiro[4.5]decan-4-one The title compound, MS: m/e=576.0 (M+H$^+$), was prepared in accordance with the general method of example 91 from 1-benzyl-piperidin-4-one, 1-methyl aniline and benzyl magnesium chloride.

EXAMPLE 98

(rac)-8-(3,5-Bis-trifluoromethyl-benzoyl)-2-phenyl-1-o-tolyl-1,3,8-triaza-spiro[4.5]decan-4-one The title compound, MS: m/e=562.3 (M+H$^+$), was prepared in accordance with the general method of example 91 from 1-benzyl-piperidin-4-one, 1-methyl aniline and phenyl magnesium chloride.

EXAMPLE 99

(rac)-8-(3,5-Bis-trifluoromethyl-benzoyl)-2-methyl-1-phenyl-3-pyridin-3-yl-methyl-1,3,8-triaza-spiro[4.5]decan-4-one (rac)-8-(3,5-Bis-trifluoromethyl-benzoyl)-2-methyl-1-phenyl-1,3,8-triaza-spiro[4.5]decan-4-one (200 mg, 0.41 mmol) was dissolved in dimethyl formamide (10 mL) and sodium hydride (40 mg, 60% in mineral oil, 1 mmol) and 3-chloromethyl pyridinium chloride (82 mg, 0.5 mmol) were added and stirred at room temperature overnight. Water (30 mL) was added and the reaction mixture extacted with ethyl acetate. The organic phases were pooled, dried with MgSO$_4$ and the solvent was evaporated. The residue was purified by chromatography on silica gel (ethyl acetate) to yield the desired product (219 mg, 93%), MS: m/e=577.0 (M+H$^+$).

EXAMPLE 100

(rac)-8-(3,5-Bis-trifluoromethyl-benzoyl)-2,3-dimethyl-1-phenyl-1,3,8-triaza-spiro[4.5]decan-4-one The title compound, MS: m/e=500.2 (M+H$^+$), was prepared in accordance with the general method of example 99 from (rac)-8-(3,5-bis-trifluoromethyl-benzoyl)-2-methyl-1-phenyl-1,3,8-triaza-spiro[4.5]decan-4-one 1-benzyl-piperidin-4-one and methyl iodide.

EXAMPLE 101

(rac)-8-(3,5-Bis-trifluoromethyl-benzoyl)-2-methyl-1-phenyl-3-(2-pyrrolidin-1-yl-ethyl)-1,3,8-triaza-spiro[4.5]decan-4-one The title compound, MS: m/e=583.2 (M+H$^+$), was prepared in accordance with the general method of example 99 from (rac)-8-(3,5-bis-trifluoromethyl-benzoyl)-2-methyl-1-phenyl-1,3,8-triaza-spiro[4.5]decan-4-one 1-benzyl-piperidin-4-one and 1-(2-chloroethyl)pyrrolidine.

EXAMPLE 102

(rac)-8-(3,5-Bis-trifluoromethyl-benzoyl)-2-methyl-3-(2-methyl-thiazol-4-yl-methyl)-1-phenyl-1,3,8-triaza-spiro[4.5]decan-4-one The title compound, MS: m/e=597.0 (M+H$^+$), was prepared in accordance with the general method of example 99 from (rac)-8-(3,5-bis-trifluoromethyl-benzoyl)-2-methyl-1-phenyl-1,3,8-triaza-spiro[4.5]decan-4-one 1-benzyl-piperidin-4-one and 4-chloromethyl-2-methylthiazole.

EXAMPLE 103

(rac)-8-(3,5-Bis-trifluoromethyl-benzoyl)-3-cyclopropylmethyl-2-methyl-1-phenyl-1,3,8-triaza-spiro[4.5]decan-4-one The title compound, MS: m/e=540.3 (M+H$^+$), was prepared in accordance with the general method of example 99 from (rac)-8-(3,5-bis-trifluoromethyl-benzoyl)-2-methyl-1-phenyl-1,3,8-triaza-spiro[4.5]decan-4-one 1-benzyl-piperidin-4-one and cyclopropyl methyl bromide.

EXAMPLE 104

(rac)-8-(3,5-Bis-trifluoromethyl-benzoyl)-3-(3-dimethylamino-propyl)-2-methyl-1-phenyl-1,3,8-triaza-spiro[4.5]decan-4-one The title compound, MS: m/e=571.1 (M+H$^+$), was prepared in accordance with the general method of example 99 from (rac)-8-(3,5-bis-trifluoromethyl-benzoyl)-2-methyl-1-phenyl-1,3,8-triaza-spiro[4.5]decan-4-one 1-benzyl-piperidin-4-one and 3-dimethylamino1-propyl chloride.

EXAMPLE 105

(rac)-8-(3,5-Bis-trifluoromethyl-benzoyl)-2,3-dimethyl-1-o-tolyl-1,3,8-triaza-spiro[4.5]decan-4-one The title compound, MS: m/e=571.1 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and methyl iodide.

EXAMPLE 106

(rac)-8-(3,5-Bis-trifluoromethyl-benzoyl)-2-methyl-3-(2-pyrrolidin-1-yl-ethyl)-1-o-tolyl-1,3,8-triaza-spiro[4.5]decan-4-one The title compound, MS: m/e=597.1 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 1-(2-chloroethyl)-pyrrolidine.

EXAMPLE 107

(rac)-8-(3,5-Bis-trifluoromethyl-benzoyl)-2-methyl-3-(2-piperidin-1-yl-ethyl)-1-o-tolyl-1,3,8-triaza-spiro[4.5]decan-4-one The title compound, MS: m/e=610.3 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 1-(2-chloroethyl)-piperidine.

EXAMPLE 108

(rac)-8-(3,5-Bis-trifluoromethyl-benzoyl)-2-methyl-3-(2-piperazin-1-yl-ethyl)-1-o-tolyl-1,3,8-triaza-spiro[4.5]decan-4-one The title compound, MS: m/e=626.1 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 1-(2-chloroethyl)-piperazine.

EXAMPLE 109

(rac)-8-(3,5-Bis-trifluoromethyl-benzoyl)-2-methyl-1-phenyl-3-pyridin-4-yl-1,3,8-triaza-spiro[4.5]decan-4-one The title compound, MS: m/e=563.2 (M+H$^+$), was prepared in accordance with the general method of example 63 from (rac)-8-(3,5-bis-trifluoromethyl-benzoyl)-2-methyl-1-phenyl-1,3,8-triaza-spiro[4.5]decan-4-one and pyridine-4-boronic acid.

EXAMPLE 110

8-(3,5-Bis-trifluoromethyl-benzoyl)-1-phenyl-1,3,8-triaza-spiro[4.5]decane-2,4-dione To a solution of 1-benzyl-piperidin-4-one (18.9 g, 100 mmol) in acetic acid (150 mL) were added at 0° C. aniline (10.2 g, 110 mmol) and trimethylsilylcyanide (12.5 mL, 100 mmol). The suspension was stirred for 22 h at room temperature. The reaction mixture was than added to ice-water (350 mL) and ammonia was added until pH 9. After that the mixture was extracted with dichloromethane, the organic phases were pooled, washed with brine and dried with MgSO$_4$. The solvent was evaporated and the residue crystallized from diethylether to yield the intermediate amino nitrile (19.2 g, 66%).

To a solution of the intermediate amino nitrile (5.0 g, 17.2 mmol) in dichloromethane(50 mL) was added chlorosulfonyl isocyanate (1.65 mL, 19 mmol). Stirring continued for 1 h at room temperature. Evaporation of the solvent yielded a white solid, which was used without further purification in the next step.

The white solid was suspended in 1N hydrochloric acid (50 mL) and refluxed for 2 h. The pH was adjusted to exactly 7 by adding 15% sodium hydroxide solution and the mixture was than extracted with dichloromethane. Organic phases were pooled and dried with MgSO$_4$. Evaporation yielded 5.4 g of a solid residue. Chromatography on silica gel (hexane, ethyl acetate 1:1) yielded the intermediate n-benzyl protected spiropiperidine(2.6 g, 45%).

The intermediate (500 mg, 1.5 mmol) was dissolved in methanol (30 mL) and palladium on charcoal (10%, 100 mg) and 5 drops of concentrated hydrochloric acid were added. After stirring in a hydrogen atmosphere (1 bar) at room temperature overnight the mixture was filtered and the solvent was evaporated.

The residue was dissolved in dichloromethane (20 ml), triethyl amine (0.63 mL, 4.5 mmol) and 3,5-bistrifluoromethyl benzoylchloride (0.27 mL, 1.5 mmol) were added and the mixture was stirred at room temperature overnight. Water was added, the organic layer was separated and dried. The solvent was evaporated and the residue was purified by chromatography on silica gel (hexane, ethyl acetate 1:1) to yield the desired product (414 mg, 57%), MS: m/e=486.3 (M+H$^+$).

EXAMPLE 111

8-(3,5-Bis-trifluoromethyl-benzoyl)-1-o-tolyl-1,3,8-triaza-spiro[4.5]decane-2,4-dione The title compound, MS: m/e=498.3 (M−H$^+$), was prepared in accordance with the general method of example 110 from 1-benzyl-piperidin-4-one and o-toluidine.

EXAMPLE 112

8-(3,5-Bis-trifluoromethyl-benzoyl)-1-phenyl-3-pyridin-3-yl-methyl-1,3,8-triaza-spiro[4.5]decane-2.4-dione The title compound, MS: m/e=577.0 (M+H$^+$), was prepared in accordance with the general method of example 121 from 8-(3,5-bis-trifluoromethyl-benzoyl)-1-phenyl-1,3,8-triaza-spiro[4.5]decane-2,4-dione and 3-(hydroxymethyl)-pyridine.

EXAMPLE 113

8-(3,5-Bis-trifluoromethyl-benzoyl)-1,3-diphenyl-1,3,8-triaza-spiro[4.5]decane-2,4-dione The title compound, MS: m/e=562.2 (M+H$^+$), was prepared in accordance with the general method of example 110 from 1-benzyl-piperidin-4-one, aniline and phenyl isocyanate.

EXAMPLE 114

8-(3,5-Bis-trifluoromethyl-benzoyl)-3-pyridin-3-yl-methyl-1-o-tolyl-1,3,8-triaza-spiro[4.5]decane-2,4-dione The title compound, MS: m/e=591.1 (M+H$^+$), was prepared in accordance with the general method of example 121 from 8-(3,5-bis-trifluoromethyl-benzoyl)-1-o-tolyl-1,3,8-triaza-spiro[4.5]decane-2,4-dione and 3-(hydroxymethyl)-pyridine.

EXAMPLE 115

8-(3,5-Bis-trifluoromethyl-benzoyl)-3-(2-pyrrolidin-1-yl-ethyl)-1-o-tolyl-1,3,8-triaza-spiro[4.5]decane-2,4-dione The title compound, MS: m/e=597.1 (M+H$^+$), was prepared in accordance with the general method of example 99 from 8-(3,5-bis-trifluoromethyl-benzoyl)-1-o-tolyl-1,3,8-triaza-spiro[4.5]decane-2,4-dione and 1-(2-chloroethyl)-pyrrolidine.

EXAMPLE 116

8-(3,5-Bis-trifluoromethyl-benzoyl)-3-(3,5-dimethyl-isoxazol-4-yl-methyl)-1-o-tolyl-1,3,8-triaza-spiro[4.5]decane-2,4-dione The title compound, MS: m/e=609.0 (M+H$^+$), was prepared in accordance with the general method of example 99 from 8-(3,5-bis-trifluoromethyl-benzoyl)-1-o-tolyl-1,3,8-triaza-spiro[4.5]decane-2,4-dione and 4-(chloromethyl)-3,5-dimethylisoxazole.

EXAMPLE 117

3-(1H-Benzoimidazol-2-yl-methyl)-8-(3,5-bis-trifluoromethyl-benzoyl)-1-o-tolyl-1,3,8-triaza-spiro[4.5]decane-2,4-dione The title compound, MS: m/e=630.0 (M+H$^+$), was prepared in accordance with the general method of example 99 from 8-(3,5-bis-trifluoromethyl-benzoyl)-1-o-tolyl-1,3,8-triaza-spiro[4.5]decane-2,4-dione and 2-(chloromethyl)-benzimidazole.

EXAMPLE 118

8-(3,5-Bis-trifluoromethyl-benzoyl)-3-(2-methyl-thiazol-4-yl-methyl)-1-o-tolyl-1,3,8-triaza-spiro[4.5]decane-2,4-dione The title compound, MS: m/e=611.0 (M+H$^+$), was prepared in accordance with the general method of example 99 from 8-(3,5-bis-trifluoromethyl-benzoyl)-1-o-tolyl-1,3,8-triaza-spiro[4.5]decane-2,4-dione and 4-chloromethyl-2-methylthiazole.

EXAMPLE 119

8-(3,5-Bis-trifluoromethyl-benzoyl)-3-[1,2,4]oxadiazol-3-yl-methyl-1-o-tolyl-1,3,8-triaza-spiro[4.5]decane-2,4-dione The title compound, MS: m/e=581.2 (M$^+$), was prepared in accordance with the general method of example 99 from 8-(3,5-bis-trifluoromethyl-benzoyl)-1-o-tolyl-1,3,8-triaza-spiro[4.5]decane-2,4-dione and 3-(chloromethyl)-1,2,4-oxadiazole.

EXAMPLE 120

8-(3,5-Bis-trifluoromethyl-benzoyl)-3-(2-oxo-oxazolidin-5-yl-methyl)-1-o-tolyl-1,3,8-triaza-spiro[4.5]decane-2,4-dione The title compound, MS: m/e=599.0 (M$^+$), was prepared in accordance with the general method of example 99 from 8-(3,5-bis-trifluoromethyl-benzoyl)-1-o-tolyl-1,3,8-triaza-spiro[4.5]decane-2,4-dione and 5-chloromethyl-2-oxazolidinone.

EXAMPLE 121

8-(3,5-Bis-trifluoromethyl-benzoyl)-3-furan-2-yl-methyl-1-phenyl-1,3,8-triaza-spiro[4.5]decane-2,4-dione 8-(3,5-Bis-trifluoromethyl-benzoyl)-1-phenyl-1,3,8-triaza-spiro[4.5]decane-2,4-dione (200 mg, 0.41 mmol) was dissolved in dry dioxane (10 mL) and triphenylphosphin (145 mg, 0.54 mmol), furfuryl alcohol (53.1 mg, 0.54 mmol) and diethylazodicarboxylate (40% in toluene, 0.54 mmol) were added sequentially and stirred at room temperature overnight. The solvent was evaporated and the residue was purified by chromatography on silica gel (dichloromethane) to yield the desired product (143 mg, 61%), MS: m/e=566.1 (M+H$^+$).

EXAMPLE 122

8-(3,5-Bis-trifluoromethyl-benzoyl)-3-furan-3-yl-methyl-1-phenyl-1,3,8-triaza-spiro[4.5]decane-2,4-dione The title compound, MS: m/e=566.1 (M$^+$), was prepared in accordance with the general method of example 121 from 8-(3,5-bis-trifluoromethyl-benzoyl)-1-phenyl-1,3,8-triaza-spiro[4.5]decane-2,4-dione and 3-furane methanol.

EXAMPLE 123

(S)-8-(3,5-Bis-trifluoromethyl-benzoyl)-3-(5-oxo-pyrrolidin-2-yl-methyl)-1-phenyl-1,3,8-triaza-spiro[4.5]decane-2,4-dione The title compound, MS: m/e=583.1 (M$^+$), was prepared in accordance with the general method of example 121 from 8-(3,5-bis-trifluoromethyl-benzoyl)-1-phenyl-1,3,8-triaza-spiro[4.5]decane-2,4-dione and (S)-5-(hydroxymethyl)-2-pyrrolidinone.

EXAMPLE 124

8-(3,5-Bis-trifluoromethyl-benzoyl)-3-(5-methyl-isoxazol-3-yl-methyl)-1-o-tolyl-1,3,8-triaza-spiro[4.5]decane-2,4-dione The title compound, MS: m/e=595.0 (M$^+$), was prepared in accordance with the general method of example 121 from 8-(3,5-bis-trifluoromethyl-benzoyl)-1-o-tolyl-1,3,8-triaza-spiro[4.5]decane-2,4-dione and 5-methylisoxazole-3-methanol.

EXAMPLE 125

8-(3,5-Bis-trifluoromethyl-benzoyl)-3-furan-3-yl-ethyl-1-o-tolyl-1,3,8-triaza-spiro[4.5]decane-2,4-dione The title compound, MS: m/e=580.1 (M$^+$), was prepared in accordance with the general method of example 121 from 8-(3,5-bis-trifluoromethyl-benzoyl)-1-o-tolyl-1,3,8-triaza-spiro[4.5]decane-2,4-dione and 3-furane-methanol.

EXAMPLE 126

8-(3,5-Bis-trifluoromethyl-benzoyl)-3-furan-2-yl-methyl-1-o-tolyl-1,3,8-triaza-spiro[4.5]decane-2,4-dione The title compound, MS: m/e=580.0 (M$^+$), was prepared in accordance with the general method of example 121 from 8-(3,5-bis-trifluoromethyl-benzoyl)-1-o-tolyl-1,3,8-triaza-spiro[4.5]decane-2,4-dione and furfuryl alcohol.

EXAMPLE 127

8-(3,5-Bis-trifluoromethyl-benzoyl)-3-thiophen-2-yl-methyl-1-o-tolyl-1,3,8-triaza-spiro[4.5]decane-2,4-dione The title compound, MS: m/e=596.0 (M$^+$), was prepared in accordance with the general method of example 121 from 8-(3,5-bis-trifluoromethyl-benzoyl)-1-o-tolyl-1,3,8-triaza-spiro[4.5]decane-2,4-dione and 2-thiophene methanol.

EXAMPLE 128

8-(3,5-Bis-trifluoromethyl-benzoyl)-3-(2-morpholin-4-yl-ethyl)-1-o-tolyl-1,3,8-triaza-spiro[4.5]decane-2.4-dione The title compound, MS: m/e=613.1 (M$^+$), was prepared in accordance with the general method of example 121 from 8-(3,5-bis-trifluoromethyl-benzoyl)-1-o-tolyl-1,3,8-triaza-spiro[4.5]decane-2,4-dione and N-(2-hydroxyethyl) morpholine.

EXAMPLE 129

8-(3,5-Bis-trifluoromethyl-benzoyl)-4-hydroxy-1,3-diphenyl-1,3,8-triaza-spiro[4.5]decan-2-one To a solution of 1-benzyl-piperidin-4-one (18.9 g, 100 mmol) in acetic acid (150 mL) were added at 0° C. aniline (10.2 g, 110 mmol) and trimethylsilylcyanide (12.5 mL, 100 mmol). The suspension was stirred for 22 h at room temperature. The reaction mixture was than added to ice-water (350 mL) and ammonia was added until pH 9. After that the mixture was extracted with dichloromethane, the organic phases were pooled, washed with brine and dried with MgSO$_4$. The solvent was evaporated and the residue crystallized from diethylether to yield the intermediate amino nitrile (19.2 g, 66%).

To a solution of the intermediate amino nitrile (5.0 g, 17.2 mmol) in dichloromethane(50 mL) was added phenyl isocyanate (2.20 mL, 20 mmol). Stirring continued for 1 h at room temperature. Evaporation of the solvent yielded a white solid, which was used without further purification in the next step.

The white solid was suspended in 1N hydrochloric acid (50 mL) and refluxed for 2 h. The pH was adjusted to exactly 7 by adding 15% sodium hydroxide solution and the mixture was than extracted with dichloromethane. Organic phases were pooled, dried with MgSO$_4$ and evaporated. Chromatography on silica gel (hexane, ethyl acetate 1:1) yielded the intermediate n-benzyl protected spiropiperidine(5.54 g, 78%). The n-benzyl protected spiropiperidine (4.0 g, 9.7 mmol) was dissolved in tetrahydrofuran (50 ml) and diisobutyl aluminium hydride (24 mL, 1M in THF) were added at 0° C. The reaction mixture was stirred at room temperature overnight and the solvent was evaporated. Chromatography of the residue on silica gel (hexane, ethyl acetate, triethyl amine 40:10:1) gave the reduced intermediate (874 mg, 22%).

The intermediate (870 mg, 2.1 mmol) was dissolved in methanol (30 mL) and palladium on charcoal (10%, 200 mg) and 5 drops of concentrated hydrochloric acid were added. After stirring in a hydrogen atmosphere (1 bar) at room temperature overnight the mixture was filtered and the solvent was evaporated. The residue was dissolved in dichloromethane (20 ml), triethyl amine (1.2 mL, 8.5 mmol) and 3,5-bistrifluoromethyl benzoylchloride (0.42 mL, 2.3 mmol) were added and the mixture was stirred at room temperature overnight. Water was added, the organic layer was separated and dried. The solvent was evaporated and the residue was purified by chromatography on silica gel (hexane, ethyl acetate 1:1) to yield the desired product (497 mg, 42%), MS: m/e=564.1 (M+H$^+$).

EXAMPLE 130

8-(3,5-Bis-trifluoromethyl-benzoyl)-4-methoxy-1,3 -diphenyl-1,3,8-triaza-spiro[4.5]decan-2-one The title compound, MS: m/e=578:0 (M$^+$), was obtained as a by product of example 129.

EXAMPLE 131

8-(3,5-Bis-trifluoromethyl-benzoyl)-1-o-tolyl-1,3,8-triaza-spiro[4.5]decan-2-one To a solution of 1-benzyl-piperidin-4-one (37.8 g, 200 mmol) in acetic acid (300 mL) were added at 0° C. o-toluidine (23.8 g, 220 mmol) and trimethylsilylcyanide (25.0 mL, 200 mmol). The suspension was stirred for 22 h at room temperature. The reaction mixture was than added to ice-water (500 mL) and ammonia was added until pH 9. After that the mixture was extracted with dichloromethane, the organic phases were pooled, washed with brine and dried with MgSO$_4$. The solvent was evaporated and the residue crystallized from diethylether to yield the intermediate amino nitrile (46.2 g, 75%).

The intermediate amino nitrile (29.5 g, 96 mmol) was dissolved in acetic acid (200 mL), PtO$_2$ (1.3 g, 5.7 mmol) was added and the reaction mixture was hydrogenated at 2.7 bar at room temperature for 3 days. Acetic acid was evaporated and the residue was treated with saturated sodium bicarbonate solution until pH 9. The mixture was than extracted with dichloromethane. Organic phases were pooled and dried with MgSO$_4$. Evaporation yielded 21.2 g (71%) of an oil.

To a solution of the intermediate triamine(3.2 g, 10.2 mmol) in dichloromethane(330 mL) and triethylamine (2.9 mL, 20.5 mmol) was added at −20° C. trichloromethyl chloroformat (0.446 mL, 3.6 mmol) in dichloromethane (30 mL). The reaction mixture was then stirred at room temperature overnight. Water (50 mL) was added and te mixture was extracted with dichloromethane. Organic phases were pooled and dried with MgSO$_4$. Evaporation and chromatography on silica gel (dichloromethane/methanol 99:1) yielded the intermediate N-benzyl protected spiropiperidine(1.4 g, 41%).

The intermediate N-benzyl protected spiropiperidine (3.05 g, 9.1 mmol) was dissolved in methanol (120 mL) and palladium on charcoal (10%, 610 mg) and 20 drops of concentrated hydrochloric acid were added. After stirring in a hydrogen atmosphere (1 bar) at room temperature overnight the mixture was filtered and the solvent was evaporated.

The residue was dissolved in dichloromethane (100 ml), triethyl amine (3.73 mL, 26.6 mmol) and 3,5-bistrifluoromethyl benzoylchloride (2.45 mL, 8.9 mmol) were added and the mixture was stirred at room temperature overnight. Water was added, the organic layer was separated and dried. The solvent was evaporated and the recrystallized from dichloromethane to yield the desired product as white crystalls (3.29 g, 76%), MS: m/e=486.3 (M+H$^+$).

EXAMPLE 132

8-(3,5-Bis-trifluoromethyl-benzoyl)-3-(2-pyrrolidin-1-yl-ethyl)-1-o-tolyl-3,8-triaza-spiro[4.5]decan-2-one The title compound, MS: m/e=583.2 (M+H$^+$), was prepared in accordance with the general method of example 99 from 8-(3,5-bis-trifluoromethyl-benzoyl)-1-o-tolyl-1,3,8-triaza-spiro[4.5]decan-2-one and 1-(2-chloroethyl)-pyrrolidine.

EXAMPLE 133

8-(3,5-Bis-trifluoromethyl-benzoyl)-3-methyl-1-o-tolyl-1,3,8-triaza-spiro[4.5]decan-4-one The title compound, MS: m/e=500.2 (M+H$^+$), was prepared in accordance with the general method of example 4 from 8-(3,5-bis-trifluoromethyl-benzoyl)-1-o-tolyl-1,3,8-triaza-spiro[4.5]decan-4-one and iodomethane in 1,2-dimethoxyethane as solvent.

EXAMPLE 134

8-(3,5-Bis-trifluoromethyl-benzoyl)-3-(2-methyl-thiazol-4-yl-methyl)-1-o-tolyl-1,3,8-triaza-spiro[4.5]decan-4-one The title compound, MS: m/e=597.0 (M+H$^+$), was prepared in accordance with the general method of example 4 from 8-(3,5-bis-trifluoromethyl-benzoyl)-1-o-tolyl-1,3,8-triaza-spiro[4.5]decan-4-one and 4-chloromethyl-2-methyl-thiazole in 1,2-dimethoxyethane as solvent.

EXAMPLE 135

8-(3,5-Bis-trifluoromethyl-benzoyl)-1-(2-chloro-phenyl)-1,3,8-triaza-spiro[4.5]decane-2,4-dione To a solution of 1-(3,5-bis-trifluoromethyl-benzoyl)-4-(2-chloro-phenylamino)-piperidine-4-carbonitrile (5.0 g, 10.5 mmol) in dichloromethane(50 mL) was added chlorosulfonyl isocyanate (1 mL, 11.5 mmol). Stirring continued for 1 h at room temperature. Evaporation of the solvent yielded a white foam, which was used without further purification in the next step.

The white foam was suspended in 1N hydrochloric acid (50 mL) and refluxed for 2 h. The obtained suspension was filtered to yield 5.4 g of a solid residue. Chromatography on silica gel (hexane, ethyl acetate 2:1) and recrystallization from ethyl acetate/n-hexane yielded the desired product (2.9 g, 53%), mp 153–154° C. MS: m/e=520.1 (M+H$^+$).

EXAMPLE 136

Rac-8-(3,5-Bis-trifluoromethyl-benzoyl)-2-methyl-3-phenyl-1-o-tolyl-1,3,8-triaza-spiro[4.5]decan-4-one The title compound, MS: m/e=576.0 (M+H$^+$), was prepared in accordance with the general method of example 62 from (rac)-8-(3,5-bis-trifluoromethyl-benzoyl)-2-methyl-1-o-tolyl-1,3,8-triaza-spiro[4.5]decan-4-one and 4 phenylboronic acid.

EXAMPLE 137

Rac-8-(3,5-Bis-trifluoromethyl-benzoyl)-3-(2-methoxy-ethyl)-2-methyl-1-o-tolyl-1,3,8-triaza-spiro[4.5]decan-4-one The title compound, MS: m/e=542.2 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 2-chloroethyl-methyl ether.

EXAMPLE 138

Rac-8-(3,5-Bis-trifluoromethyl-benzoyl)-3-cyclopropylmethyl-2-methyl-1-o-tolyl-1,3,8-triaza-spiro[4.5]decan-4-one The title compound, MS: m/e=554.2 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and cyclopropyl methyl bromide.

EXAMPLE 139

Rac-8-(3,5-Bis-trifluoromethyl-benzoyl)-3-(2,2-difluoro-ethyl)-2-methyl-1-o-tolyl-1,3,8-triaza-spiro[4.5]decan-4-one The title compound, MS: m/e=564.2 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 2,2-difluoroethyl bromide.

EXAMPLE 140

Rac-8-(3,5-Bis-trifluoromethyl-benzoyl)-2-methyl-3-(3-methyl-but-2-enyl)-1-o-tolyl-1,3,8-triaza-spiro[4.5]decan-4-one The title compound, MS: m/e=568.2 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 1-bromo-3-methyl-2-butene.

EXAMPLE 141

Rac-8-(3,5-Bis-trifluoromethyl-benzoyl)-2-methyl-3-(2-morpholin-4-yl-ethyl)-1-o-tolyl-1,3,8-triaza-spiro[4.5]decan-4-one The title compound, MS: m/e=613.2 (M+H$^+$), was prepared in accordance with the general method of example 99 from (rac)-8-(3,5-bis-trifluoromethyl-benzoyl)-2-methyl-1-o-tolyl-1,3,8-triaza-spiro[4.5]decan-4-one and 4-(chloroethyl)morpholine.

EXAMPLE 142

8-(3,5-Bis-trifluoromethyl-benzoyl)-3-(1-methyl-1H-imidazol-2-yl-methyl)-1-o-tolyl-1,3,8-triaza-spiro[4.5]decan-4-one The title compound, MS: m/e=580.3 (M+H$^+$), was prepared in accordance with the general method of example 99 from 8-(3,5-bis-trifluoromethyl-benzoyl)-1-o-tolyl-1,3,8-triaza-spiro[4.5]decan-4-one and 2-chloromethyl-1-methyl-1H-imidazole.

EXAMPLE 143

8-(3,5-Bis-trifluoromethyl-benzoyl)-1-(2-chloro-phenyl)-3-(1-methyl-1H-imidazol-2-ylmethyl)-1,3,8-triaza-spiro[4.5]decane-2,4-dione The title compound, MS: m/e=614.1 (M+H$^+$), was prepared in accordance with the general method of example 121 from 8-(3,5-bis-trifluoromethyl-benzoyl)-1-(2-chloro-phenyl)-1,3,8-triaza-spiro[4.5]decane-2,4-dione and 1-methylimidazole-2-methanol.

EXAMPLE 144

8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione The title compound, MS: m/e=627.1 (M$^+$), was prepared in accordance with the general method of example 121 from 8-(3,5-bis-trifluoromethyl-benzoyl)-1-(2-chloro-phenyl)-1,3,8-triaza-spiro[4.5]decane-2,4-dione and 1,5-dimethylpyrazole-3-methanol.

EXAMPLE 145

8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione The title compound, MS: m/e=585.1 (M$^+$), was prepared in accordance with the general method of example 121 from 8-(3,5-bis-trifluoromethyl-benzoyl)-3-(3-dimethylamino-propyl)-1-o-tolyl-1,3,8-triaza-spiro[4.5]decane-2,4-dione and 3-dimethylamino-1-propyl chloride.

EXAMPLE 146

(rac)-8-(3,5-Dimethoxy-benzoyl)-2-methyl-1-o-tolyl-1,3,8-triaza-spiro[4.5]decan-4-one The title compound, MS: m/e=424.5 (M+H$^+$), was prepared in accordance with the general method of example 91 from 1-benzyl-piperidin-4-one, 1-methyl aniline, methyl magnesium bromide and 3,5-dimethoxy benzoyl chloride.

EXAMPLE 147

(rac)-8-(3,5-Dichloro-benzoyl)-2-methyl-1-o-tolyl-1,3,8-triaza-spiro[4.5]decan-4-one The title compound, MS: m/e=432.4 (M+H$^+$), was prepared in accordance with the general method of example 91 from 1-benzyl-piperidin-4-one, 1-methyl aniline, methyl magnesium bromide and 3,5-dichloro benzoyl chloride.

EXAMPLE 148

(rac)-8-(3-Fluoro-5-trifluoromethyl-benzoyl)-2-methyl-1-o-tolyl-1,3,8-triaza-spiro[4.5]decan-4-one The title compound, MS: m/e=450.4 (M+H$^+$), was prepared in accordance with the general method of example 91 from 1-benzyl-piperidin-4-one, 1-methyl aniline, methyl magnesium bromide and 3-fluoro-5-trifluoromethyl-benzoyl chloride.

EXAMPLE 149

(rac)-8-(3,5-Difluoro-benzoyl)-2-methyl-1-o-tolyl-1,3,8-triaza-spiro[4.5]decan-4-one The title compound, MS: m/e=400.5 (M+H$^+$), was prepared in accordance with the general method of example 91 from 1-benzyl-piperidin-4-one, 1-methyl aniline, methyl magnesium bromide and 3,5-difluoro-benzoyl chloride.

EXAMPLE 150

8-(3,5-Bis-trifluoromethyl-benzoyl)-3-cyclopropylmethyl-1-o-tolyl-1,3,8-triaza-spiro[4.5]decan-2-one The title compound, MS: m/e=540.4 (M+H$^+$), was prepared in accordance with the general method of example 99 from 8-(3,5-bis-trifluoromethyl-benzoyl)-1-o-tolyl-1,3,8-triaza-spiro[4.5]decan-2-one and cyclopropyl methyl bromide.

EXAMPLE 151

8-(3,5-Bis-trifluoromethyl-benzoyl)-3-methyl-1-o-tolyl-1,3,8-triaza-spiro[4.5]decan-2-one The title compound, MS: m/e=500.2 (M+H$^+$), was prepared in accordance with the general method of example 99 from 8-(3,5-bis-trifluoromethyl-benzoyl)-1-o-tolyl-1,3,8-triaza-spiro[4.5]decan-2-one and methyl iodide.

EXAMPLE 152

8-(3,5-Bis-trifluoromethyl-benzoyl)-3-(2-morpholin-4-yl-ethyl)-1-o-tolyl-1,3,8-triaza-spiro[4.5]decan-2-one The title compound, MS: m/e=599.1 (M+H$^+$), was prepared in accordance with the general method of example 99 from 8-(3,5-bis-trifluoromethyl-benzoyl)-1-o-tolyl-1,3,8-triaza-spiro[4.5]decan-2-one and 4-(chloroethyl) morpholine.

EXAMPLE 153

8-(3,5-Bis-trifluoromethyl-benzoyl)-3-(2-methoxy-ethyl)-1-o-tolyl-1,3,8-triaza-spiro[4.5]decan-2-one The title compound, MS: m/e=544.2 (M+H$^+$), was prepared in accordance with the general method of example 99 from 8-(3,5-bis-trifluoromethyl-benzoyl)-1-o-tolyl-1,3,8-triaza-spiro[4.5]decan-2-one and 2-chloromethyl methyl ether.

EXAMPLE 154

8-(3,5-Bis-trifluoromethyl-benzoyl)-3-(3-dimethylamino-propyl)-1-o-tolyl-1,3,8-triaza-spiro[4.5]decan-2-one The title compound, MS: m/e=571.1 (M+H$^+$), was prepared in accordance with the general method of example 99 from 8-(3,5-bis-trifluoromethyl-benzoyl)-1-o-tolyl-1,3,8-triaza-spiro[4.5]decan-2-one and 3-dimethylamino-1-propyl chloride.

EXAMPLE 155

3-Acetyl-8-(3,5-bis-trifluoromethyl-benzoyl)-1-o-tolyl-1,3,8-triaza-spiro[4.5]decan-2-one The title compound, MS: m/e=528.1 (M+H$^+$), was prepared in accordance with the general method of example 99 from 8-(3,5-bis-trifluoromethyl-benzoyl)-1-o-tolyl-1,3,8-triaza-spiro[4.5]decan-2-one and acetyl chloride.

EXAMPLE 156

(rac)-8-(3,5-Bis-trifluoromethyl-benzoyl)-4-phenyl-2,8-diaza-spiro[4.5]decane-1,3-dione To a solution sodium ethoxide (prepared by slow addition of 22 g, 0.96 mol Na to dry 800 mL ethanol) was added benzyl cyanide (113 g, 1.05 mol) and N-benzyl-4-piperidone (90 g, 0.48 mol) at room temperature. The reaction mixture was stirred at 85° C. for 3 h and the solvent was evaporated. The residue was poured into a mixture of ice (1 kg) and concentrated hydrochloric acid (200 mL). The pH was then adjusted to 9 addition of solid sodium hydroxide and the mixture was extracted three times with ethyl acetate (500 mL each). Organic phases were pooled and dried with MgSO$_4$. The solvent was evaporated and chromatography on silica gel (hexane, ethyl acetate, triethyl amine 80:20:1) gave (1-benzyl-piperidin-4-ylidene)-phenyl-acetonitrile as yellow crystals (135 g, 97%).

To a solution of the intermediate (1-benzyl-piperidin-4-ylidene)-phenyl-acetonitrile (135 g, 0.47 mol) in ethanol (400 mL) was added potassium cyanide (30 g, 0.47 mol) in water (80 mL). Stirring continued at 90° C. overnight. The solvent was evaporated. The residue was taken up in 2N hydrochloric acid (300 mL) and concentrated hydrochloric acid (50 mL) was added to adjust at pH 1–2. The reaction mixture was stirred at reflux overnight. After cooling to room temperature solid sodium carbonate until pH 8–9 was added and the mixture was extracted three times with methylene chloride (300 mL each). Organic phases were pooled, dried with $MgSO_4$ and evaporated. The crude product was suspended in ethyl acetate (300 mL) and left at room temperature overnight. The crystals were filtered off and dried to give 106 g (68%) of the intermediate (rac)-8-benzyl-4-phenyl-2,8-diaza-spiro[4.5]decane-1,3-dione.

The intermediate (rac)-8-benzyl-4-phenyl-2,8-diaza-spiro[4.5]decane-1,3-dion (4.0 g 12 mmol) was dissolved in methanol (100 mL) and concentrated hydrochloric acid(1 mL) and palladium on charcoal (10%, 0.60 g) were added. After stirring in a hydrogen atmosphere (1 bar) at room temperature overnight the mixture was filtered and the solvent was evaporated.

The residue was dissolved in dichloromethane (100 ml), triethyl amine (5.5 mL, 40 mmol) and 3,5-bistrifluoromethyl benzoylchloride (2.7 mL, 15 mmol) were added and the mixture was stirred at room temperature overnight. Water was added, the organic layer was separated and dried. The solvent was evaporated and the residue was purified by flash chromatography on silica gel (hexane, ethyl acetate, triethyl amine 30:10:1) to yield the desired product (3.44 g, 59%), MS: m/e=485.3 (M+H$^+$).

EXAMPLE 157

(rac)-8-(3,5-Bis-trifluoromethyl-benzoyl)-2-methyl-4-phenyl-2,8-diaza-spiro[4.5]decane-1,3-dione The title compound, MS: m/e=499.2 (M+H$^+$), was prepared in accordance with the general method of example 121 from (rac)-8-(3,5-bis-trifluoromethyl-benzoyl)-4-phenyl-2,8-diaza-spiro[4.5]decane-1,3-dione and methyl iodide.

EXAMPLE 158

(rac)-8-(3,5-Bis-trifluoromethyl-benzoyl)-2-(2-morpholin-4-yl-ethyl)-4-phenyl-2,8-diaza-spiro[4.5]decane-1 3-dione The title compound, MS: m/e=598.1 (M+H$^+$), was prepared in accordance with the general method of example 121 from (rac)-8-(3,5-bis-trifluoromethyl-benzoyl)-4-phenyl-2,8-diaza-spiro[4.5]decane-1,3-dione and N-(2-hydroxyethyl)-morpholine.

EXAMPLE 159

(rac)-8-(3,5-Bis-trifluoromethyl-benzoyl)-4-phenyl-2-(2-pyrrolidin-1-yl-ethyl)-2,8-diaza-spiro[4.5]decane-1,3-dione The title compound, MS: m/e=582.2 (M+H$^+$), was prepared in accordance with the general method of example 121 from (rac)-8-(3,5-bis-trifluoromethyl-benzoyl)-4-phenyl-2,8-diaza-spiro[4.5]decane-1,3-dione and 1-(2-hydroxyethyl)-pyrrolidine.

EXAMPLE 160

(rac)-8-(3,5-Bis-trifluoromethyl-benzoyl)-2-(3-dimethylamino-propyl)-4-phenyl-2,8-diaza-spiro[4.5]decane-1,3-dione The title compound, MS: m/e=570.2 (M+H$^+$), was prepared in accordance with the general method of example 121 from (rac)-8-(3,5-bis-trifluoromethyl-benzoyl)-4-phenyl-2,8-diaza-spiro[4.5]decane-1,3 -dione and 3-dimethylamino-1-propanol.

EXAMPLE 161

(rac)-8-(3,5-Bis-trifluoromethyl-benzoyl)-4-phenyl-2,8-diaza-spiro[4.5]decan-1-one (rac)-8-Benzyl-4-phenyl-2,8-diaza-spiro[4.5]decane-1,3-dion (10.0 g, 30 mmol synthesis described in example 156) was dissolved in toluene (200 mL). Diisobutyl aluminium hydride (220 mL, 1M in THF, 220 mmol) was slowly added while cooling with an ice bath so that the reaction temperature did not exceed 10° C. The reaction mixture was stirred at room temperature for 2 days. A mixture of methanol (6 mL) and water (6 mL) was added at room temperature. The resulting gel was filtered through dicalit and washed with methylene chloride. The filtrate was evaporated to give 8-benzyl-3-hydroxy-4-phenyl-2,8-diaza-spiro[4.5]decan-1-one as a mixture of diastereomers (8.0 g, 80%).

The intermediate 8-benzyl-3-hydroxy-4-phenyl-2,8-diaza-spiro[4.5]decan-1-one (8.0 g, 23.8 mmol) was dissolved in glacial acetic acid (50 mL) and refluxed for 1.5 h. The reaction mixture was poured into ice water (500 mL) and adjusted to pH 8–9 by. addition of solid sodium hydroxide. The mixture was extracted three times with ethyl acetate (300 mL each). Organic phases were pooled, dried with magnesium sulfate and evaporated. The crude product was recrystallized from methylene chloride to give 8-benzyl-4-phenyl-2,8-diaza-spiro[4.5]dec-3-en-1-one as white crystalls (2.64 g, 35%).

The intermediate 8-benzyl-4-phenyl-2,8-diaza-spiro[4.5]dec-3-en-1-one (3.7 g, 11.6 mmol) was dissolved in methanol (100 mL) and concentrated hydrochloric acid(1 mL) and palladium on charcoal (10%, 0.60 g) were added. After stirring in a hydrogen atmosphere (1 bar) at room temperature overnight the mixture was filtered and the solvent was evaporated.

The residue was dissolved in dichloromethane (100 ml), triethyl amine (8.1 mL, 58 mmol) and 3,5-bistrifluoromethyl benzoylchloride (2.65 mL, 15 mmol) were added and the mixture was stirred at room temperature overnight. Water was added, the organic layer was separated and dried. The solvent was evaporated and the residue was purified by flash chromatography on silica gel (methylene chloride/methanol 98:2) to yield the desired product (4.65 g, 85%), MS: m/e=471.2 (M+H$^+$).

EXAMPLE 162

(rac)-8-(3,5-Bis-trifluoromethyl-benzoyl)-2-methyl-4-phenyl-2.8-diaza-spiro[4.5]decan-1-one The title compound, MS: m/e=485.3 (M+H$^+$), was prepared in accordance with the general method of example 99 from (rac)-8-(3,5-bis-trifluoromethyl-benzoyl)-4-phenyl-2,8-diaza-spiro[4.5]decan-1-one and methyl iodide.

EXAMPLE 163

(rac)-8-(3,5-Bis-trifluoromethyl-benzoyl)-4-phenyl-2-(2-pyrrolidin-1-yl-ethyl)-2,8-diaza-spiro[4.5]decan-1-one The title compound, MS: m/e=568.3 (M+H$^+$), was prepared in accordance with the general method of example 99 from (rac)-8-(3,5-bis-trifluoromethyl-benzoyl)-4-phenyl-2,8-diaza-spiro[4.5]decan-1-one and 1-(2-chloroethyl)-pyrrolidine.

EXAMPLE 164

(rac)-8-(3,5-Bis-trifluoromethyl-benzoyl)-2-(2-methoxy-ethyl)-4-phenyl-2,8-diaza-spiro[4.5]decan-1-one The title compound, MS: m/e=529.2 (M+H⁺), was prepared in accordance with the general method of example 99 from (rac)-8-(3,5-bis-trifluoromethyl-benzoyl)-4-phenyl-2,8-diaza-spiro[4.5]decan-1-one and 2-chloroethyl-methyl-ether.

EXAMPLE 165

(rac)-8-(3,5-Bis-trifluoromethyl-benzoyl)-2-(2-morpholin-4-yl-ethyl)-4-phenyl-2,8-diaza-spiro[4.5]decan-1-one The title compound, MS: m/e=584.1 (M+H⁺), was prepared in accordance with the general method of example 99 from (rac)-8-(3,5-bis-trifluoromethyl-benzoyl)-4-phenyl-2,8-diaza-spiro[4.5]decan-1-one and 4-(2-chloroethyl)-morpholine.

EXAMPLE 166

(rac)-8-(3,5-Bis-trifluoromethyl-benzoyl)-2-(3-dimethylamino-propyl)-4-phenyl-2,8-diaza-spiro[4.5]decan-1-one The title compound, MS: m/e=556.2 (M+H⁺), was prepared in accordance with the general method of example 99 from (rac)-8-(3,5-bis-trifluoromethyl-benzoyl)-4-phenyl-2,8-diaza-spiro[4.5]decan-1-one and 3-dimethylamino-1-propyl chloride.

EXAMPLE 167

(rac)-8-(3,5-Bis-trifluoromethyl-benzoyl)-4-phenyl-2-pyridin-3-yl-methyl-2,8-diaza-spiro[4.5]decan-1-one The title compound, MS: m/e=562.3 (M+H⁺), was prepared in accordance with the general method of example 99 from (rac)-8-(3,5-bis-trifluoromethyl-benzoyl)-4-phenyl-2,8-diaza-spiro[4.5]decan-1-one and 3-(chloromethyl)pyridine.

EXAMPLE 168

(rac)-(3,5-Bis-trifluoromethyl-phenyl)-(2-methyl-4-phenyl-2,8-diaza-spiro[4.5]dec-8-yl)-methanone (rac)-8-Benzyl-4-phenyl-2,8-diaza-spiro[4.5]decane-1,3-dion (3.0 g, 9.0 mmol, synthesis described in example 156) was dissolved in dry tetrahydrofuran (50 mL) and triphenylphosphin (3.1 g, 11.7 mmol), methanol (0.374 g, 11.7 mmol) and diethylazodicarboxylate (5.35 mL, 40% in toluene, 11.7 mmol) were added sequentially and stirred at room temperature overnight. The solvent was evaporated and the residue was purified by chromatography on silica gel (dichloromethane/methanol/triethyl amine 98:1:1) to yield the intermediate (rac)-8-benzyl-2-methyl-4-phenyl-2,8-diaza-spiro[4.5]decane-1,3-dion (2.57 g, 82%).

Lithium aluminium hydride (1.39 g, 37 mmol) was dissolved in tetarhydrofuran (20 mL) and the intermediate (rac)-8-benzyl-2-methyl-4-phenyl-2,8-diaza-spiro[4.5]decane-1,3-dion (2.55 g, 7.32 mmol, dissolved in 20 mL dry tetrahydrofuran) was added slowly. The reaction mixture was stirred at room temperature for 2 h. Water (1.4 mL), sodium hydroxide (15% in water, 1.5 mL) and water (4.2 mL) were added dropwise. The precipitate was filtered off and the filtrate was evaporated. The residue was purified by flash chromatography (hexane/ethyl acetate/triethyl amine 30:20.1) to yield the intermediate (rac)-8-benzyl-2-methyl-4-phenyl-2,8-diaza-spiro[4.5]decane (1.40 g, 60%).

The intermediate (rac)-8-benzyl-2-methyl-4-phenyl-2,8-diaza-spiro[4.5]decane (1.29 g, 2.51 mmol) was dissolved in methanol (50 mL) and concentrated hydrochloric acid(0.3 mL) and palladium on charcoal (10%, 0.214 g) were added. After stirring in a hydrogen atmosphere (1 bar) at room temperature overnight the mixture was filtered and the solvent was evaporated.

The residue was dissolved in dichloromethane (50 ml), triethyl amine (2.04 mL, 20 mmol) and 3,5-bistrifluoromethyl benzoylchloride (0.95 mL, 5.2 mmol) were added and the mixture was stirred at room temperature overnight. Water was added, the organic layer was separated and dried. The solvent was evaporated and the residue was purified by flash chromatography on silica gel (hexane/ethyl acetate/triethyl amine 10:20:1) to yield the desired product (1.18 g, 62%), MS: m/e=471.2 (M+H⁺).

EXAMPLE 169

8-(3,5-Bis-trifluoromethyl-benzoyl)-4-o-tolyl-2,8-diaza-spiro[4.5]dec-3-en-1-one The title compound, MS: m/e=483.1 (M+H⁺), was prepared in accordance with the general methods of example 156 and 161 from o-tolyl cyanide and N-benzyl-4-piperidone. Reduction of the double bond with hydrogen was not successful and the 2,8-diaza-spiro[4.5]dec-3-en-1-one core was obtained instead of the 2,8-diaza-spiro[4.5]decan-1-one core.

EXAMPLE 170

8-(3,5-Bis-trifluoromethyl-benzoyl)-2-methyl-4-o-tolyl-2,8-diaza-spiro[4.5]dec-3-en-1-one The title compound, MS: m/e=497.1 (M+H⁺), was prepared in accordance with the general method of example 99 from 8-(3,5-bis-trifluoromethyl-benzoyl)-4-o-tolyl-2,8-diaza-spiro[4.5]dec-3-en-1-one and methyl iodide.

EXAMPLE 171

8-(3,5-Bis-trifluoromethyl-benzoyl)-2-cyclopropylmethyl-4-o-tolyl-2,8-diaza-spiro[4.5]dec-3-en-1-one The title compound, MS: m/e=537.2 (M+H⁺), was prepared in accordance with the general method of example 99 from 8-(3,5-bis-trifluoromethyl-benzoyl)-4-o-tolyl-2,8-diaza-spiro[4.5]dec-3-en-1-one and cyclopropyl methyl bromide.

EXAMPLE 172

8-(3,5-Bis-trifluoromethyl-benzoyl)-2-(2-pyrrolidin-1-yl-ethyl)-4-o-tolyl-2,8-diaza-spiro[4.5]dec-3-en-1-one The title compound, MS: m/e=580.1 (M+H⁺), was prepared in accordance with the general method of example 99 from 8-(3,5-bis-trifluoromethyl-benzoyl)-4-o-tolyl-2,8-diaza-spiro[4.5]dec-3-en-1-one and 1-(2-chloroethyl)-pyrrolidine.

EXAMPLE 173

8-(3,5-Bis-trifluoromethyl-benzoyl)-2-(2-morpholin-4-yl-ethyl)-4-o-tolyl-2,8-diaza-spiro[4.5]dec-3-en-1-one The title compound, MS: m/e=596.1 (M+H$^+$), was prepared in accordance with the general method of example 99 from 8-(3,5-bis-trifluoromethyl-benzoyl)-4-o-tolyl-2,8-diaza-spiro[4.5]dec-3-en-1-one and 1-(2-chloroethyl)-morpholine.

EXAMPLE 174

8-(3,5-Bis-trifluoromethyl-benzoyl)-2-(3-dimethylamino-propyl)-4-o-tolyl-2,8-diaza-spiro[4.5]dec-3-en-1-one The title compound, MS: m/e=568.2 (M+H$^+$), was prepared in accordance with the general method of example 99 from 8-(3,5-bis-trifluoromethyl-benzoyl)-4-o-tolyl-2,8-diaza-spiro[4.5]dec-3-en-1-one and 3-dimethylamino-1-propyl chloride.

EXAMPLE 175

8-(3,5-Bis-trifluoromethyl-benzoyl)-2-pyridin-3-yl-methyl-4-o-tolyl-2,8-diaza-spiro[4.5]dec-3-en-1-one The title compound, MS: m/e=574.1 (M+H$^+$), was prepared in accordance with the general method of example 99 from 8-(3,5-bis-trifluoromethyl-benzoyl)-4-o-tolyl-2,8-diaza-spiro[4.5]dec-3-en-1-one and 3-chloromethyl pyridine.

EXAMPLE 176

(rac)-8-(3,5-Bis-trifluoromethyl-benzoyl)-4-o-tolyl-2,8-diaza-spiro[4.5]decan-1-one The title compound, MS: m/e=485.3 (M+H$^+$), was prepared in accordance with the general methods of example 156 and 161 from o-tolyl cyanide and N-benzyl-4-piperidone. Reduction with hydrogen was performed for three days to also reduce the double bond.

EXAMPLE A 1-(3,5-Bis-trifluoromethyl-benzoyl)-piperidin-4-one

A solution of 3,5-bis-trifluoromethyl-benzoyl chloride (17.4 g, 63 mmol) in dichloromethane (30 mL) was added with cooling to a solution of 4-piperidone trifluoroacetate (13.4 g, 63 mmol) and triethylamine (22 mL, 158 mmol) so that the temperature did not rise above 20° C. Stirring continued for 2 h at room temperature. Water was added, the phases were separated and the water phase was extracted with dichloromethane. The organic phases were pooled, dried with MgSO$_4$ and the solvent was evaporated. Chromatography on silica gel (ethyl acetate/n-hexane 1:1) yielded the desired product (20.2 g, 94%), m.p. 155–157° C. and MS: m/e=339.1 (M$^+$).

EXAMPLE B 1-(3,5-Bis-trifluoromethyl-benzoyl)-4-(3-chloro-phenylamino)-piperidine-4-carbonitrile To a solution of 1-(3,5-bis-trifluoromethyl-benzoyl)-piperidin-4-one (5.1 g, 15 mmol) in acetic acid (20 mL) were added with cooling 3-chloroaniline (1.7 mL, 16.5 mmol) and trimethylsilylcyanide (1.9 mL, 15 mmol) so that the temperature did not rise above 20° C. The suspension was stirred for 6 h at room temperature. The reaction mixture was than added to ice-water (350 mL), ammonia (55 mL, 25%) was added to the mixture which was stirred for 15 min. After that the mixture was extracted with dichloromethane, the organic phases were pooled, washed with brine and dried with MgSO$_4$. The solvent was evaporated and the residue crystallized from ethylacetate to yield the desired product (5.3 g, 74%), m.p. 205–207° C. and MS: m/e=476.1 (M+H$^+$).

EXAMPLE C 1-(3,5-Bis-trifluoromethyl-benzoyl)-4-(4-chloro-phenylamino)-piperidine-4-carbonitrile The title compound, m.p. 176–180° C. and MS: m/e=474.1 (M–H$^-$), was prepared in accordance with the general method of example B from 1-(3,5-bis-trifluoromethyl-benzoyl)-piperidin-4-one and 4-chloroaniline.

EXAMPLE D 1-(3,5-Bis-trifluoromethyl-benzoyl)-4-(3,4-dichloro-phenylamino)-piperidine-4-carbonitrile The title compound, m.p. 195–197° C. and MS: m/e=512.1 (M+H$^+$), was prepared in accordance with the general method of example B from 1-(3,5-bis-trifluoromethyl-benzoyl)-piperidin-4-one and 3,4-dichloroaniline.

EXAMPLE E 1-(3,5-Bis-trifluoromethyl-benzoyl)-4-o-tolylamino-piperidine-4-carbonitrile The title compound, m.p. 141–142° C. and MS: m/e=456.3 (M+H$^+$), was prepared in accordance with the general method of example B from 1-(3,5-bis-trifluoromethyl-benzoyl)-piperidin-4-one and 2-methylaniline.

EXAMPLE F 1-(3,5-Bis-trifluoromethyl-benzoyl)-4-(2-chloro-phenylamino)-piperidine-4-carbonitrile The title compound, MS: m/e=474.1 (M–H$^-$), was prepared in accordance with the general method of example B from 1-(3,5-bis-trifluoromethyl-benzoyl)-piperidin-4-one and 2-chloroaniline.

EXAMPLE G 1-(3,5-Bis-trifluoromethyl-benzoyl)-4-(2-methoxy-phenylamino)-piperidine-4-carbonitrile The title compound, MS: m/e=472.2 (M+H$^+$), was prepared in accordance with the general method of example B from 1-(3,5-bis-trifluoromethyl-benzoyl)-piperidin-4-one and o-anisidine.

EXAMPLE H

4-Benzylamino-1-(3,5-bis-trifluoromethyl-benzoyl)-piperidine-4-carbonitrile

The title compound, MS: m/e=456.3 (M+H$^+$), was prepared in accordance with the general method of example B from 1-(3,5-bis-trifluoromethyl-benzoyl)-piperidin-4-one and benzylamine.

MS m/e (%): 586 (M+H$^+$, 100).

EXAMPLE AA

Tablets of the following composition are manufactured in the usual manner:

| mg/tablet | |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE BB

Capsules of the following composition are manufactured:

| mg/capsule | |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE CC

Suppositories of the following composition are manufactured:

| mg/supp. | |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the formula

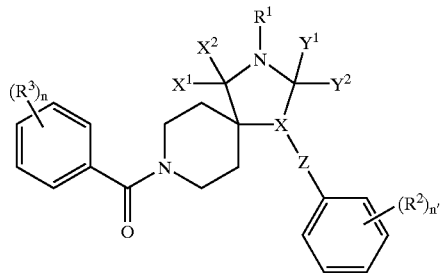

I wherein

R$^1$ is hydrogen, lower alkyl, lower alkenyl, phenyl or the following groups

—(CH$_2$)$_m$-non aromatic heterocyclic, which is unsubstituted or substituted by lower alkyl, or is —(CH$_2$)$_m$-heteroaryl, which is unsubstituted or substituted by one or two substituents selected from the group consisting of lower alkyl, lower alkoxy, halogen, CF$_3$, benzyl or cyano, or is —(CH$_2$)$_m$—C(O)—NRR', —(CH$_2$)$_m$—C(O)-lower alkyl, —(CH$_2$)$_m$—C(O)—O-lower alkyl, —(CH$_2$)$_m$—O-lower alkyl, —(CH$_2$)$_m$—CH[C(O)—O-lower alkyl]$_2$, —(CH$_2$)$_m$CH(OH)—CH$_2$—O-phenyl, —(CH$_2$)$_m$—CH(CF$_3$)OH, —(CH$_2$)$_m$—OH, —(CH$_2$)$_m$—CN, —(CH$_2$)$_m$—NRR', —(CH$_2$)$_m$-cycloalkyl or —(CH$_2$)$_m$—CHF$_2$ R$^2$ is hydrogen, lower alkyl, halogen or lower alkoxy;

R$^3$ is lower alkyl, lower alkoxy, halogen or CF$_3$;

R,R' are the same or different and are hydrogen or lower alkyl;

X is >N—, or >CH—;

X$^1$/X$^2$ are hydrogen, hydroxy or lower alkoxy or taken together to form an oxo group;

Y$^1$/Y$^2$ are hydrogen, lower alkyl, —(CH$_2$)$_m$-phenyl or taken together to form an oxo group;

Z —(CH$_2$)$_q$— or —C(O)—;

m is 0, 1, 2, 3 or 4;

n is 2 or 3;

n' 0, 1 or 2;

q is 0 or 1;

or a pharmaceutically acceptable acid addition salt thereof.

2. The compound of claim 1 having the formula

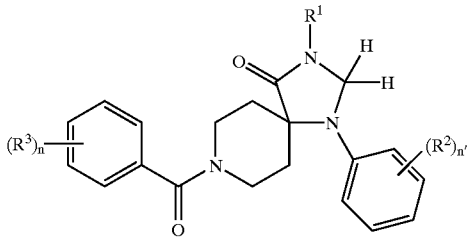

I-b wherein $R^1$, $R^2$ and $R^3$ are as defined in claim 1.

3. A compound of claim 2 wherein n=2 and one of $R^3$ is F and the other of $R^3$ is $CF_3$.

4. A compound of claim 3 where the compound is 8-(3-Fluoro-5-trifluoromethyl-benzoyl-1-phenyl-1,3,8-triaza-spiro[4.5]decan-4-one.

5. A compound of claim 2 having the formula

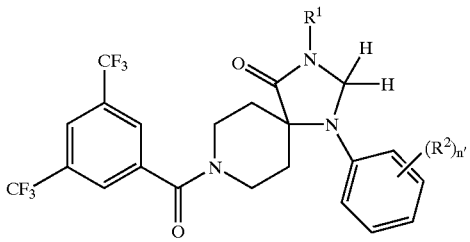

I-c wherein $R^1$ and $R^2$ are as defined in claim 2.

6. A compound of claim 3 wherein $R^1$ is hydrogen and $R^2$ is hydrogen.

7. A compound of claim 6 wherein the compound is 8-(3,5-Bis-trifluoromethyl-benzoyl)-1-phenyl-1,3,8-triaza-spiro[4.5]decan-4-one.

8. The compound of claim 5 wherein $R^1$ is phenyl or —$(CH_2)_m$-unsubstituted heteroaryl.

9. A compound of claim 8 wherein the compound is 8-(3,5-Bis-trifluoromethyl-benzoyl)-1-phenyl-3-pyridin-3-yl-methyl-1,3,8-triaza-spiro[4.5]decan-4-one.

10. A compound of claim 8 wherein the compound is 8-(3,5-Bis-trifluoromethyl-benzoyl)-1-phenyl-3-pyridin-2-yl-methyl-1,3,8-triaza-spiro[4.5]decan-4-one.

11. A compound of claim 8 wherein the compound is 8-(3,5-Bis-trifluoromethyl-benzoyl)-1-phenyl-3-pyridin-4-yl-methyl-1,3,8-triaza-spiro[4.5]decan-4-one.

12. A compound of claim 8 wherein the compound is 8-(3,5-Bis-trifluoromethyl-benzoyl)-3-(3-imidazol-1-yl-propyl)-1-phenyl-1,3,8-triaza-spiro[4.5]decan-4-one.

13. A compound of claim 8 wherein the compound is 8-(3,5-Bis-trifluoromethyl-benzoyl)-3-(2-imidazol-1-yl-ethyl)-1-phenyl-1,3,8-triaza-spiro[4.5]decan-4-one.

14. A compound of claim 8 wherein the compound is 8-(3,5-Bis-trifluoromethyl-benzoyl)-1-phenyl-3-pyrimidin-2-yl-1,3,8-triaza-spiro[4.5]decan-4-one.

15. A compound of claim 8 wherein the compound is 8-(3,5-Bis-trifluoromethyl-benzoyl)-1-phenyl-3-pyrazin-2-yl-1,3,8-triaza-spiro[4.5]decan-4-one.

16. A compound of claim 5 wherein $R^1$ is —$(CH_2)_m$-substituted heteroaryl and $R^2$ is hydrogen.

17. A compound of claim 16 wherein the compound is 8-(3,5-Bis-trifluoromethyl-benzoyl)-3-(4,6-dimethoxy-[1,3,5]triazin-2-yl)-1-phenyl-1,3,8-triaza-spiro[4.5]decan-4-one.

18. A compound of claim 16 wherein the compound is 8-(3,5-Bis-trifluoromethyl-benzoyl)-3-(4,6-dichloro-pyrimidin-2-yl)-1-phenyl-1,3,8-triaza-spiro[4.5]decan-4-one.

19. A compound of claim 16 wherein the compound is 8-(3,5-Bis-trifluoromethyl-benzoyl)-1-phenyl-3-(5-trifluoromethyl-pyridin-2-yl)-1,3,8-triaza-spiro[4.5]decan-4-one.

20. A compound of claim 16 wherein the compound is 8-(3,5-Bis-trifluoromethyl-benzoyl)-3-(4-chloro-pyrimidin-2-yl)-1-phenyl-1,3,8-triaza-spiro[4.5]decan-4-one.

21. A compound of claim 16 wherein the compound is 8-(3,5-Bis-trifluoromethyl-benzoyl)-3-(4-chloro-6-methyl-pyrimidin-2-yl)-1-phenyl-1,3,8-triaza-spiro[4.5]decan-4-one.

22. A compound of claim 16 wherein the compound is 8-(3,5-Bis-trifluoromethyl-benzoyl)-3-(3,5-dichloro-pyridin-2-yl)-1-phenyl-1,3,8-triaza-spiro[4.5]decan-4-one.

23. A compound of claim 16 wherein the compound is 2-[8-(3,5-Bis-trifluoromethyl-benzoyl)-4-oxo-1-phenyl-1,3,8-triaza-spiro[4.5]dec-3-yl]-6-methyl-nicotinonitrile.

24. A compound of claim 16 wherein the compound is 8-(3,5-Bis-trifluoromethyl-benzoyl)-3-(3-chloro-5-trifluoromethyl-pyridin-2-yl)-1-phenyl-1,3,8-triaza-spiro[4.5]decan-4-one.

25. A compound of claim 16 wherein the compound is 8-(3,5-Bis-trifluoromethyl-benzoyl)-3-(5-ethyl-pyrimidin-2-yl)-1-phenyl-1,3,8-triaza-spiro[4.5]decan-4-one.

26. A compound of claim 16 wherein the compound is 8-(3,5-Bis-trifluoromethyl-benzoyl)-1-phenyl-3-(4-trifluoromethyl-pyrimidin-2-yl)-1,3,8-triaza-spiro[4.5]decan-4-one.

27. A compound of claim 16 wherein the compound is 8-(3,5-Bis-trifluoromethyl-benzoyl)-3-(3-chloro-pyrazin-2-yl)-1-phenyl-1,3,8-triaza-spiro[4.5]decan-4-one.

28. A compound of claim 16 wherein the compound is 8-(3,5-Bis-trifluoromethyl-benzoyl)-3-(3-chloro-quinoxalin-2-yl)-1-phenyl-1,3,8-triaza-spiro[4.5]decan-4-one.

29. A compound of claim 16 wherein the compound is 8-(3,5-Bis-trifluoromethyl-benzoyl)-3-(6-chloro-pyrazin-2-yl)-1-phenyl-1,3,8-triaza-spiro[4.5]decan-4-one.

30. A compound of claim 16 wherein the compound is 8-(3,5-Bis-trifluoromethyl-benzoyl)-3-(4,6-dimethoxy-pyrimidin-2-yl)-1-phenyl-1,3,8-triaza-spiro[4.5]decan-4-one.

31. A compound of claim 16 wherein the compound is 8-(3,5-Bis-trifluoromethyl-benzoyl)-3-(6-chloro-pyrimidin-4-yl)-1-phenyl-1,3,8-triaza-spiro[4.5]decan-4-one.

32. The compound of claim 5 wherein $R^1$ is substituted or unsubstituted —$(CH2)_m$-non aromatic heterocyclic or, —$(CH_2)_m$—NRR' and $R^2$ is Hydrogen.

33. A compound of claim 32 wherein the compound is 8-(3,5-Bis-trifluoromethyl-benzoyl)-3-(2-morpholin-4-yl-ethyl)-1-phenyl-1,3,8-triaza-spiro[4.5]decan-4-one.

34. A compound of claim 32 wherein the compound is 8-(3,5-Bis-trifluoromethyl-benzoyl)-1-phenyl-3-(2-piperidin-1-yl-ethyl)-1,3,8-triaza-spiro[4.5]decan-4-one.

35. A compound of claim 32 wherein the compound is 8-(3,5-Bis-trifluoromethyl-benzoyl)-1-phenyl-3-(2-pyrrolidin-1-yl-ethyl)-1,3,8-triaza-spiro[4.5]decan-4-one.

36. A compound of claim 32 wherein the compound is 8-(3,5-Bis-trifluoromethyl-benzoyl)-3-[3-(4-methyl-piperazin-1-yl)-propyl]-1-phenyl-1,3,8-triaza-spiro[4.5]decan-4-one.

37. A compound of claim 32 wherein the compound is 8-(3,5-Bis-trifluoromethyl-benzoyl)-3-[2-(4-methyl-piperazin-1-yl)-ethyl]-1-phenyl-1,3,8-triaza-spiro[4.5]decan-4-one.

38. A compound of claim 32 wherein the compound is 8-(3,5-Bis-trifluoromethyl-benzoyl)-3-(2-dimethylamino-ethyl)-1-phenyl-1,3,8-triaza-spiro[4.5]decan-4-one.

39. The compound of claim 32 wherein the compound is 8-(3,5-Bis-trifluoromethyl-benzoyl)-3-(3-isopropylamino-propyl)-1-phenyl-1,3,8-triaza-spiro[4.5]decan-4-one.

40. The compound of claim 32 wherein the compound is 8-(3,5-Bis-trifluoromethyl-benzoyl)-3-(2-isopropylamino-ethyl)-1-phenyl-1,3,8-triaza-spiro[4.5]decan-4-one.

41. The compound of claim 32 wherein the compound is 8-(3,5-Bis-trifluoromethyl-benzoyl)-3-(3-dimethylamino-propyl)-1-phenyl-1,3,8-triaza-spiro[4.5]decan-4-one.

42. The compound of claim 32 wherein the compound is 8-(3,5-Bis-trifluoromethyl-benzoyl)-3-(2-isopropylamino-ethyl)-1-phenyl-1,3,8-triaza-spiro[4.5]decan-4-one.

43. A compound of claim 32 wherein the compound is 8-(3,5-Bis-trifluoromethyl-benzoyl)-3-(4,5-dihydro-1H-imidazol-2-yl-methyl)-1-phenyl-1,3,8-triaza-spiro[4.5]decan-4 4-one.

44. A compound of claim 5 wherein $R^1$ is —$(CH_2)_m$—(O)—O-lower alkyl, —$(CH_2)_m$—O-lower alkyl or —$(CH_2)_m$—CH(OH)—$CH_2$—O-phenyl and $R^2$ is Hydrogen.

45. A compound of claim 44 wherein the compound is 3-[8-(3,5-Bis-trifluoromethyl-benzoyl)-4-oxo-1-phenyl-1,3,8-triaza-spiro[4.5]dec-3-yl]-propionic acid ethyl ester.

46. A compound of claim 44 wherein the compound is 3-[8-(3,5-Bis-trifluoromethyl-benzoyl)-4-oxo-1-phenyl-1,3,8-triaza-spiro[4.5]dec-3-yl]-propionic acid methyl ester.

47. A compound of claim 44 wherein the compound is [8-(3,5-Bis-trifluoromethyl-benzoyl)-4-oxo-1-phenyl-1,3,8-triaza-spiro[4.5]dec-3-yl]-acetic acid methyl ester.

48. A compound of claim 44 wherein the compound is 8-(3,5-Bis-trifluoromethyl-benzoyl)-3-methoxymethyl-1-phenyl-1,3,8-triaza-spiro[4.5]decan-4-one.

49. A compound of claim 44 wherein the compound is 2-[8-(3,5-Bis-trifluoromethyl-benzoyl)-4-oxo-1-phenyl-1,3,8-triaza-spiro[4.5]dec-3-yl]-malonic acid dimethyl ester.

50. A compound of claim 44 wherein the compound is (R,S)-8-(3,5-Bis-trifluoromethyl-benzoyl)-3-(2-hydroxy-3-phenoxy-propyl)-1-phenyl-1,3,8-triaza-spiro[4.5]decan-4-one.

51. A compound of claim 44 wherein the compound is [8-(3,5-Bis-trifluoromethyl-benzoyl)-4-oxo-1-phenyl-1,3,8-triaza-spiro[4.5]dec-3-yl]-acetic acid ethyl ester.

52. A compound of claim 5 wherein $R^1$ is —$(CH_2)_m$—$CF_3$, —$(CH_2)_m CN$ or —$(CH_2)_m OH$ and $R^2$ is as defined in claim 5.

53. A compound of claim 52 wherein the compound is 8-(3,5-Bis-trifluoromethyl-benzoyl)-3-(3-hydroxy-propyl)-1-phenyl-1,3,8-triaza-spiro[4.5]decan-4-one.

54. A compound of claim 52 wherein the compound is 8-(3,5-Bis-trifluoromethyl-benzoyl)-3-(2-hydroxy-ethyl)-1-phenyl-1,3,8-triaza-spiro[4.5]decan-4-one.

55. A compound of claim 53 wherein the compound is 8-(3,5-Bis-trifluoromethyl-benzoyl)-1-(3,4-dichloro-phenyl)-3-(4,6-dimethoxy-[1,3,5]triazin-2-yl)-1,3,8-triaza-spiro[4.5]decan-4-one.

56. A compound of claim 5 wherein $R^1$ is unsubstituted or substituted —$(CH_2)_m$-heteroaryl, m is 0, 1, 2, 3 or 4; and $R^2$ is halogen and n' is 1 or 2.

57. The compound if claim 56 wherein the compound is 8-(3,5-Bis-trifluoromethyl-benzoyl)-1-(3,4-dichloro-phenyl)-3-(4,6-dimethoxy-[1,3,5]triazin-2-yl)-1,3,8-triaza-spiro[4.5]decan-4-one.

58. The compound of claim 56 wherein the compound is 8-(3,5-Bis-trifluoromethyl-benzoyl)-1-(3-chloro-phenyl)-3-(4,6-dimethoxy-[1,3,5]triazin-2-yl)-1,3,8-triaza-spiro[4.5]decan-4-one.

59. The compound of claim 56 wherein the compound is 8-(3,5-Bis-trifluoromethyl-benzoyl)-1-(2-chloro-phenyl)-3-(4,6-dimethoxy-[1,3,5]triazin-2-yl)-1,3,8-triaza-spiro[4.5]decan-4-one.

60. The compound of claim 56 wherein the compound is 8-(3,5-Bis-trifluoromethyl-benzoyl)-1-(4-chloro-phenyl)-3-(4,6-dimethoxy-[1,3,5]triazin-2-yl)-1,3,8-triaza-spiro[4.5]decan-4-one.

61. The compound of claim 56 wherein the compound is 8-(3,5-Bis-trifluoromethyl-benzoyl)-1-(2-chloro-phenyl)-3-pyridin-3-yl-methyl-1,3,8-triaza-spiro[4.5]decan-4-one.

62. The compound of claim 56 wherein the compound is 3-(1-Benzyl-1H-imidazol-2-ylmethyl)-8-(3,5-bis-trifluoromethyl-benzoyl)-1-(2-chloro-phenyl)-1,3,8-triaza-spiro[4.5]decan-4-one.

63. The compound of claim 56 wherein the compound is 8-(3,5-Bis-trifluoromethyl-benzoyl)-1-(2-chloro-phenyl)-3-(2-methyl-thiazol-4-ylmethyl)-1,3,8-triaza-spiro[4.5]decan-4-one.

64. The compound of claim 56 wherein the compound is 8-(3,5-Bis-trifluoromethyl-benzoyl)-1-(2-chloro-phenyl)-3-(6-chloro-pyrimidin-4-yl)-1,3,8-triaza-spiro[4.5]decan-4-one.

65. The compound of claim 56 wherein the compound is 8-(3,5-Bis-trifluoromethyl-benzoyl)-1-(2-chloro-phenyl)-3-(3,5-dichloro-pyridin-2-yl)-1,3,8-triaza-spiro[4.5]decan-4-one.

66. The compound of claim 56 wherein the compound is 8-(3,5-Bis-trifluoromethyl-benzoyl)-1-(2-chloro-phenyl)-3-(4-trifluoromethyl-pyrimidin-2-yl)-1,3,8-triaza-spiro[4.5]decan-4-one.

67. The compound of claim 56 wherein the compound is 8-(3,5-Bis-trifluoromethyl-benzoyl)-1-(2-chloro-phenyl)-3-pyrimidin-2-yl-1,3,8-triaza-spiro[4.5]decan-4-one.

68. The compound of claim 56 wherein the compound is 8-(3,5-Bis-trifluoromethyl-benzoyl)-1-(2-chloro-phenyl)-3-(3,5-dimethyl-isoxazol-4-yl-methyl)-1,3,8-triaza-spiro[4.5]decan-4-one.

69. The compound of claim 56 wherein the compound is 8-(3,5-Bis-trifluoromethyl-benzoyl)-1-(2-chloro-phenyl)-3-pyridin-3-yl-1,3,8-triaza-spiro[4.5]decan-4-one.

70. The compound of claim 56 wherein the compound is 8-(3,5-Bis-trifluoromethyl-benzoyl)-1-(2-chloro-phenyl)-3-pyridin-4-yl-1,3,8-triaza-spiro[4.5]decan-4-one.

71. The compound of claim 5 wherein R1 is —(CH2)m—OH, unsubstituted or substituted-(CH2)m-heteroaryl, m is 0, 1, 2, 3 or 4; and R2 is lower alkyl or lower alkoxy.

72. The compound of claim 71 wherein the compound is 8-(3,5-Bis-trifluoromethyl-benzoyl)-3(2-hydroxy-ethyl)-1-o-tolyl-1,3,8-triaza-spiro[4.5]decan-4-one.

73. The compound of claim 71 wherein the compound is 8-(3,5-Bis-trifluoromethyl-benzoyl)-3-(4,6-dimethoxy-[1,3,5]triazin-2-yl)-1-o-tolyl-1,3,8-triaza-spiro[4.5]decan-4-one.

74. The compound of claim 71 wherein the compound is 8-(3,5-Bis-trifluoromethyl-benzoyl)-3-pyridin-3-yl-methyl-1-o-tolyl-1,3,8-triaza-spiro[4.5]decan-4-one.

75. The compound of claim 71 wherein the compound is 8-(3,5-Bis-trifluoromethyl-benzoyl)-1-(2-methoxy-phenyl)-3-pyridin-3-yl-methyl-1,3,8triaza-spiro[4.5]decan-4-one.

76. The compound of claim 71 wherein the compound is 8-(3,5-Bis-trifluoromethyl-benzoyl)-3-(4,6-dimethoxy-[1,3,5]triazin-2-yl)-1-(2-methoxy-phenyl)-1,3,8-triaza-spiro[4.5]decan-4-one.

77. The compound of claim 71 wherein the compound is 8-(3,5-Bis-trifluoromethyl-benzoyl)-3-(2-dimethylamino-ethyl)-1-o-tolyl-1,3,8-triaza-spiro[4.5]decan-4-one.

78. The compound of claim 71 wherein the compound is 8-(3,5-Bis-trifluoromethyl-benzoyl)-3-(2-isopropylamino-ethyl)-1-o-tolyl-1,3,8-triaza-spiro[4.5]decan-4-one.

79. The compound of claim 71 wherein the compound is 8-(3,5-Bis-trifluoromethyl-benzoyl)-3-(2-pyrrolidin-1-yl-ethyl)-1-o-tolyl-1,3,8-triaza-spiro[4.5]decan-4-one.

80. The compound of claim 71 wherein the compound is 8-(3,5-Bis-trifluoromethyl-benzoyl)-3-methyl-1-o-tolyl-1,3,8-triaza-spiro[4.5]decan-4-one.

81. The compound of claim 71 wherein the compound is 8-(3,5-Bis-trifluoromethyl-benzoyl)-3-(2-methyl-thiazol-4-yl-methyl)-1-o-tolyl-1,3,8-triaza-spiro[4.5]decan-4-one.

82. The compound of claim 5 wherein $R^1$ is Hydrogen, $R^2$ is lower alkyl, lower alkoxy or halogen and wherein n' is 1 or 2.

83. The compound of claim 82 wherein the compound is 8-(3,5-Bis-trifluoromethyl-benzoyl)-1-(3-chloro-phenyl)-1,3,8-triaza-spiro[4.5]decan-4-one.

84. The compound of claim 82 wherein the compound is 8-(3,5-Bis-trifluoromethyl-benzoyl)-1-(4-chloro-phenyl)-1,3,8-triaza-spiro[4.5]decan-4-one.

85. The compound of claim 82 wherein the compound is 8-(3,5-Bis-trifluoromethyl-benzoyl)-1-(3,4-dichloro-phenyl)-1,3,8-triaza-spiro[4.5]decan-4-one.

86. The compound of claim 82 wherein the compound is 8-(3,5-Bis-trifluoromethyl-benzoyl)-1-o-tolyl-1,3,8-triaza-spiro[4.5]decan-4-one.

87. The compound of claim 82 wherein the compound is 8-(3,5-Bis-trifluoromethyl-benzoyl)-1-(2-chloro-phenyl)-1,3,8-triaza-spiro[4.5]decan-4-one.

88. The compound of claim 82 wherein the compound is 8-(3,5-Bis-trifluoromethyl-benzoyl)-1-(2-methoxy-phenyl)-1,3,8-triaza-spiro[4.5]decan-4-one.

89. The compound of claim 5 wherein $R^1$ is —$(CH_2)_m$—C(O)—NRR', —$(CH_2)_m$—CH—(CF3)OH or unsubstituted or substituted-$(CH_2)_m$-non-aromatic heterocyclic, wherein m is 1, 2, 3 or 4 and $R^2$ is Hydrogen or halogen.

90. The compound of claim 89 wherein the compound is 2-[8-(3,5-Bis-trifluoromethyl-benzoyl)-4-oxo-1-phenyl-1,3,8-triaza-spiro[4.5]dec-3-yl]-acetamide.

91. The compound of claim 89 wherein the compound is 2-[8-(3,5-Bis-trifluoromethyl-benzoyl)-4-oxo-1-phenyl-1,3,8-triaza-spiro[4.5]dec-3-yl]-N,N-dimethyl-acetamide.

92. The compound of claim 89 wherein the compound is (S)-8-(3,5-Bis-trifluoromethyl-benzoyl)-1-phenyl-3-(4,4,4-trifluoro-3-hydroxy-butyl)-1,3,8-triaza-spiro[4.5]decan-4-one.

93. The compound of claim 89 wherein the compound is 8-(3,5-Bis-trifluoromethyl-benzoyl)-1-(2-chloro-phenyl)-3-methyl-1,3,8-triaza-spiro[4.5]decan-4-one.

94. The compound of claim 89 wherein the compound is 8-(3,5-Bis-trifluoromethyl-benzoyl)-1-(2-chloro-phenyl)-3-(2-oxo-oxazolidin-5-ylmethyl)-1,3,8-triaza-spiro[4.5]decan-4-one.

95. The compound of claim 89 wherein the compound is 8-(3,5-Bis-trifluoromethyl-benzoyl)-1-(2-chloro-phenyl)-3-(2-dimethylamino-ethyl)-1,3,8-triaza-spiro[4.5]decan-4-one.

96. The compound of claim 89 wherein the compound is 8-(3,5-Bis-trifluoromethyl-benzoyl)-1-(2-chloro-phenyl)-3-(2-pyrrolidin-1-yl-ethyl)-1,3,8-triaza-spiro[4.5]decan-4-one.

97. The compound of claim 89 wherein the compound is 2-[8-(3,5-Bis-trifluoromethyl-benzoyl)-1-(2-chloro-phenyl)-4-oxo-1,3,8-triaza-spiro[4.5]dec-3-yl]-N,N-dimethyl-acetamide.

98. The compound of claim 89 wherein the compound is 8-(3,5-Bis-trifluoromethyl-benzoyl)-1-(2-chloro-phenyl)-3-(3-dimethylamino-propyl)-1,3,8-triaza-spiro[4.5]decan-4-one.

99. The compound of claim 2 having the formula

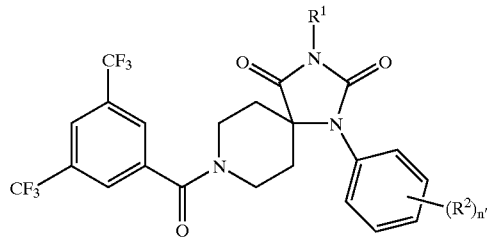

wherein $R^1$ and $R^2$ are as defined in claim 2.

100. The compound of claim 99 wherein $R^1$ is hydrogen, lower alkyl, phenyl or —$(CH_2)$-unsubstituted or substituted heterocyclic non-aromatic heterocyclic; $R^2$ is Hydrogen or lower alkyl and m is 1, 2, 3, 4.

101. The compound of claim 100 wherein the compound is 8-(3,5-Bis-trifluoromethyl-benzoyl)-1-phenyl-1,3,8-triaza-spiro[4.5]decane-2,4-dione.

102. The compound of claim 100 wherein the compound is 8-(3,5-Bis-trifluoromethyl-benzoyl)-1-o-tolyl-1,3,8-triaza-spiro[4.5]decane-2,4-dione.

103. The compound of claim 100 wherein the compound is 8-(3,5-Bis-trifluoromethyl-benzoyl)-1,3-diphenyl-1,3,8-triaza-spiro[4.5]decane-2,4-dione.

104. The compound of claim 100 wherein the compound is 8-(3,5-Bis-trifluoromethyl-benzoyl)-3-(2-pyrrolidin-1-yl-ethyl)-1-o-tolyl-1,3,8-triaza-spiro[4.5]decane-2,4-dione.

105. The compound of claim 100 wherein the compound is 8-(3,5-Bis-trifluoromethyl-benzoyl)-3-(2-oxo-oxazolidin-5-yl-methyl)-1-o-tolyl-1,3,8-triaza-spiro[4.5]decane-2,4-dione.

106. The compound of claim 100 wherein the compound is (S)-8-(3,5-Bis-trifluoromethyl-benzoyl)-3-(5-oxo-pyrrolidin-2-yl-methyl)-1-phenyl-1,3,8-triaza-spiro[4.5]decane-2,4-dione.

107. The compound of claim 100 wherein the compound is 8-(3,5-Bis-trifluoromethyl-benzoyl)-3-(2-morpholin-4-yl-ethyl)-1-o-tolyl-1,3,8-triaza-spiro[4.5]decane-2,4-dione.

108. The compound of claim 100 wherein the compound is 8-(3,5-Bis-trifluoromethyl-benzoyl)-1-(2-chloro-phenyl)-1,3,8-triaza-spiro[4.5]decane-2,4-dione.

109. The compound of claim 100 wherein the compound is 8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione, 8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione, or 8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione.

110. The compound of claim 99 wherein $R^1$ is selected from the group consisting of lower alkyl, —(CH2)m-unsubstituted and substituted heteroaromatic, m=0, 1, 2, 3, 4.

111. The compound of claim 110 wherein the compound is 8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione.

112. The compound of claim 110 wherein the compound is 8-(3,5-Bis-trifluoromethyl-benzoyl)-3-pyridin-3-yl-methyl-1-o-tolyl-1,3,8-triaza-spiro[4.5]decane-2,4-dione.

113. The compound of claim 110 wherein the compound is 8-(3,5-Bis-trifluoromethyl-benzoyl)-3-(3,5-dimethylisoxazol-4-yl-methyl)-1-o-tolyl-1,3,8-triaza-spiro[4.5]decane-2,4-dione.

114. The compound of claim 110 wherein the compound is 3-(1H-Benzoimidazol-2-yl-methyl)-8-(3,5-bis-trifluoromethyl-benzoyl)-1-o-tolyl-1,3,8-triaza-spiro[4.5]decane-2,4-dione.

115. The compound of claim 110 wherein the compound is 8-(3,5-Bis-trifluoromethyl-benzoyl)-3-(2-methyl-thiazol-4-yl-methyl)-1-o-tolyl-1,3,8-triaza-spiro[4.5]decane-2,4-dione.

116. The compound of claim 110 wherein the compound is 8-(3,5-Bis-trifluoromethyl-benzoyl)-3-[1,2,4]oxadiazol-3-yl-methyl-1-o-tolyl-1,3,8-triaza-spiro[4.5]decane-2,4-dione.

117. The compound of claim 110 wherein the compound is 8-(3,5-Bis-trifluoromethyl-benzoyl)-3-furan-2-yl-methyl-1-phenyl-1,3,8-triaza-spiro[4.5]decane-2,4-dione.

118. The compound of claim 110 wherein the compound is 8-(3,5-Bis-trifluoromethyl-benzoyl)-3-furan-3-yl-methyl-1-phenyl-1,3,8-triaza-spiro[4.5]decane-2,4-dione.

119. The compound of claim 110 wherein the compound is 8-(3,5-Bis-trifluoromethyl-benzoyl)-3-furan-2-yl-methyl-1-o-tolyl-1,3,8-triaza-spiro[4.5]decane-2,4-dione.

120. The compound of claim 110 wherein the compound is 8-(3,5-Bis-trifluoromethyl-benzoyl)-3-thiophen-2-yl-methyl-1-o-tolyl-1,3,8-triaza-spiro[4.5]decane-2,4-dione.

121. The compound of claim 110 wherein the compound is 8-(3,5-Bis-trifluoromethyl-benzoyl)-3-(5-methyl-isoxazol-3-yl-methyl)-1-o-tolyl-1,3,8-triaza-spiro[4.5]decane-2,4-dione.

122. The compound of claim 110 wherein the compound is 8-(3,5-Bis-trifluoromethyl-benzoyl)-3-furan-3-yl-ethyl-1-o-tolyl-1,3,8-triaza-spiro[4.5]decane-2,4-dione.

123. The compound of claim 99 wherein $R^1$ is —(CH2)m-unsubstituted or substituted heteroaromatic and $R^2$ is halogen.

124. The compound of claim 123 wherein the compound is 8-(3,5-Bis-trifluoromethyl-benzoyl)-1-(2-chloro-phenyl)-3-(1-methyl-1H-imidazol-2-ylmethyl)-1,3,8-triaza-spiro[4.5]decane-2,4-dione.

125. The compound of claim 123 wherein the compound is 8-(3,5-Bis-trifluoromethyl-benzoyl)-1-(2-chloro-phenyl)-3-(1,5-dimethyl-1H-pyrazol-3-ylmethyl)-1,3,8-triaza-spiro[4.5]decane-2,4-dione.

126. The compound of claim 1 having the structure

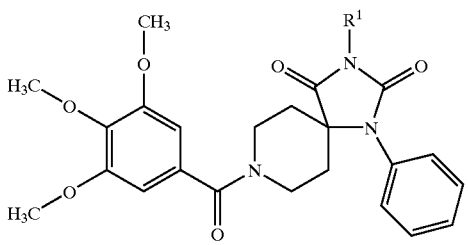

I-e wherein $R^1$ is hydrogen.

127. The compound of claim 1 having the structure

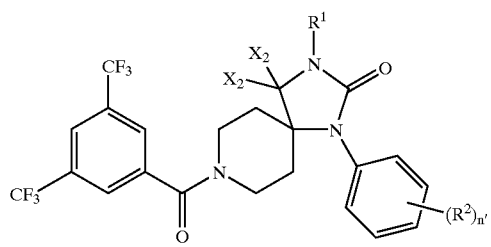

I-f wherein $R^1$, $R^2$, $X^1$ and $X^2$ are as defined in claim 1.

128. The compound of claim 127 wherein $X^1$ or $X^2$ is Hydrogen, Hydroxy or lower alkoxy, $R^1$ is Hydrogen, phenyl or —(CH_2)_m-unsubstituted or substituted non-aromatic heterocyclic; and $R^2$ is hydrogen or lower alkyl.

129. The compound of claim 128 wherein the compound is 8-(3,5-Bis-trifluoromethyl-benzoyl)-4-hydroxy-1,3-diphenyl-1,3,8-triaza-spiro[4.5]decan-2-one.

130. The compound of claim 129 wherein the compound is 8-(3,5-Bis-trifluoromethyl-benzoyl)-4-methoxy-1,3-diphenyl-1,3,8-triaza-spiro[4.5]decan-2-one.

131. The compound of claim 128 wherein the compound is 8-(3,5-Bis-trifluoromethyl-benzoyl)-4-methoxy-1,3-diphenyl-1,3,8-triaza-spiro[4.5]decan-2-one.

132. The compound of claim 128 wherein the compound is 8-(3,5-Bis-trifluoromethyl-benzoyl)-3-(2-pyrrolidin-1-yl-ethyl)-1-o-tolyl-1,3,8-triaza-spiro[4.5]decan-2-one.

133. The compound of claim 1 having the structure

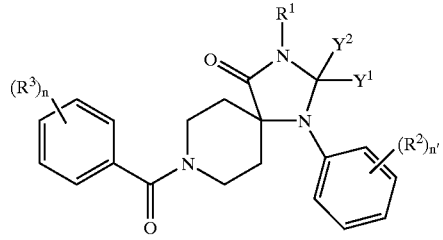

Ig wherein $Y^1$, $Y^2$, $R^1$, $R^2$ and $R^3$ are as defined in claim 1.

134. The compound of claim 133 wherein $R^1$ is H, $R^2$ is lower alkyl and $R^3$ is halogen, lower alkoxy or $CF_3$.

135. The compound of claim 134 wherein the compound is (rac)-8-(3,5-Dimethoxy-benzoyl)-2-methyl-1-o-tolyl-1,3,8-triaza-spiro[4.5]decan-4-one.

136. The compound of claim 134 wherein the compound is (rac)-8-(3,5-Dichloro-benzoyl)-2-methyl-1-o-tolyl-1,3,8-triaza-spiro[4.5]decan-4-one.

137. The compound of claim 134 wherein the compound is rac)-8-(3-Fluoro-5-trifluoromethyl-benzoyl)-2-methyl-1-o-tolyl-1,3,8-triaza-spiro[4.5]decan-4-one.

138. The compound of claim 134 wherein the compound is rac)-8-(3,5-Difluoro-benzoyl)-2-methyl-1-o-tolyl-1,3,8-triaza-spiro[4.5]decan-4-one.

139. The compound of claim 133 wherein R1 is —(CH2)m-substituted or unsubstituted heteroaryl.

140. The compound of claim 139 wherein the compound is -(3,5-Bis-trifluoromethyl-benzoyl)-3-(1-methyl-1H-imidazol-2-yl-methyl)-1-o-tolyl-1,3,8-triaza-spiro[4.5]decan-4-one.

141. The compound of claim 1 having the structure

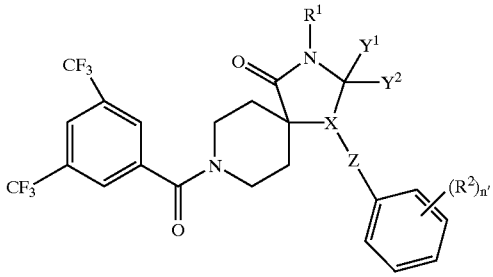

I-h wherein $R^1$ is hydrogen, —$(CH_2)_m$— nonaromatic heterocyclic or lower alkyl; $R^2$ is hydrogen or halogen; X, $Y^1$, $Y^2$ and Z are as defined in claim 1.

142. The compound of claim 141 wherein $Y^1$ and $Y^2$ are hydrogen and Z is —$(CH_2)$— or —$C(O)$—.

143. The compound of claim 142 wherein the compound is 1-Benzyl-8-(3,5-bis-trifluoromethyl-benzoyl)-1,3,8-triaza-spiro[4.5]decan-4-one.

144. The compound of claim 142 wherein the compound is 1-Benzyl-8-(3,5-bis-trifluoromethyl-benzoyl)-3-methyl-1,3,8-triaza-spiro[4.5]decan-4-one.

145. The compound of claim 142 wherein the compound is 1-Benzyl-8-(3,5-bis-trifluoromethyl-benzoyl)-3-(2-pyrrolidin-1-yl-ethyl)-1,3,8-triaza-spiro[4.5]decan-4-one hydrochloride.

146. The compound of claim 142 wherein the compound is 8-(3,5-Bis-trifluoromethyl-benzoyl)-1-(2-chloro-benzyl)-1,3,8-triaza-spiro[4.5]decan-4-one.

147. The compound of claim 142 wherein the compound is 8-(3,5-Bis-trifluoromethyl-benzoyl)-1-(3-chloro-benzyl)-3-methyl-1,3,8-triaza-spiro[4.5]decan-4-one.

148. The compound of claim 142 wherein the compound is 1-Benzoyl-8-(3,5-bis-trifluoromethyl-benzoyl)-1,3,8-triaza-spiro[4.5]decan-4-one.

149. The compound of claim 141 wherein one of $Y^1$ and $Y^2$ is hydrogen, and the other is lower alkyl; Z is —$(CH_2)_0$—; and $R^1$ is hydrogen, lower alkyl, —$(CH_2)_m$—NRR', —$(CH_2)_m$-cyclo alkyl or —$(CH_2)_m$-unsubstituted non aromatic heterocyclic.

150. The compound of claim 149 wherein the compound is (rac)-8-(3,5-Bis-trifluoromethyl-benzoyl)-2-methyl-1-phenyl-1,3,8-triaza-spiro[4.5]decan-4-one.

151. The compound of claim 149 wherein the compound is (rac)-8-(3,5-Bis-trifluoromethyl-benzoyl)-2-isopropyl-1-phenyl-1,3,8-triaza-spiro[4.5]decan-4-one.

152. The compound of claim 149 wherein the compound is (rac)-2-Benzyl-8-(3,5-bis-trifluoromethyl-benzoyl)-1-phenyl-1,3,8-triaza-spiro[4.5]decan-4-one.

153. The compound of claim 149 wherein the compound is (rac)-8-(3,5-Bis-trifluoromethyl-benzoyl)-2,3-dimethyl-1-phenyl-1,3,8-triaza-spiro[4.5]decan-4-one.

154. The compound of claim 149 wherein the compound is (rac)-8-(3,5-Bis-trifluoromethyl-benzoyl)-2-methyl-1-phenyl-3-(2-pyrrolidin-1-yl-ethyl)-1,3,8-triaza-spiro[4.5]decan-4-one.

155. The compound of claim 149 wherein the compound is (rac)-8-(3,5-Bis-trifluoromethyl-benzoyl)-3-cyclopropylmethyl-2-methyl-1-phenyl-1,3,8-triaza-spiro[4.5]decan-4-one.

156. The compound of claim 149 wherein the compound is (rac)-8-(3,5-Bis-trifluoromethyl-benzoyl)-3-(3-dimethylamino-propyl)-2-methyl-1-phenyl-1,3,8-triaza-spiro[4.5]decan-4-one.

157. The compound of claim 149 wherein the compound is (rac)-8-(3,5-Bis-trifluoromethyl-benzoyl)-2,3-dimethyl-1-o-tolyl-1,3,8-triaza-spiro[4.5]decan-4-one.

158. The compound of claim 149 wherein the compound is (rac)-8-(3,5-Bis-trifluoromethyl-benzoyl)-2-methyl-3-(2-pyrrolidin-1-yl-ethyl)-1-o-tolyl-1,3,8-triaza-spiro[4.5]decan-4-one.

159. The compound of claim 149 wherein the compound is (rac)-8-(3,5-Bis-trifluoromethyl-benzoyl)-2-methyl-3-(2-piperidin-1-yl-ethyl)-1-o-tolyl-1,3,8-triaza-spiro[4.5]decan-4-one.

160. The compound of claim 149 wherein the compound is (rac)-8-(3,5-Bis-trifluoromethyl-benzoyl)-2-methyl-3-(2-piperazin-1-yl-ethyl)-1-o-tolyl-1,3,8-triaza-spiro[4.5]decan-4-one.

161. The compound of claim 149 wherein the compound is Rac-8-(3,5-Bis-trifluoromethyl-benzoyl)-3-cyclopropylmethyl-2-methyl-1-o-tolyl-1,3,8-triaza-spiro[4.5]decan-4-one.

162. The compound of claim 149 wherein the compound is Rac-8-(3,5-Bis-trifluoromethyl-benzoyl)-2-methyl-3-(2-morpholin-4-yl-ethyl)-1-o-tolyl-1,3,8triaza-spiro[4.5]decan-4-one.

163. The compound of claim 141 wherein one of $Y^1$ and $Y^2$ is hydrogen, and the other of $Y^1$ and $Y^2$ is lower alkyl; Z is —$(CH_2)_0$—; $R^1$ is phenyl, —$(CH_2)_m$—O-lower alkyl, —$(CH_2)_m$—$CHF_2$ or lower alkenyl; and $R^2$ is lower alkyl.

164. The compound of claim 163 wherein the compound is Rac-8-(3,5-Bis-trifluoromethyl-benzoyl)-2-methyl-3-phenyl-1-o-tolyl-1,3,8-triaza-spiro[4.5]decan-4-one.

165. The compound of claim 163 wherein the compound is Rac-8-(3,5-Bis-trifluoromethyl-benzoyl)-3-(2-methoxy-ethyl)-2-methyl-1-o-tolyl-1,3,8-triaza-spiro[4.5]decan-4-one.

166. The compound of claim 163 wherein the compound is Rac-8-(3,5-Bis-trifluoromethyl-benzoyl)-3-(2,2-difluoro-ethyl)-2-methyl-1-o-tolyl-1,3,8-triaza-spiro[4.5]decan-4-one.

167. The compound of claim 163 wherein the compound is Rac-8-(3,5-Bis-trifluoromethyl-benzoyl)-2-methyl-3-(3-methyl-but-2-enyl)-1-o-tolyl-1,3,8-triaza-spiro[4.5]decan-4-one.

168. The compound of claim 141 wherein one of $Y^1$ and $Y^2$ is hydrogen, and the other of $Y^1$ and $Y^2$ is lower alkyl; Z— is —$(CH_2)_0$—; $R^1$ is unsubstituted —$(CH_2)_m$— aromatic heterocyclic or substituted —$(CH_2)_m$— aromatic heterocyclic; and $R_2$ is hydrogen or lower alkyl.

169. The compound of claim 168 wherein the compound is (rac)-8-(3,5-Bis-trifluoromethyl-benzoyl)-2-methyl-1-phenyl-3-pyridin-3-yl-methyl-1,3,8-triaza-spiro[4.5]decan-4-one.

170. The compound of claim 168 wherein the compound is (rac)-8-(3,5-Bis-trifluoromethyl-benzoyl)-2-methyl-3-(2-methyl-thiazol-4-yl-methyl)-1-phenyl-1,3,8-triaza-spiro[4.5]decan-4-one.

171. The compound of claim 169 wherein the compound is (rac)-8-(3,5-Bis-trifluoromethyl-benzoyl)-2-methyl-1-phenyl-3-pyridin-4-yl-1,3,8-triaza-spiro[4.5]decan-4-one.

172. The compound of claim 141 wherein one of $Y^1$ and $Y^2$ is hydrogen, and the other of $Y^1$ and $Y^2$ is —$(CH_2)_m$—phenyl; Z is —$(CH_2)_0$—; $R^1$ is hydrogen or lower alkyl; and $R^2$ is hydrogen or lower alkyl.

173. The compound of claim 172 wherein the compound is (rac)-8-(3,5-Bis-trifluoromethyl-benzoyl)-2-phenethyl-1-phenyl-1,3,8-triaza-spiro[4.5]decan-4-one.

174. The compound of claim 172 wherein the compound is (rac)-2-Benzyl-8-(3,5-bis-trifluoromethyl-benzoyl)-1-phenyl-1,3,8-triaza-spiro[4.5]decan-4-one.

175. The compound of claim 172 wherein the compound is (rac)-8-(3,5-Bis-trifluoromethyl-benzoyl)-1,2-diphenyl-1,3,8-triaza-spiro[4.5]decan-4-one.

176. The compound of claim 172 wherein the compound is (rac)-2-Benzyl-8-(3,5-bis-trifluoromethyl-benzoyl)-1-o-tolyl-1,3,8-triaza-spiro[4.5]decan-4-one.

177. The compound of claim 172 wherein the compound is (rac)-8-(3,5-Bis-trifluoromethyl-benzoyl)-2-phenyl-1-o-tolyl-1,3,8-triaza-spiro[4.5]decan-4-one.

178. The compound of claim 1 having the structure

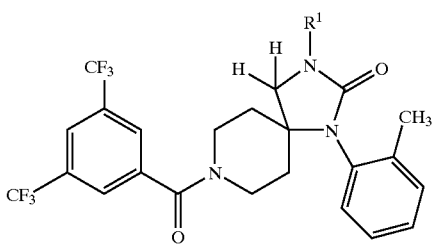

I-i wherein $R^1$ is —$(CH_2)_m$-cycloalkyl, —$(CH_2)_m$-unsubstituted heterocyclic, —$(CH_2)_m$—O-lower alkyl, —$(CH_2)_m$—NRR' or —$(CH_2)_m$—C(O)-lower alkyl; and m=0, 1, 2, 3, 4.

179. The compound of claim 178 wherein the compound is 8-(3,5-Bis-trifluoromethyl-benzoyl)-3-cyclopropylmethyl-1-o-tolyl-1,3,8-triaza-spiro[4.5]decan-2-one.

180. The compound of claim 178 wherein the compound is 8-(3,5-Bis-trifluoromethyl-benzoyl)-3-methyl-1-o-tolyl-1,3,8-triaza-spiro[4.5]decan-2-one.

181. The compound of claim 178 wherein the compound is 8-(3,5-Bis-trifluoromethyl-benzoyl)-3-(2-morpholin-4-yl-ethyl)-1-o-tolyl-1,3,8-triaza-spiro[4.5]decan-2-one.

182. The compound of claim 178 wherein the compound is 8-(3,5-Bis-trifluoromethyl-benzoyl)-3-(2-methoxy-ethyl)-1-o-tolyl-1,3,8-triaza-spiro[4.5]decan-2-one.

183. The compound of claim 178 wherein the compound is 8-(3,5-Bis-trifluoromethyl-benzoyl)-3-(3-dimethylamino-propyl)-1-o-tolyl-1,3,8-triaza-spiro[4.5]decan-2-one.

184. The compound of claim 178 wherein the compound is 3-Acetyl-8-(3,5-bis-trifluoromethyl-benzoyl)-1-o-tolyl-1,3,8-triaza-spiro[4.5]decan-2-one.

185. The compound of claim 1 having the structure

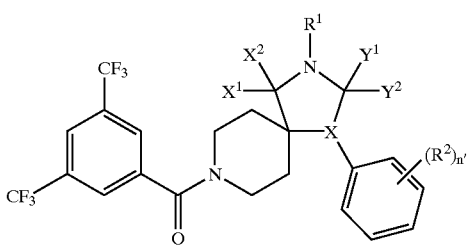

I-j wherein $R^1$ is lower alkyl; $R^2$ is hydrogen; $X^1$, $X^2$, $Y^1$ and $Y^2$ are as defined in claim 1 and X is >CH—.

186. The compound of claim 185 wherein the compound is (rac)-(3,5-Bis-trifluoromethyl-phenyl)-(2-methyl-4-phenyl-2,8-diaza-spiro[4.5]dec-8-yl)-methanone.

187. The compound of claim 185 wherein $X^1$ and $X^2$ are taken together to form an oxo group, $Y^1$ and $Y^2$ are each hydrogen, $R^2$ is hydrogen or lower alkyl and $R^1$ is hydrogen, lower alkyl, —$(CH_2)_m$-cycloalkyl, —$(CH_2)_m$-unsubstituted non-aromatic heterocyclic, —$(CH_2)_m$—O-lower alkyl, —$(CH_2)_m$—NRR', —$(CH_2)_m$—C(O)-lower alkyl or —$(CH_2)_m$ unsubstituted heteroaryl.

188. The compound of claim 187 wherein the compound is (rac)-8-(3,5-Bis-trifluoromethyl-benzoyl)-4-phenyl-2,8-diaza-spiro[4.5]decan-1-one.

189. The compound of claim 187 wherein the compound is (rac)-8-(3,5-Bis-trifluoromethyl-benzoyl)-2-methyl-4-phenyl-2,8-diaza-spiro[4.5]decan-1-one.

190. The compound of claim 187 wherein the compound is (rac)-8-(3,5-Bis-trifluoromethyl-benzoyl)-4-phenyl-2-(2-pyrrolidin-1-yl-ethyl)-2,8-diaza-spiro[4.5]decan-1-one.

191. The compound of claim 187 wherein the compound is (rac)-8-(3,5-Bis-trifluoromethyl-benzoyl)-2-(2-methoxy-ethyl)-4-phenyl-2,8-diaza-spiro[4.5]decan-1-one.

192. The compound of claim 187 wherein the compound is (rac)-8-(3,5-Bis-trifluoromethyl-benzoyl)-2-(2-morpholin-4-yl-ethyl)-4-phenyl-2,8-diaza-spiro[4.5]decan-1-one.

193. The compound of claim 187 wherein the compound is (rac)-8-(3,5-Bis-trifluoromethyl-benzoyl)-2-(3-dimethylamino-propyl)-4-phenyl-2,8-diaza-spiro[4.5]decan-1-one.

194. The compound of claim 187 wherein the compound is (rac)-8-(3,5-Bis-trifluoromethyl-benzoyl)-4-phenyl-2-pyridin-3-yl-methyl-2,8-diaza-spiro[4.5]decan-1-one.

195. The compound of claim 187 wherein the compound is 8-(3,5-Bis-trifluoromethyl-benzoyl)-2-pyridin-3-yl-methyl-4-o-tolyl-2,8-diaza-spiro[4.5]dec-3-en-1-one.

196. The compound of claim 187 wherein the compound is (rac)-8-(3,5-Bis-trifluoromethyl-benzoyl)-4-o-tolyl-2,8-diaza-spiro[4.5]decan-1-one.

197. The compound of claim 185 wherein $X^1$ and $X^2$ are taken together to form an oxo group; $Y^1$ and $Y^2$ are taken together to form an oxo group; $R^1$ is hydrogen, lower alkyl, —$(CH_2)_m$-unsubstituted non-aromatic heterocyclic or —$(CH_2)_m$—NRR'; and $R^2$ is hydrogen.

198. The compound of claim 197 wherein the compound is (rac)-8-(3,5-Bis-trifluoromethyl-benzoyl)-4-phenyl-2,8-diaza-spiro[4.5]decane-1,3-dione.

199. The compound of claim 197 wherein the compound is (rac)-8-(3,5-Bis-trifluoromethyl-benzoyl)-2-methyl-4-phenyl-2,8-diaza-spiro[4.5]decane-1,3-dione.

200. The compound of claim 197 wherein the compound is (rac)-8-(3,5-Bis-trifluoromethyl-benzoyl)-2-(2-morpholin-4-yl-ethyl)-4-phenyl-2,8-diaza-spiro[4.5]decane-1,3-dione.

201. The compound of claim 197 wherein the compound is (rac)-8-(3,5-Bis-trifluoromethyl-benzoyl)-4-phenyl-2-(2-pyrrolidin-1-yl-ethyl)-2,8-diaza-spiro[4.5]decane-1,3-dione.

202. The compound of claim 197 wherein the compound is (rac)-8-(3,5-Bis-trifluoromethyl-benzoyl)-2-(3-dimethylamino-propyl)-4-phenyl-2,8-diaza-spiro[4.5]decane-1,3-dione.

203. A compound having the structure

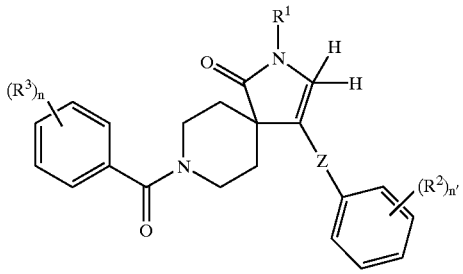

wherein
R$^1$ is hydrogen, lower alkyl, lower alkenyl, phenyl or the following groups
— (CH$_2$)$_m$-non aromatic heterocyclic, which is unsubstituted or substituted by lower alkyl, or is
— (CH$_2$)$_m$-heteroaryl, which is unsubstituted or substituted by one or two substituents selected from the group consisting of lower alkyl, lower alkoxy, halogen, CF$_3$, benzyl or cyano, or is
— (CH$_2$)$_m$—C(O)—NRR',
— (CH$_2$)$_m$—C(O)-lower alkyl,
— (CH$_2$)$_m$—C(O)—O-lower alkyl,
— (CH$_2$)$_m$—O-lower alkyl,
— (CH$_2$)$_m$—CH[C(O)—O-lower alkyl]$_2$,
— (CH$_2$)$_m$CH(OH)—CH$_2$—O-phenyl,
— (CH$_2$)$_m$—CH(CF$_3$)OH,
— (CH$_2$)$_m$—OH,
— (CH$_2$)$_m$—CN,
— (CH$_2$)$_m$—NRR',
— (CH$_2$)$_m$-cycloalkyl or
— (CH$_2$)$_m$—CHF$_2$
R$^2$ is hydrogen, lower alkyl, halogen or lower alkoxy;
R$^3$ is lower alkyl, lower alkoxy, halogen or CF$_3$;
R,R' are the same or different and are hydrogen or lower alkyl;
X$^1$/X$^2$ are hydrogen, hydroxy or lower alkoxy or taken together to form an oxo group;
Z —(CH$_2$)$_q$— or 13 C(O)—;
m is 0, 1, 2, 3 or 4;
n is 2 or 3;
n' 0, 1 or 2;
q is 0 or 1;
or a pharmaceutically acceptable acid addition salt thereof.

204. The compound of claim 203 having the structure

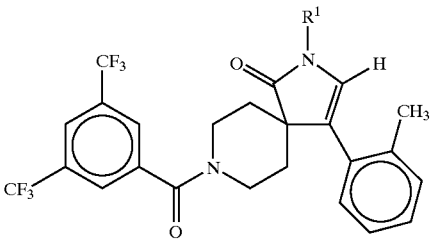

wherein is R$^1$ as defined in claim 203.

205. The compound of claim 204 wherein R$^1$ is hydrogen, lower alkyl, —(CH$_2$)$_m$-cycloalkyl, —(CH$_2$)$_m$—NRR' or —(CH$_2$)$_m$-unsubstituted non-aromatic; and m=0, 1, 2, 3, 4.

206. The compound of claim 205 wherein the compound is 8-(3,5-Bis-trifluoromethyl-benzoyl)-4-o-tolyl-2,8-diaza-spiro[4.5]dec-3-en-1-one.

207. The compound of claim 205 wherein the compound is 8-(3,5-Bis-trifluoromethyl-benzoyl)-4-o-tolyl-2,8-diaza-spiro[4.5]dec-3-en-1-one.

208. The compound of claim 205 wherein the compound is 8-(3,5-Bis-trifluoromethyl-benzoyl)-2-cyclopropylmethyl-4-o-tolyl-2,8-diaza-spiro[4.5]dec-3-en-1-one.

209. The compound of claim 205 wherein the compound is 8-(3,5-Bis-trifluoromethyl-benzoyl)-2-(2-pyrrolidin-1-yl-ethyl)-4-o-tolyl-2,8-diaza-spiro[4.5]dec-3-en-1-one.

210. The compound of claim 205 wherein the compound is 8-(3,5-Bis-trifluoromethyl-benzoyl)-2-(2-morpholin-4-yl-ethyl)-4-o-tolyl-2,8-diaza-spiro[4.5]dec-3-en-1-one.

211. The compound of claim 205 wherein the compound is 8-(3,5-Bis-trifluoromethyl-benzoyl)-2-(3-dimethylamino-propyl)-4-o-tolyl-2,8-diaza-spiro[4.5]dec-3-en-1-one.

* * * * *

UNITED STATES PATENT AND TRADEMARK OFFICE
CERTIFICATE OF CORRECTION

PATENT NO.    : 6,482,829 B2
DATED         : November 19, 2002
INVENTOR(S)   : Guido Galley et al.

It is certified that error appears in the above-identified patent and that said Letters Patent is hereby corrected as shown below:

<u>Title page, Item [54] and Column 1, line 1,</u>
Replace "SIPRODECANE" with -- SPIRODECANE --.

<u>Column 67,</u>
Line 15, delete "4" second instance.

<u>Column 72,</u>
Line 23, replace "129" with -- 128 --.

<u>Column 77,</u>
Lines 2-14, replace the present structure with:
   --

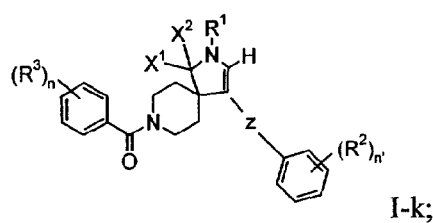

I-k;
   --
Line 43, delete "13", and replace "C(O)-" with -- -C(O)- --.

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,482,829 B2
DATED : November 19, 2002
INVENTOR(S) : Guido Galley et al.

It is certified that error appears in the above-identified patent and that said Letters Patent is hereby corrected as shown below:

Column 8,
Line 53, delete the "ps" at the end of the line.

Column 11,
Line 17, "with a compound of formula" should read
-- with a compound of formula

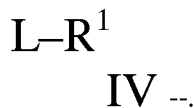

IV --.

Column 15,
Lines 30 to 40, the formula reads "

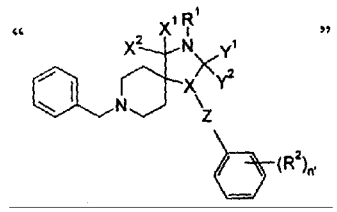

"

The formula should read --

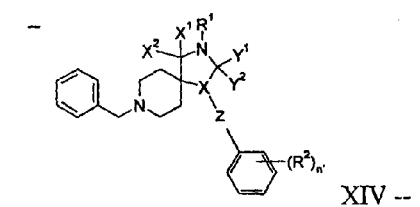

XIV --.

Signed and Sealed this

Tenth Day of August, 2004

JON W. DUDAS
*Acting Director of the United States Patent and Trademark Office*